United States Patent
Stachel et al.

(10) Patent No.: US 8,354,545 B2
(45) Date of Patent: Jan. 15, 2013

(54) 3,4-SUBSTITUTED PYRROLIDINE BETA-SECRETASE INHIBITORS FOR THE TREATMENT OF ALZHEIMER'S DISEASE

(75) Inventors: Shawn J. Stachel, Perkasie, PA (US); Thomas Steele, Schwenksville, PA (US); Alessia Petrocchi, Boston, MA (US)

(73) Assignees: Merck, Sharp & Dohme, Corp., Rahway, NJ (US); Istituto di Ricerche di Biologia Molecolare P Angeletti SPA, Rome (IT)

( * ) Notice: Subject to any disclaimer, the term of this patent is extended or adjusted under 35 U.S.C. 154(b) by 167 days.

(21) Appl. No.: 12/747,605

(22) PCT Filed: Dec. 10, 2008

(86) PCT No.: PCT/US2008/013550
§ 371 (c)(1),
(2), (4) Date: Jun. 11, 2010

(87) PCT Pub. No.: WO2009/078932
PCT Pub. Date: Jun. 25, 2009

(65) Prior Publication Data
US 2010/0280009 A1    Nov. 4, 2010

Related U.S. Application Data

(60) Provisional application No. 61/007,782, filed on Dec. 14, 2007.

(51) Int. Cl.
| | |
|---|---|
| C07D 401/06 | (2006.01) |
| C07D 207/06 | (2006.01) |
| C07D 403/14 | (2006.01) |
| C07D 413/06 | (2006.01) |
| A61K 31/535 | (2006.01) |
| A61K 31/445 | (2006.01) |
| A61K 31/415 | (2006.01) |
| A61K 31/4025 | (2006.01) |

(52) U.S. Cl. ............ 548/518; 548/364.1; 546/208; 546/17; 544/141; 514/237.2; 514/278; 514/326; 514/403; 514/422

(58) Field of Classification Search .......... None
See application file for complete search history.

(56) References Cited

U.S. PATENT DOCUMENTS

| 7,419,990 B2* | 9/2008 | Sings et al. ............ 514/326 |
| 2005/0176772 A1 | 8/2005 | Calabrese |
| 2006/0287287 A1 | 12/2006 | Gerritz et al. |
| 2007/0088036 A1 | 4/2007 | Zhang et al. |
| 2007/0142634 A1 | 6/2007 | Barrow et al. |
| 2007/0232679 A1 | 10/2007 | Boy et al. |

FOREIGN PATENT DOCUMENTS

| WO | WO 2006/002004 A1 | 1/2006 |
| WO | WO 2007015157 A2 * | 2/2007 |

OTHER PUBLICATIONS

Supplementary European Search Report for EP 0886 2961, dated Mar. 17, 2011; 5 pages.
Evin, G.; et. al.; "BACE inhibitors as potential therapeutics for Azheimer's disease"; Recent Patents on CNS Drug Discovery; vol. 2, No. 3; Nov. 2007; pp. 188-199.
Written Opinion for International Application No. PCT/US08/13550 mailed Feb. 20, 2010, 3 pages.
International Search Report for International Application No. PCT/US08/13550; mailed Feb. 20, 2009; 1 page.

* cited by examiner

*Primary Examiner* — Kamal Saeed
*Assistant Examiner* — Nyeemah A Grazier
(74) *Attorney, Agent, or Firm* — Keith D. MacMillan; Gerard M. Devlin

(57) ABSTRACT

The present invention is directed to 3,4-substituted pyrrolidine compounds of formula (I) which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

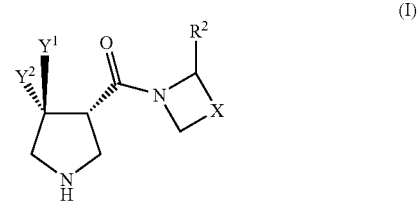

(I)

14 Claims, No Drawings

3,4-SUBSTITUTED PYRROLIDINE BETA-SECRETASE INHIBITORS FOR THE TREATMENT OF ALZHEIMER'S DISEASE

CROSS REFERENCE TO RELATED APPLICATIONS

This application is the national stage application under 35 U.S.C. 371 of International Patent Application No.: PCT/US2008/013550, filed in the U.S. Receiving Office on Dec. 10, 2008, which claims the benefit of U.S. Provisional Application No. 61/007,782, filed Dec. 14, 2007. Each of the aforementioned PCT and Provisional applications is incorporated by reference in its entirety as if fully set forth herein.

FIELD OF THE INVENTION

The invention is directed to 3,4-substituted pyrrolidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a function of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β-amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds of general formula (I)

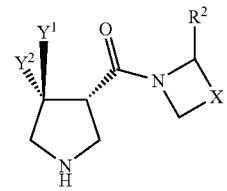

and pharmaceutically acceptable salts thereof, which are useful as inhibitors of the β-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to 3,4-substituted pyrrolidine compounds represented by general formula (I)

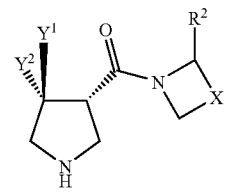

$Y^1$ is phenyl, which is optionally substituted with one or more
  (a) —$C_{1-6}$alkyl,
  (b) —$C_{1-6}$alkyl-$C_{3-6}$cycloalkyl,
  (c) —$C_{6-10}$aryl,
  (d) halogen,
  (e) —O—$C_{1-6}$alkyl,
  (f) —CN,
  (g) a heterocyclic group having 4 to 8 ring atoms, wherein one ring atom is a heteroatom selected from the group consisting of nitrogen, sulfur or oxygen, and
  (h) heteroaryl,
  and wherein said alkyl, aryl, cycloalkyl, heterocyclic, aryl or heteroaryl moiety is optionally substituted with one or more
    (i) halo,
    (ii) —OH,
    (iii) —CN,
    (iv) —$C_{1-6}$ alkyl,
    (v) —$C_{2-6}$ alkenyl,
    (vi) —$C_{3-6}$ cycloalkyl,
    (vii) —O—$C_{1-6}$ alkyl,
    (viii) —O—$(CH_2)_p$-aryl,
    (ix) aryl,
    (x) heteroaryl,
    (xi) —$NR^{6A}R^{6B}$, (xii) —C(=O)—R$^{6C}$,
(xiii) —C(=O)—NR$^{6A}$R$^{6B}$,
(xiv) —NR$^{6A}$(C=O)R$^{6B}$,
(xiv) —C(=O)—OR$^{6C}$,
(xv) —NSO$_2$R$^{6A}$R$^{6B}$,
(xvi) —SO$_2$—R$^{6C}$,
(xvii) —(SO$_2$)NR$^{6A}$R$^{6B}$,
wherein R$^{6A}$ and R$^{6B}$ are selected from the group consisting of
  (I) hydrogen,
  (II) —C$_{1-6}$ alkyl,
  (III) —C$_{1-6}$ cycloalkyl,
or R$^{6A}$ and R$^{6B}$ are linked together with the nitrogen to which they are both attached to form a 2-6 membered carbocyclic ring, wherein one or two of the ring carbon atoms is replaced by a nitrogen, oxygen or sulfur, and R$^{6C}$ is selected from the group consisting of
  (I) hydrogen,
  (II) —C$_{1-6}$ alkyl, and
  (III) —C$_{3-6}$ cycloalkyl;
Y$^2$ is hydrogen or methyl;
R$^2$ is selected from the group consisting of
  (1) hydrogen
  (2) C$_{1-6}$alkyl,
  (3) —C$_{1-6}$alkyl-C$_{3-6}$cycloalkyl,
  (4) —(CH$_2$)$_m$aryl,
  (5) heteroaryl,
  (6) —O—C$_{1-6}$ alkyl,
  (7) —C(=O)—OR$^{6C}$, and
  (8) a heterocyclic group having 4 to 8 ring atoms, wherein one ring atom is a heteroatom selected from the group consisting of nitrogen, sulfur or oxygen, and wherein said alkyl, aryl, cycloalkyl, heterocyclic or heteroaryl R$^2$ moiety is optionally substituted with one or more
    (a) halo,
    (b) —OH,
    (c) —CN,
    (d) —C$_{1-6}$ alkyl
    (e) —C$_{3-6}$ cycloalkyl,
    (f) —O—C$_{1-6}$ alkyl,
    (g) —O—CH$_2$-aryl,
    (h) aryl,
    (i) heteroaryl,
    (j) —NR$^{6A}$R$^{6B}$,
    (k) —NR$^{6A}$C(=O)R$^{6B}$,
    (l) a heterocyclic group having 4 to 8 ring atoms, wherein one ring atom is a heteroatom selected from the group consisting of nitrogen, sulfur and oxygen,
    (m) —SO$_2$C$_{1-3}$ alkyl,
    (n) —SO$_2$NR$^{6A}$R$^{6B}$,
    (o) —CONR$^{6A}$R$^{6B}$, and
    (p) a heterocyclic group having 4 to 8 ring atoms, wherein one ring atom is a heteroatom selected from the group consisting of nitrogen, sulfur and oxygen;
X is selected from the group consisting of
  (1) —CR$^5$R$^6$—O—CR$^7$R$^8$—
  (2) —CR$^5$R$^6$CR$^7$R$^8$—O—R$^9$R$^{10}$—
  (3) —CR$^5$R$^6$—
  (4) —CR$^5$R$^6$CR$^7$R$^8$—
  (5) —CR$^5$R$^6$CR$^7$R$^8$CR$^9$R$^{10}$—
  (6) —CR$^5$=CR$^6$CR$^7$R$^8$—
  (7) —CR$^5$R$^6$CR$^7$R$^8$CR$^9$R$^{10}$CR$^{11}$R$^{12}$—;
R$^3$ and R$^4$ are independently selected from the group consisting of:
  (1) hydrogen,
  (2) aryl,
  (3) heteroaryl,
  (4) C$_{1-6}$alkyl,
  (5) C$_{2-6}$alkylene,
  (6) OH
  (7) —C$_{3-7}$ cycloalkyl,
  (8) —(CH$_2$)$_m$aryl,
  wherein said alkyl, cycloalkyl, aryl or heteroaryl R$^3$ and R$^4$ moiety is optionally substituted with one or more
    (a) halo,
    (b) —C$_{1-6}$ alkyl, wherein said alkyl is optionally substituted with one or more halogen,
    (c) —O—C$_{1-6}$ alkyl, and
    (d) —NO$_2$,
  or R$^3$ and R$^4$ are linked together to form cyclic group of 3-6 ring carbon atoms, wherein one or two of the ring carbon atoms is replaced by an oxygen, nitrogen or sulfur;
R$^5$, R$^6$, R$^7$, R$^8$, R$^9$, R$^{10}$, R$^{11}$ and R$^{12}$ are independently selected from the group consisting of:
  (1) hydrogen,
  (2) C$_{1-6}$alkyl,
  (3) OH
  (4) —(CH$_2$)$_m$aryl
  wherein said alkyl or aryl moiety is optionally substituted with one or more
    (a) halo,
    (b) —C$_{1-6}$ alkyl,
    (c) —O—C$_{1-6}$ alkyl, and
    (d) -aryl,
    wherein said wherein said alky or aryl is optionally substituted with one or more halo,
  or R$^5$ and R$^6$, or R$^7$ and R$^8$, or R$^9$ and R$^{10}$, or R$^{11}$ and R$^{12}$ are linked together to form an aromatic or non-aromatic spirocyclic group of 5-10 ring carbon atoms, wherein one or two of the ring carbon atoms is replaced by an oxygen, nitrogen or sulfur,
  or R$^5$ and R$^6$, and R$^7$ and R$^8$, are linked together to form to form a fused aromatic or non-aromatic cyclic group of 5-10 ring carbon atoms, wherein one or two of the ring carbon atoms is replaced by an oxygen, nitrogen or sulfur,
  or R$^2$ and R$^5$ are linked together to form to form a fused aromatic or non-aromatic cyclic group of 5-10 ring carbon atoms, wherein one or two of the ring carbon atoms is replaced by an oxygen, nitrogen or sulfur;
m is 0, 1 or 2;
n is 0, 1, 2 or 3;
p is 0 or 1;
and pharmaceutically acceptable salts thereof.

In one embodiment, Y$^1$ is phenyl, which is substituted by one or more
  (1) —C$_{1-6}$alkyl, wherein said alkyl is optionally substituted with one or more fluoro,
  (2) halogen, and
  (3) —O—C$_{1-6}$alkyl, wherein said alkyl is optionally substituted with one or more fluoro.

In an alternative embodiment, Y$^1$ is phenyl, which is substituted by one or more phenyl, wherein said phenyl is optionally substituted with one or more
  (a) halo,
  (b) —OH,
  (c) —CN,
  (d) —C$_{1-6}$ alkyl,
  (e) —C$_{2-6}$ alkenyl,
  (f) —C$_{3-6}$ cycloalkyl,
  (g) —O—C$_{1-6}$ alkyl,
  (h) —O—(CH$_2$)$_p$-aryl,
  (i) aryl,
  (j) heteroaryl, (k) —NR$^{6A}$R$^{6B}$,
(l) —C(=O)—R$^{6C}$,
(m) —C(=O)—NR$^{6A}$R$^{6B}$,
(n) —NR$^{6A}$(C=O)R$^{6B}$,
(o) —C(=O)—OR$^{6C}$,
(p) —NSO$_2$R$^{6A}$R$^{6B}$,
(q) —SO$_2$—R$^{6C}$, and
(r) —(SO$_2$)NR$^{6A}$R$^{6B}$.

Exemplary Y$^1$ phenyl groups include 2-methylphenyl, 2-bromophenyl, 4'-ethoxybiphenyl-2-yl, 2-chlorophenyl, 2-methoxyphenyl, biphenyl-2-yl, 2-(1-methyl-1H-pyrazol-4-yl), 2'-fluorobiphenyl, 4'-carbonitrile-biphenyl-2-yl, 3'-carbonitrile-biphenyl-2-yl, 3'-trifluoromethyl-biphenyl-2-yl, 3'-methanesulfonamide-biphenyl-2-yl, 2-(2,3-dihydro-1,4-benzodioxin-6-yl)phenyl, 4'-fluoro-2'-methylbiphenyl-2-ylk, 2-(3-thienyl)-phenyl, (2'-benzyloxy)biphenyl-2-yl, 4'-isobutyl-biphenyl-2-yl, 1-methyl-1H-indol-2-phenyl, 4'-methylsulfonyl-biphenyl-2-yl, 4'-(morpholin-4-ylcarbonyl)biphenyl-2-yl, 4'-(N-cyclopropyl-carboxamide)-biphenyl-2-yl, 4'-N-methylamine-biphenyl-2-yl, 4'-oxyacetonitrile-biphenyl-2-yl, 2-(6-chloropyridin-3-yl)-phenyl, 2-(3,5-dimethylisoxazol-4-yl)phenyl, 2-(3-furyl)phenyl, 2-(pyridin-2-ol)-phenyl, 2-(1-methylprop-1-en-1-yl)phenyl, biphenyl-4'-ol-2-yl, 4'-methylbiphenyl-2-yl, 4'-fluorobiphenyl-2-yl, 4'-ethylcarboxylate-biphenyl-2-yl, 4'-acetamide-biphenyl-2-yl, 2-(6-morpholin-4-ylpyridin-3-yl)phenyl, 4'-(pyrrolidin-1-ylsulfonyl)biphenyl-2-yl, 4'-tertbutylbiphenyl-2-yl, 3'-propoxybiphenyl-2-yl, 3'-isopropoxybiphenyl-2-yl, 4'-isopropoxybiphenyl-2-yl, 4'-propoxybiphenyl-2-yl, 4'-(trifluoromethyl)biphenyl-2-yl, 2'-methyl-4'-propoxybiphenyl-2-yl, 4'-phenoxybiphenyl-2-yl, 2'-fluoro-1,1':4',1"-terphenyl-2-yl, 2-[(1E)-prop-1-en-1-yl]phenyl, 2-allylphenyl, 2-(1H-pyrrol-2-yl)-phenyl, 4-pyridin-phenyl-2-yl, 5-pyrimidin-phenyl-2-yl, 3-pyridin-phenyl-2-yl, 5-(2-chloro)-pyridin-phenyl-2-yl, 2-(1H-pyrazol-4-yl) phenyl, 2-(1-methyl-1H-pyrazol-4-yl) phenyl, 2-(1-isobutyl-1H-pyrazol-4-yl) phenyl, 2-(1-(3-methylbutyl)-1 H-pyrazol-4-yl) phenyl, 2-(1-propyl-1H-pyrazol-4-yl)phenyl, 2-cyclohex-1-en-1-ylphenyl, 2-cycloproplyphenyl, 2-(2-thienyl)phenyl, 1-benzofuran-2-yl-phenyl, 3-bromophenyl, 2-cyanophenyl, 3-(methoxymethyl)phenyl, 3-cyanophenyl, 3-(2-methoxyethyl)phenyl and 4-(N,N-dimethyl)-phenyl.

In one embodiment, Y$^2$ is hydrogen.

In one embodiment, R$^2$ is selected from the group consisting of:
(1) phenyl, and
(2) benzyl.

In one embodiment, X is selected from the group consisting of
(1) —CR$^5$R$^6$—O—CR$^7$R$^8$—,
(2) —CR$^5$R$^6$CR$^7$R$^8$—O—R$^9$R$^{10}$—,
(3) —CR$^5$R$^6$CR$^7$R$^8$—, and
(4) —CR$^5$R$^6$CR$^7$R$^8$CR$^9$R$^{10}$—.

Suitable R$^{1A}$ and R$^{1B}$ alkyl groups include methyl, trifluoromethyl, difluoromethyl and ethyl.

Suitable R$^{1A}$ and R$^{1B}$ alkenyl groups include propenyl.

Suitable R$^{1A}$ and R$^{1B}$ halo groups include fluoro, chloro, bromo and iodo.

Suitable R$^{1A}$ and R$^{1B}$ alkoxy groups include methoxy and ethoxy.

Suitable R$^{1A}$ and R$^{1B}$ heteroaryl groups include tetrazolyl, benzodioxan, thienyl, furyl, indolyl, pyridyl, isoxazolyl and pyridinyl, all of which are optionally substituted, as described above.

Exemplary R$^2$ alkyl groups include methyl, fluoromethyl, ethyl and isopropyl.

Exemplary R$^2$ cycloalkyl groups include cyclopropyl.

Exemplary R$^2$ aryl groups include phenyl, 4-methoxyphenyl, 3,5-dichlorophenyl and 4-chlorophenyl.

Exemplary R$^2$ alkylaryl groups include benzyl and phenylethyl.

Exemplary R$^7$ and R$^8$ groups include phenyl.

The invention is also directed to methods of treating mammals for diseases in which the β-secretase enzyme is involved, such as Alzheimer's disease, by administering a therapeutically effective amount of a compound of any of the embodiments of formula (I).

The invention is also directed to pharmaceutical compositions which include an effective amount of a compound of any of the embodiments of formula (I) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formula (I) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formula (I).

In another embodiment, the invention is directed to methods of inhibiting BACE2 enzyme activity, by administering a therapeutically effective amount of a compound of any of the embodiments of formula (I).

The invention is also directed to a method for the manufacture of a medicament or a composition for treating Alzheimer's Disease in humans, comprising combining a compound of any of the embodiments of formula (I) or a pharmaceutically acceptable salt thereof, with a pharmaceutical carrier or diluent.

Within the genus of compounds of formula (I), there is a sub-genus of compounds of formula (II):

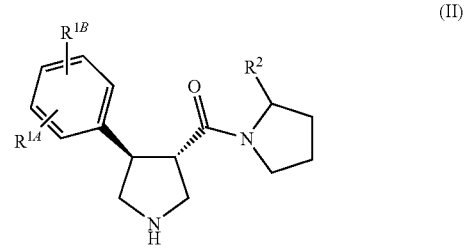

(II)

wherein R$^{1A}$ and R$^{1B}$ are selected from the group consisting of
(a) —C$_{1-6}$alkyl,
(b) —C$_{1-6}$alkyl-C$_{3-6}$cycloalkyl,
(c) —C$_{6-10}$aryl,
(d) halogen,
(e) —O—C$_{1-6}$alkyl,
(f) —CN,
(g) a heterocyclic group having 4 to 8 ring atoms, wherein one ring atom is a heteroatom selected from the group consisting of nitrogen, sulfur or oxygen, and
(h) heteroaryl,
and wherein said alkyl, aryl, cycloalkyl, heterocyclic, aryl or heteroaryl moiety is optionally substituted with one or more
(i) halo,
(ii) —OH,
(iii) —CN, (iv) —$C_{1-6}$ alkyl,
(v) —$C_{2-6}$ alkenyl,
(vi) —$C_{3-6}$ cycloalkyl,
(vii) —O—$C_{1-6}$ alkyl,
(viii) —O—$(CH_2)_p$-aryl,
(ix) aryl,
(x) heteroaryl,
(xi) —$NR^{6A}R^{6B}$,
(xii) —C(=O)—$R^{6C}$,
(xiii) —C(=O)—$NR^{6A}R^{6B}$,
(xiv) —$NR^{6A}$(C=O)$R^{6B}$,
(xiv) —C(=O)—$OR^{6C}$,
(xv) —$NSO_2R^{6A}R^{6B}$,
(xvi) —$SO_2$—$R^{6C}$,
(xvii) —$(SO_2)NR^{6A}R^{6B}$,
wherein $R^{6A}$ and $R^{6B}$ are selected from the group consisting of
(I) hydrogen,
(II) —$C_{1-6}$ alkyl,
(III) —$C_{3-6}$ cycloalkyl,
or $R^{6A}$ and $R^{6B}$ are linked together with the nitrogen to which they are both attached to form a 2-6 membered carbocyclic ring, wherein one or two of the ring carbon atoms is replaced by a nitrogen, oxygen or sulfur, and $R^{6C}$ is selected from the group consisting of
(I) hydrogen,
(II) —$C_{1-6}$ alkyl, and
(III) —$C_{3-6}$ cycloalkyl, Within the genus of compounds of formula (I), there is a sub-genus of compounds of formula (III):

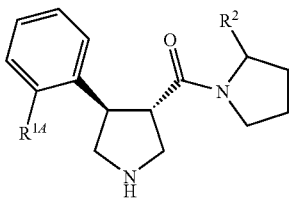

(III)

wherein $R^{1A}$ is selected from the group consisting of
(a) —$C_{1-6}$alkyl,
(b) —$C_{1-6}$alkyl-$C_{3-6}$cycloalkyl,
(c) —$C_{6-10}$aryl,
(d) halogen,
(e) —O—$C_{1-6}$alkyl,
(f) —CN,
(g) a heterocyclic group having 4 to 8 ring atoms, wherein one ring atom is a heteroatom selected from the group consisting of nitrogen, sulfur or oxygen, and
(h) heteroaryl,
and wherein said alkyl, aryl, cycloalkyl, heterocyclic, aryl or heteroaryl moiety is optionally substituted with one or more
(i) halo,
(ii) —OH,
(iii) —CN,
(iv) —$C_{1-6}$ alkyl,
(v) —$C_{2-6}$ alkenyl,
(vi) —$C_{3-6}$ cycloalkyl,
(vii) —O—$C_{1-6}$ alkyl,
(viii) —O—$(CH_2)_p$-aryl,
(ix) aryl,
(x) heteroaryl,
(xi) —$NR^{6A}R^{6B}$,
(xii) —C(=O)—$R^{6C}$,
(xiii) —C(=O)—$NR^{6A}R^{6B}$,
(xiv) —$NR^{6A}$(C=O)$R^{6B}$,
(xiv) —C(=O)—$OR^{6C}$,
(xv) —$NSO_2R^{6A}R^{6B}$,
(xvi) —$SO_2$—$R^{6C}$,
(xvii) —$(SO_2)NR^{6A}R^{6B}$,
wherein $R^{6A}$ and $R^{6B}$ are selected from the group consisting of
(I) hydrogen,
(II) —$C_{1-6}$ alkyl,
(III) —$C_{3-6}$ cycloalkyl,
or $R^{6A}$ and $R^{6B}$ are linked together with the nitrogen to which they are both attached to form a 2-6 membered carbocyclic ring, wherein one or two of the ring carbon atoms is replaced by a nitrogen, oxygen or sulfur, and $R^{6C}$ is selected from the group consisting of
(I) hydrogen,
(II) —$C_{1-6}$ alkyl, and
(III) —$C_{3-6}$ cycloalkyl, In particular embodiment of compounds of formula (III), R1A is phenyl, which is optionally substituted as described above.

Within the genus of compounds of formula (I), there is a sub-genus of compounds of formula (IV):

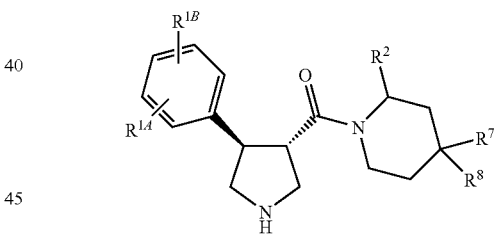

(IV)

wherein $R^{1A}$, $R^{1B}$, $R^2$, $R^7$ and $R^8$ are described above, and pharmaceutically acceptable salts thereof.

Within the genus of compounds of formula (I), there is a sub-genus of compounds of formula (V):

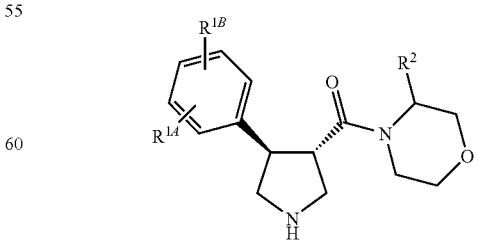

(V)

wherein $R^{1A}$, $R^{1B}$ and $R^2$ are described above, and pharmaceutically acceptable salts thereof.

Within the genus of compounds of formula (I), there is a sub-genus of compounds of formula (VI):

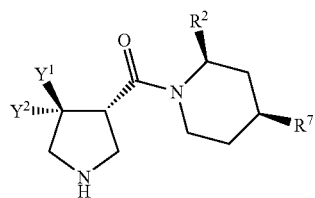

(VI)

wherein $Y^1$, $Y^2$, $R^2$ and $R^7$ are described above, and pharmaceutically acceptable salts thereof.

In another embodiment, the invention is directed to compounds of Examples 1-138 as described herein, or pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "alkylene" means an alkyl group as defined above, having two radicals.

The term "$C_0$ alkyl" or "$C_0$ alkylene" for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

The term "alkynylene" means an alkenyl group as defined above, having two radicals.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Suitable alkynyl groups for use in the invention are $C_{2-6}$ alkynyl groups, having from two to six carbon atoms. Exemplary alkynyl groups include ethynyl and propynyl.

The term "alkenylene" refers to an alkynyl group as defined above, having two radicals.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as Spiro fused ring systems.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

The term "cycloalkylene" refers to a cycloalkly group as defined above, having two radicals.

As used herein, the term "cycloalkenyl," by itself or as part of another substituent, means a saturated cyclic hydrocarbon radical having a single C=C double bond and the number of carbon atoms designated (e.g., $C_{3-12}$ cycloalkenyl means a cycloalkenyl group having from three to twelve carbon atoms).

Suitable cycloalkenyl groups for use in the invention are monocyclic $C_{3-8}$ cycloalkenyl groups, having from three to eight carbon atoms. Exemplary monocyclic cycloalkenyl groups include cyclopropenyl, cyclobutenyl, cyclopentenyl, cyclohexenyl and the like.

The term "cycloalkenylene" refers to a "cycloalkenyl" group as defined above having two radicals.

As used herein, the term "heterocyclic," by itself or as part of another substituent, means a cycloalkyl group as defined above, in which one or more of the ring carbon atoms is replaced with a heteroatom (such as N or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. In certain embodiments, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of formula (I) have at least one asymmetric center. Additional asymmetric centers may be present depending upon the nature of the various substituents on the molecule.

Compounds with asymmetric centers give rise to enantiomers (optical isomers), diastereomers (configurational isomers) or both. All of the possible enantiomers and diastereomers in mixtures (as pure or partially purified compounds) are included within the scope of formula (I)

Compounds described herein may contain one or more double bonds, and may thus give rise to cis/trans isomers as well as other configurational isomers. The compounds of formula (I) include all such possible isomers as well as mixtures of such isomers.

Formula (I) is shown above without a definite stereochemistry at certain positions. Figure (I) as depicted includes all stereoisomers of formula (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The term "substantially pure" means that the isolated material is at least 90% pure, as assayed by analytical techniques known in the art. In one embodiment, the isolated material is at least 95% pure. In another embodiment, the isolated material is at least 99% pure The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particular salts are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular salts are the citric, hydrobromic, hydrochloric, trifluoroacetic, maleic, phosphoric, sulfuric, fumaric, and tartaric acids.

The present invention is directed to the use of the compounds of formulas (I) to (III) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α 5 receptor ligands; $GABA_B$ receptor ligands; potassium channel blockers; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In certain embodiments, each tablet contains from about 0.1 mg to about 500 mg of the active ingredient and each cachet or capsule contains from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. Suitable carriers include cocoa butter and other materials commonly used in the art.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise-undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant. By "pharmaceutically acceptable" it is meant the carrier, diluent or excipient must be compatible with the other ingredients of the formulation and not deleterious to the recipient thereof.

Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention to obtain a desired pharmacologic and/or physiologic effect. The effect may be prophylactic in terms of completely or partially preventing a disease or symptom thereof, and/or may be therapeutic in terms of a partial or complete cure for a disease and/or adverse affect attributable to the disease. Treatment includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The terms "individual," "subject," and "patient," used interchangeably herein, refer to a mammal, including, but not limited to, murines, simians, humans, mammalian farm animals, mammalian sport animals, and mammalian pets.

The compositions containing compounds of the invention may conveniently be presented in unit dosage form and may be prepared by any of the methods well known in the art of pharmacy.

The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight. For example, the compounds may be given as a single daily dose or in divided doses two to six times a day, or in sustained release form. The total daily dosage is from about 1.0 mg to about 2000 mg (for example, from about 0.1 mg to about 20 mg per kg of body weight). In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, for example once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is approximated at 50 μM. A typical reaction contains approximately 0.6 nM enzyme, 0.25 μM of the substrate, and buffer (50 mM Pipes, pH 6.5, 0.1 mg/ml BSA, 0.2% CHAPS, 15 mM EDTA and 1 mM deferoxamine) in a total reaction volume of 100 μl. The reaction proceeds for 1-2 hrs and is then stopped by the addition of 150 μL of a quench cocktail solution (25 μl M Tris-HCl, pH 8.0, 50 μl INC buffer (2% BSA, 0.2% Tween-20 and 0.05% sodium azide diluted in Phosphate buffered saline (PBS) plus 75 μL PBS), containing Streptavidin coated magnetic beads and ruthenylated antibody which specifically recognizes the C-terminal residue of the product. The samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 10 concentrations of inhibitors are prepared starting from 200 μM with three fold series dilution. Solutions of the inhibitor in DMSO are included in the reaction mixture (final DMSO concentration is 10%). All experiments are conducted at it using the standard reaction conditions described above. To determine the $IC_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 200 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Exemplary $IC_{50}$ values for representative compounds of the invention (as described in the following Examples) are provided below in Table 1.

TABLE 1

| Example | $IC_{50}$(μM) |
| --- | --- |
| 8 | 67 |
| 12 | 18 |
| 38 | 19 |
| 64 | 3 |
| 75 | 0.85 |
| 76 | 3.5 |
| 79 | 1.8 |
| 83 | 0.38 |
| 137 | 28 |
| 139 | 0.15 |

General scheme A outlines a method for preparing compounds having different combination of aryl and amide substituents on the pryyolidine ring. In this method, the appropriate cinnamate ester 1 is reacted with N-benzyl-N-(methoxymethyl)-trimethylsilylmethyl amine, as an azomethine ylide precursor, to provide the trans 3,4-pyrrolidine 2. The ester is hydrolyzed and coupled under standard conditions with a suitable amine. Hydrogenative deprotection of the benzyl amine yields the target products 5.

SCHEME A

SCHEME B

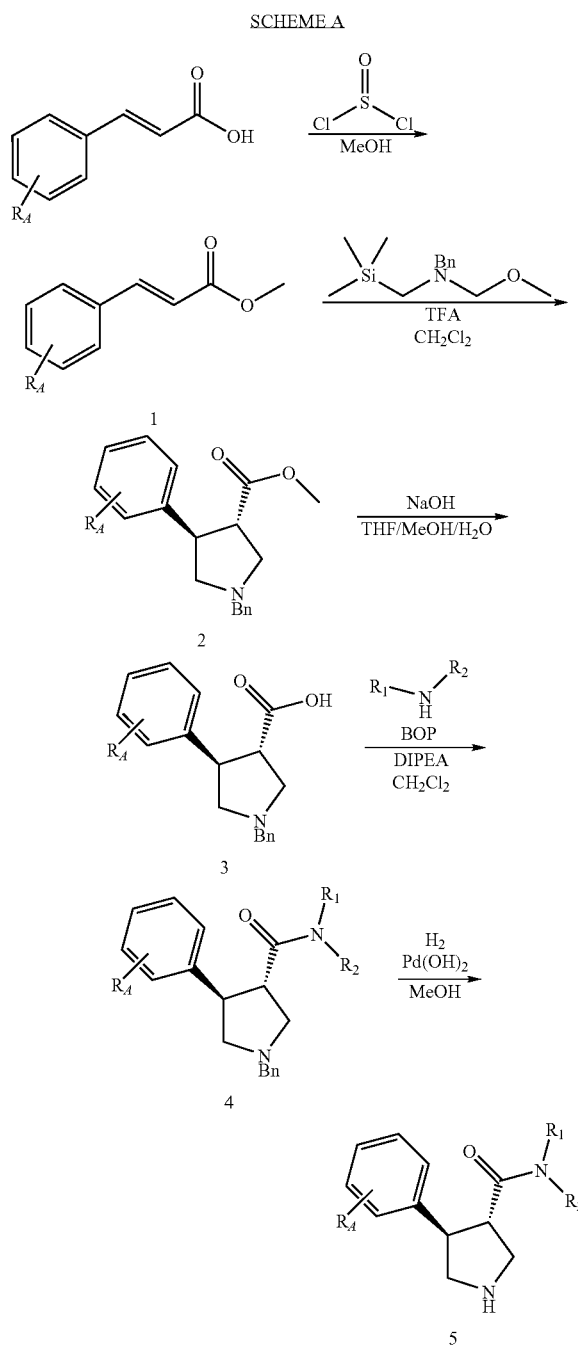

General Scheme B outlines a method for preparing compounds that have an RA or N(R1)(R2) that is not compatible with hydrogenation conditions. In this method, the appropriate cinnamate ester 6 is reacted with N-benzyl-N-(methoxymethyl)-trimethylsilylmethyl amine as an azomethine ylide precursor to provide the trans pyrrolidine 7. The benzyl protecting group is then exchanged for a t-butoxycarbonyl by sequential treatment with 1-chloroethyl chloroformate, then methanol, and finally BOC anhydride to provide the BOC-protected pyrrolidine. The ester is hydrolyzed and coupled under standard conditions with a suitable amine. TFA mediated deprotection of the t-butyl carbamate yields the desired product 11.

General Scheme C outlines a method for preparing substituted aryl modifications to the pyrroline template. In this method the appropriate aryl halide 12 is subjected to palladium catalyzed cross-coupling condition to produce the target compounds 13.

SCHEME C

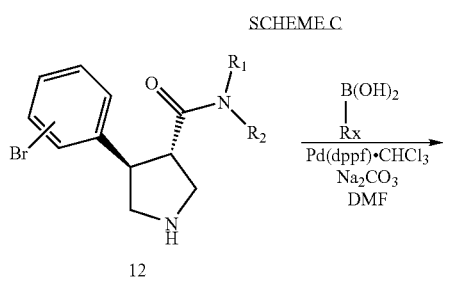

12

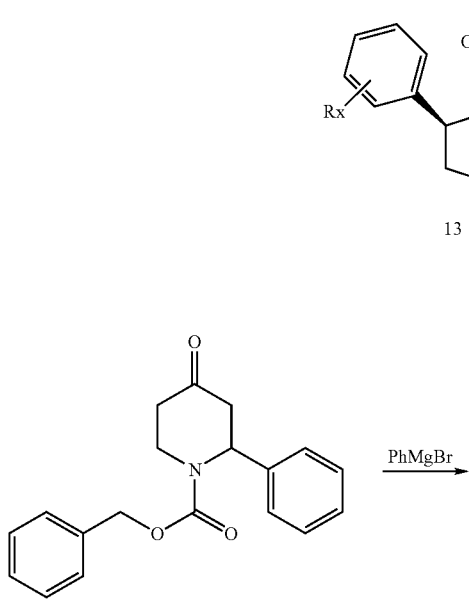

13

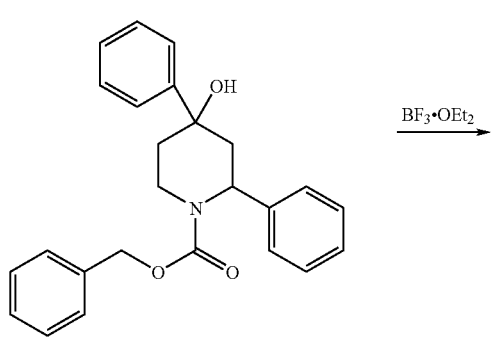

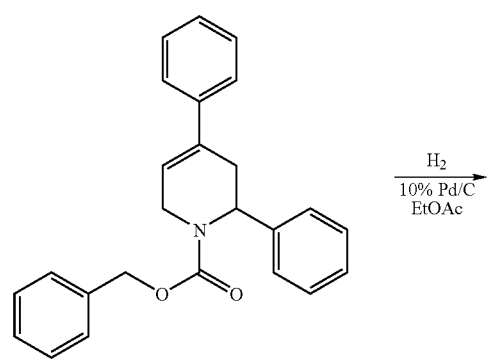

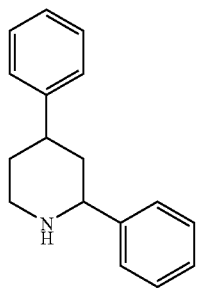

Benzyl-4-oxo-2-phenylpiperidine-1-carboxylate (1.64 g, 5.30 mmol) in THF (27 ml) was cooled to −78° C. and phenylmagnesium bromide (6.36 ml, 6.36 mmol) was added. The ice bath was removed and the solution stirred at room temperature for 2 h. Concentrate, dilute with EtOAc and wash twice with water. The organics were dried over MgSO$_4$, concentrated, and purified on silica gel eluted using 30% EtOAc to afford 1.02 g of benzyl 4-hydroxy-2,4-diphenylpiperidine-1-carboxylate.

$^1$H NMR (CDCl$_3$) δ 7.47-7.23 (m, 15H), 5.65 (br s, 1H), 5.20 (s, 2H), 4.38-4.30 (m, 1H), 3.60-3.51 (m, 1H), 2.59-2.47 (m, 2H), 2.14-2.05 (m, 1H), 1.78-1.71 (m, 1H), 1.37 (s, 1H).

A solution of BF$_3$.OEt$_2$ (1 ml, 7.9 mmol) in CH$_2$Cl$_2$ (5 ml) was added to a stirred solution of benzyl 4-hydroxy-2,4-diphenylpiperidine-1-carboxylate (1.0 g, 2.6 mmol) in CH$_2$Cl$_2$ (50 ml) at 0° C. The mixture was stirred at room temperature for 15 minutes. Saturated sodium bicarbonate (10 ml) was then added. The solution was concentrated and extracted three times EtOAc, then washed with brine. The organics were combined, dried, and concentrated. The crude product was not purified.

$^1$H NMR (CDCl$_3$) δ 7.47-7.23 (m, 15H), 6.26-5.73 (m, 2H), 5.24-5.10 (m, 2H), 4.57-4.20 (m, 1H), 3.60-3.00 (m, 1H), 2.80-2.43 (m, 1H).

To Benzyl 2,4-diphenyl-3,6-dihydropyridine-1(2H)-carboxylate (0.39 g, 1.06 mmol) in EtOAc (25 ml) was added Pd/C (0.186 g, 1.75 mmol) and hydrogenated with a balloon. Filter through celite after 4 hours and concentrate. The amine was purified on reverse phase HPLC.

$^1$H NMR (CDCl$_3$) δ 7.46-7.17 (m, 15H), 3.81-3.75 (m, 1H), 3.39-3.33 (m, 1H), 3.04-2.95 (m, 1H), 2.84-2.76 (m, 1H), 2.05-1.88 (m, 2H), 1.82-1.67 (m, 3H).

Intermediate II: 2'-phenyl-spiro[1H]Indene-1,4'-piperidine

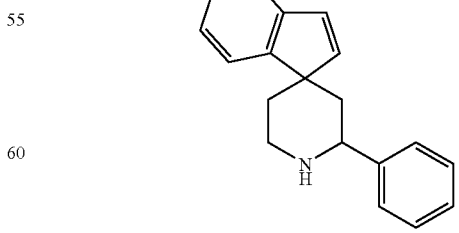

2'-phenyl-spiro[1H]Indene-1,4'-piperidine was prepared according to the procedure described by M. G. Bock et. al. (U.S. Pat. No. 5,756,504, 1998)

Intermediate III: methyl(2E)-3-(2-methylphenyl)acrylate

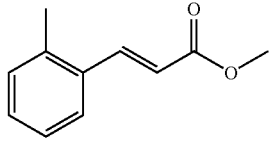

To 2-Methylcinnamic acid (5.68 g, 35 mmol) in MeOH (175 ml) was added thionyl chloride (2.55 ml, 35.0 mmol) dropwise. The resulting solution was stirred for 10 hours at 60° C. The solution was cooled to room temperature and concentrated. The crude ester was dissolved in $CH_2Cl_2$ and washed twice with saturated $NaHCO_3$. The organics were combined, dried, and concentrated affording 6.45 g of methyl (2E)-3-(2-methylphenyl)acrylate.

$^1$H NMR ($CDCl_3$) δ 7.98 (d, J=16 Hz, 1H), 7.56-7.53 (m, 1H), 7.28-7.19 (m, 3H), 6.36 (d, J=16 Hz, 1H), 3.81 (s, 3H), 2.44 (s, 3H).

Intermediate IV: 1-Benzyl-4-(2-methylphenyl)pyrrolidine-3-carboxylate

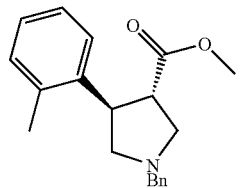

To a solution of N-benzyl-n-(methoxymethyl)-n-trimethylsilylmethylamine (1.3 ml, 5 mmol) and methyl(2E)-3-(2-methylphenyl)acrylate 1 (0.88 g, 5.00 mmol) in CH2Cl2 (20 ml) at 0° C. TFA (0.04 ml, 0.500 mmol) was added dropwise. The ice bath was removed after 15 minutes and the solution stirred for 4 hours. Dilute with $CH_2Cl_2$ and wash twice with saturated $NaHCO_3$. The organic layer was dried, concentrated, and purified on silica gel (20% EtOAc/Hexanes) affording 1.48 g of the pyrrolidine 2.

$^1$H NMR ($CDCl_3$) δ 7.44 (d, J=7.7 Hz, 1H), 7.38-7.29 (m, 4H), 7.25-7.17 (m, 2H), 7.12-7.07 (m, 2H), 3.98-3.92 (m, 1H), 3.73-3.63 (m, 5H), 3.16-3.08 (m, 2H), 2.99 (t, J=8.8 Hz 1H), 2.90-2.82 (m, 1H), 2.73-2.67 (m, 1H), 2.34 (s, 3H). LRMS (M+H)=310.03

Intermediate V: 1-Benzyl-4-(2-methylphenyl)pyrrolidine-3-carboxylic acid

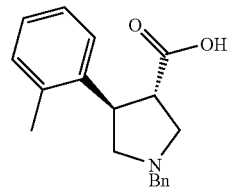

To 1-Benzyl-4-(2-methylphenyl)pyrrolidine-3-carboxylate (0.685 g, 2.214 mmol) in THF/MeOH/$H_2O$ (5 ml) was added 2N NaOH (3.32 ml, 6.64 mmol). The solution was stirred for 12 hours at room temperature and was acidified to pH1-2 with 1N HCl. The crude acid was extracted three times with EtOAc. The combined organic layers were dried over $Na_2SO_4$ and concentrated.

$^1$H NMR ($CD_3OD$) δ 7.58-7.53 (m, 2H), 7.51-7.45 (m, 4H), 7.29-7.24 (m, 1H), 7.20-7.16 (m, 2H), 4.51 (s, 2H), 4.10 (br s, 1H), 3.59-3.57 (m, 3H), 3.62-3.51 (m, 1H), 3.40 (t, J=11.5 Hz, 1H), 2.37 (s, 3H). LRMS (M+H)=296.05

Intermediate VI: 1-Benzyl-3-[(2-benzylpyrrolidin-1-yl)carbonyl]-4-(2-methylphenyl)pyrrolidine

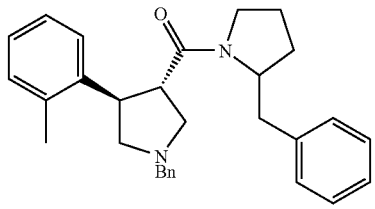

To 1-Benzyl-4-(2-methylphenyl)pyrrolidine-3-carboxylic acid (0.088 g, 0.298 mmol) in $CH_2Cl_2$ (1.490 ml) was added BOP (0.138 g, 0.313 mmol), DIPEA (0.208 ml, 1.192 mmol), and 2-benzylpyrrolidine (0.050 g, 0.313 mmol). The solution was stirred at room temperature for 4 hours. Concentrate, filter, and purify on reverse phase HPLC. HRMS (M+H) =439.2739

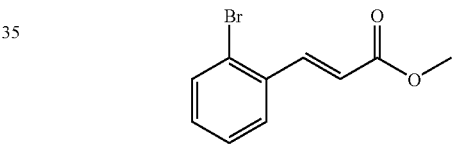

Intermediate VII

To 2-Bromocinnamic acid (10.0 g, 44.0 mmol) in MeOH (100 ml) was added thionyl chloride (3.21 ml, 44.0 mmol) dropwise. The resulting solution was stirred for 10 hours at 60° C. The solution was cooled to room temperature and concentrated. The crude ester was dissolved in $CH_2Cl_2$ and washed twice with saturated $NaHCO_3$. The organics were combined, dried, and concentrated affording 10.6 g of methyl (2E)-3-(2-bromolphenyl)acrylate.

$^1$H NMR ($CDCl_3$) δ 8.05 (d, J=16 Hz, 1H), 7.62-7.59 (m, 2H), 7.35-7.31 (m, 1H), 7.25-7.21 (m, 1H), 6.39 (d, J=16 Hz, 1H), 3.83 (s, 3H).

Intermediate VIII: Methyl 1-benzyl-4-(2-bromophenyl)pyrrolidine-3-carboxylate

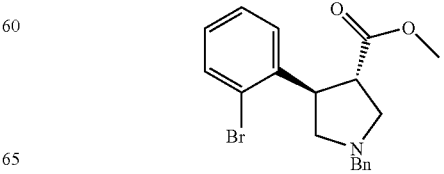

Prepared as reported for compound 2 using methyl(2E)-3-(2-bromolphenyl)acrylate.

H NMR (CDCl₃) δ 7.56-7.49 (m, 2H), 7.38-7.29 (m, 4H), 7.38-7.29 (m, 5H), 7.08-7.03 (m, 1H), 4.18-4.10 (m, 1H), 3.73-3.63 (m, 5H), 3.20-3.13 (m, 1H), 3.09-3.03 (m, 1H), 3.00-2.94 (m, 1H), 2.81-2.73 (m, 2H). LRMS (M+H)=375.9

Intermediate IX

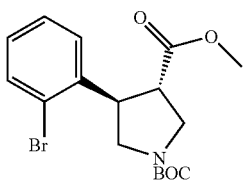

To Methyl 1-benzyl-4-(2-bromophenyl)pyrrolidine-3-carboxylate (25.5 g, 68.1 mmol) in dichloroethane (341 ml) at 0° C. under nitrogen was added 1-Chloroethyl chloroformate (8.91 ml, 82 mmol) dropwise. After 15 minutes at 0° C. the solution was warmed to room temperature and then refluxed for twelve hours. The solution was concentrated, then added MeOH (75 mL) and refluxed for and additional 3 hours. The solution was concentrated, taken up in THF (60 mL) and added DIPEA (1.260 ml, 7.21 mmol) followed by BOC-Anhydride (0.921 ml, 3.97 mmol). The solution was stirred at room temperature for ten hours. Aqueous workup and column chromatography on silica gel (20% EtOAc/Hex) afforded 18 g of 1-tert-butyl 3-methyl 4-(2-bromophenyl)pyrrolidine-1,3-dicarboxylate.

H NMR (CDCl₃) δ 7.59-7.56 (m, 1H), 7.33-7.25 (m, 2H), 7.14-7.10 (m, 1H), 4.19-4.09 (m, 1H), 3.98-3.88 (m, 1H), 3.85-3.66 (m, 5H), 3.43-3.32 (m, 1H), 3.23-3.18 (m, 1H), 1.48 (s, 9H).

Intermediate X

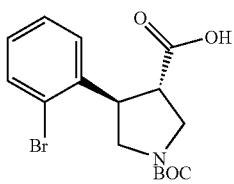

Prepared as reported for Intermediate V using 1-tert-butyl 3-methyl 4-(2-bromophenyl)pyrrolidine-1,3-dicarboxylate.

H NMR (CDCl₃) δ 7.59-7.56 (m, 1H), 7.33-7.24 (m, 2H), 7.15-7.10 (m, 1H), 4.18-4.10 (m, 1H), 3.98-3.88 (m, 1H), 3.85-3.68 (m, 2H), 3.46-3.33 (m, 1H), 3.28-3.20 (m, 1H), 1.47 (s, 9H).

Intermediate XI

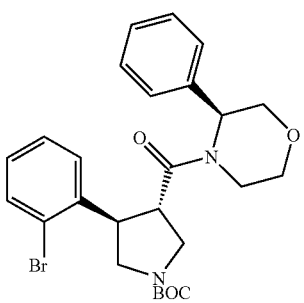

Prepared as reported for Intermediate VI using 4-(2-bromophenyl)-1-(tert-butoxycarbonyl)pyrrolidine-3-carboxylic acid.

EXAMPLE 1

2-benzyl-1-{[(3S,4R)-4-(2-methylphenyl)pyrrolidine-3-yl]carbonyl}pyrrolidine

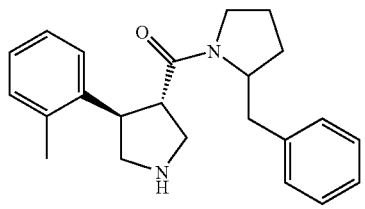 [SMILES: Cc1ccccc1[C@@H]1CNC[C@H]1C(=O)N1CCCC1Cc1ccccc1]

To 1-Benzyl-3-[(2-benzylpyrrolidin-1-yl)carbonyl]-4-(2-methylphenyl)pyrrolidine (0.1 g, 0.228 mmol) in MeOH (10 ml) was added Pearlman's Catalyst (0.05 g, 0.071 mmol) and hydrogenated with a balloon for 2 hours. Filter through celite, concentrate, and purify on reverse phase HPLC. LRMS (M+H)=349.13

EXAMPLE 2

(3S)-4-{[3S,4R]-4-(2-bromophenyl)pyrrolidine-3-yl}carbonyl}-3-phenylmorpholine

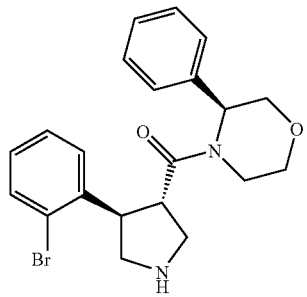 [SMILES: O=C([C@@H]1CNC[C@H]1c1ccccc1Br)N1CCOC[C@@H]1c1ccccc1]

To Tert-butyl 3-(2-bromophenyl)-4-{[(3S)-3-phenylmorpholin-4-yl]carbonyl}pyrrolidine-1-carboxlate (0.012 g, 0.023 mmol) in CH₂Cl₂ (0.466 ml) was added TFA (0.027 ml, 0.349 mmol) and stirred for 2 hours. Concentrate and convert to the HCl salt. HRMS (M+H)=415.1026.

EXAMPLE 3

(3S)-4-{[3S,4R]-4-(4'-ethoxybiphenyl-2-yl)pyrrolidin-3-yl}carbonyl}-3-phenylmorpholine

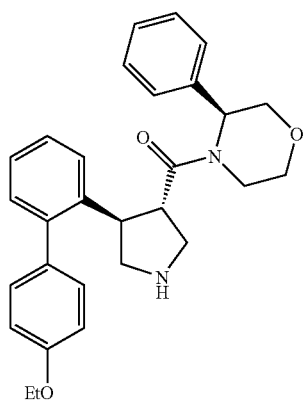 [SMILES: CCOc1ccc(-c2ccccc2[C@@H]2CNC[C@H]2C(=O)N2CCOC[C@@H]2c2ccccc2)cc1]

To (3S)-4-{[4-(2-bromophenyl)pyrrolidin-3yl]carbonyl}-3-phenylmorpholine (0.053 g, 0.128 mmol) in DMF (1.27 mL) under nitrogen was added 4-ethoxyphenylboronic acid (0.023 g, 0.140 mmol), dichloro[1,1'-bis(diphenylphosphino) ferrocene]palladium II dichloromethane adduct (0.008 g, 10.2 ummol), and 2M sodium carbonate (0.096 mL, 0.191 mmol). Heat in the microwave at 120° C. for 10 minutes. Cool to room temperature, dilute with EtOAc and filter through celite. Concentrate and purify on reverse phase Prep HPLC. The desired fractions were free based with NaHCO$_3$ and extracted twice with EtOAc. The free amine was converted to the HCl salt.

HRMS (M+H)=457.2472.

The following examples in Table 2 were prepared in a manner similar to Examples 1 to 3 above, according to the general Schemes A to D.

TABLE 2

| Ex | Structure | Chemical Name | Stereochemistry | Parent Weight | Intermed., Scheme and reference example |
|---|---|---|---|---|---|
| 4 | 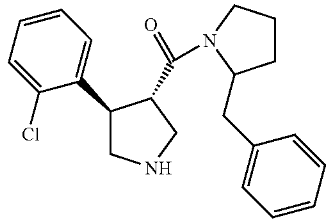 [SMILES: O=C([C@@H]1CNC[C@H]1c1ccccc1Cl)N1CCCC1Cc1ccccc1] | 2-benzyl-1-{[(3S,4R)-4-(2-chlorophenyl) pyrrolidin-3-yl] carbonyl}pyrrolidine | (S,R,R) or (R,S,S) or (S,R,S) or (R,S,R) | 368.91 | Ex2 |
| 5 | 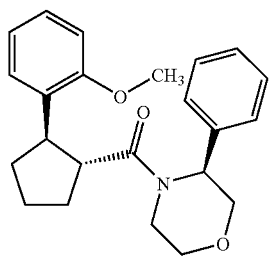 [SMILES: COc1ccccc1[C@@H]1CCC[C@H]1C(=O)N1CCOC[C@@H]1c1ccccc1] | (3S)-4-{[(3S,4R)-4-(2-methoxyphenyl) pyrrolidin-3-yl] carbonyl}-3-phenylmorpholine | R,S,R and S,R,R | 366.464 | Ex1 |
| 6 | 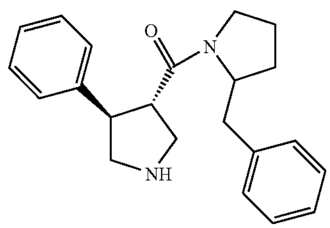 [SMILES: O=C([C@@H]1CNC[C@H]1c1ccccc1)N1CCCC1Cc1ccccc1] | 2-benzyl-1-{[(3S,4R)-4-phenylpyrrolidin-3-yl]carbonyl}pyrrolidine | (S,R,R) or (R,S,S) or (S,R,S) or (R,S,R) | 334.465 | Ex1 |
| 7 | 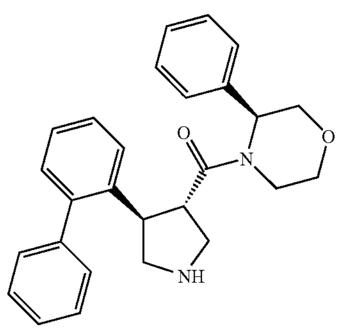 [SMILES: O=C([C@@H]1CNC[C@H]1c1ccccc1-c1ccccc1)N1CCOC[C@@H]1c1ccccc1] | (3S)-4-{[(3S,4R)-4-biphenyl-2-ylpyrrolidin-3-yl]carbonyl}-3-phenylmorpholine | R,S,R and S,R,R | 412.536 | Int. 11, Scheme C |
| 8 | 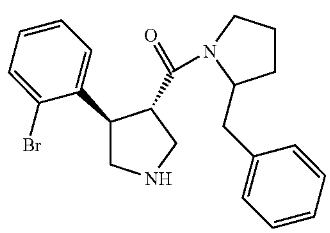 [SMILES: O=C([C@@H]1CNC[C@H]1c1ccccc1Br)N1CCCC1Cc1ccccc1] | 2-benzyl-1-{[(3S,4R)-4-(2-bromophenyl) pyrrolidin-3-yl] carbonyl}pyrrolidine | (S,R,R) or (R,S,S) or (S,R,S) or (R,S,R) | 413.361 | Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 9 | 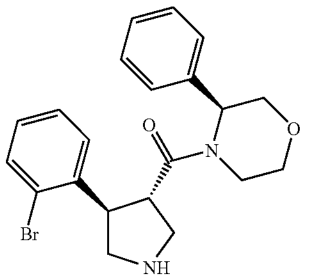 [SMILES: O=C([C@@H]1CNC[C@H]1c1ccccc1Br)N1CCOC[C@@H]1c1ccccc1] | (3s)-4-{[(3S,4R)-4-(2-bromophenyl)pyrrolidine-3-yl]carbonyl}-3-phenylmorpholine | R,S,S or S,R,S | 415.334 | Int. 9, Scheme B, Ex2 |
| 10 | 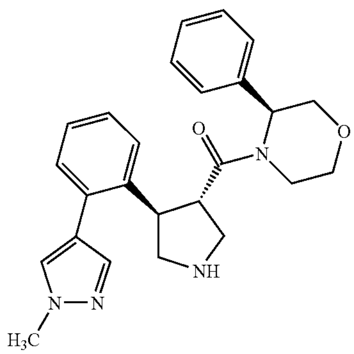 [SMILES: Cn1cc(-c2ccccc2[C@@H]2CNC[C@H]2C(=O)N2CCOC[C@@H]2c2ccccc2)cn1] | (3S)-4-({3S,4R)-4-[2-(1-methyl-1H-pyrazol-4-yl)phenyl]pyrrolidine-3-yl}carbonyl)-3-phenylmorpholine | R,S,S or S,R,S | 416.528 | Int. 11, Scheme C |
| 11 | 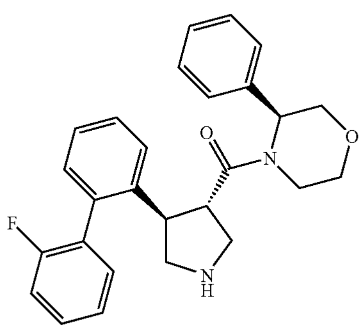 [SMILES: O=C([C@@H]1CNC[C@H]1c1ccccc1-c1ccccc1F)N1CCOC[C@@H]1c1ccccc1] | (3S)-4-({3S,4R)-4-(2'-fluorobiphenyl-2-yl)pyrrolidin-3-yl]carbonyl}-3-phenylmorpholine | R,S,S or S,R,S | 430.527 | Int. 11, Scheme C |
| 12 | 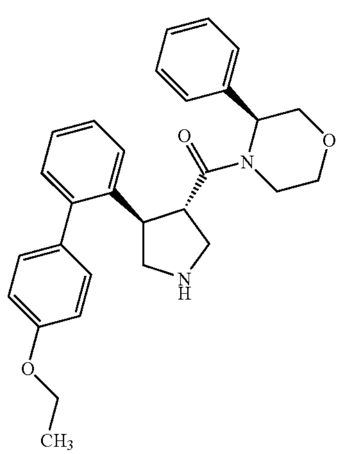 [SMILES: CCOc1ccc(-c2ccccc2[C@@H]2CNC[C@H]2C(=O)N2CCOC[C@@H]2c2ccccc2)cc1] | (3S)-4-{[3S,4R)-4-(4'-ethoxybiphenyl-2-yl)pyrrolidin-3-yl]carbonyl}-3-phenylmorpholine | R,S,S or S,R,S | 456.59 | Int. 11, Scheme C |

TABLE 2-continued

| Ex | Structure | Chemical Name | Stereochemistry | Parent Weight | Intermed., Scheme and reference example |
|---|---|---|---|---|---|
| 13 | 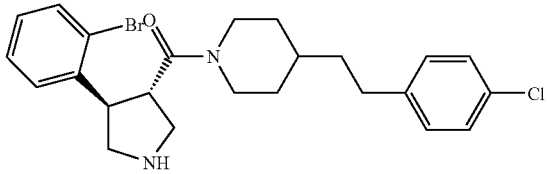 [SMILES: O=C([C@@H]1CNC[C@H]1c1ccccc1Br)N1CCC(CCc2ccc(Cl)cc2)CC1] | 1-{[3S,4R)-4-(2-bromophenyl)pyrrolidin-3-yl]carbonyl}-4-[2-(4-chlorophenyl)ethyl]piperidine | Single Diastereomer | 475.861 | Int. 9, Scheme B, Ex2 |
| 14 | 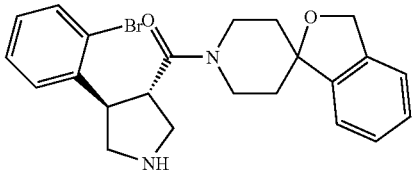 [SMILES: O=C([C@@H]1CNC[C@H]1c1ccccc1Br)N1CCC2(CC1)OCc1ccccc12] | 1'{[(3S,4R)-4-(2-bromophenyl)pyrrolidin-3-yl]carbonyl}-4-[2-(4-chlorophenyl)ethyl]piperidine | Single Diastereomer | 441.372 | Int. 9, Scheme B, Ex2 |
| 15 | 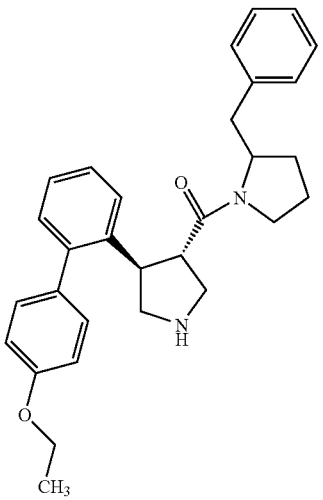 [SMILES: CCOc1ccc(-c2ccccc2[C@@H]2CNC[C@H]2C(=O)N2CCCC2Cc2ccccc2)cc1] | 2-benzyl-1-{[(3S,4R)-4-(4'ethoxybiphenyl-2-yl)pyrroliidin-3-yl]carbonyl}pyrrolidine | R,S,R or R,S,S or S,R,R or S,R,S | 454.618 | Scheme C |
| 16 | 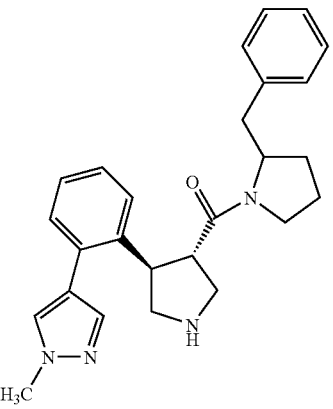 [SMILES: Cn1cc(-c2ccccc2[C@@H]2CNC[C@H]2C(=O)N2CCCC2Cc2ccccc2)cn1] | 4-(2-{(3R,4S)-4-[(2-benzylpyrrolidin-1-yl)carbonyl]pyrrolidin-3-yl}phenyl)-1-methyl-1H-pyrazole | R,S,R or R,S,S or S,R,R or R S,R,S | 414.555 | Scheme C |

TABLE 2-continued

| Ex | Structure | Chemical Name | Stereochemistry | Parent Weight | Intermed., Scheme and reference example |
|---|---|---|---|---|---|
| 17 | 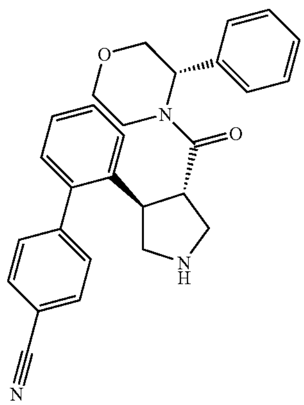 [SMILES: N#Cc1ccc(-c2ccccc2[C@@H]2CNC[C@H]2C(=O)N2CCOC[C@@H]2c2ccccc2)cc1] | 2'((3R,4S)-4-{[(3S)-3-phenylmorpholin-4-yl]carbonyl}pyrrolidin-3-yl)biphenyl-4-carbonitrile | R,S,S or S,R,S | 437.546 | Int. 11, Scheme C |
| 18 | 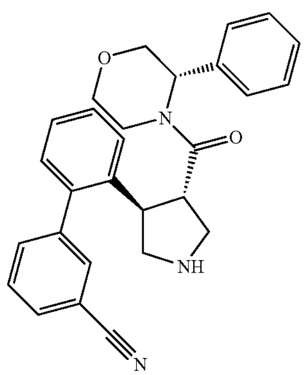 [SMILES: N#Cc1cccc(-c2ccccc2[C@@H]2CNC[C@H]2C(=O)N2CCOC[C@@H]2c2ccccc2)c1] | 2'-((3R,4S)-4-{[(3S)-3-phenylmorpholin-4-yl]carbonyl}pyrrolidin-3-yl)biphenyl-3-carbonitrile | R,S,S or S,R,S | 437.546 | Int. 11, Scheme C |
| 19 | 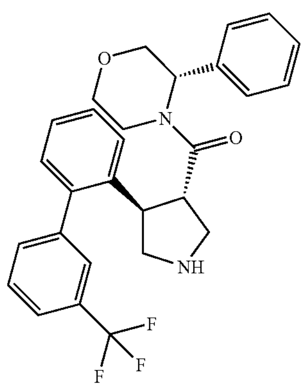 [SMILES: O=C([C@@H]1CNC[C@H]1c1ccccc1-c1cccc(C(F)(F)F)c1)N1CCOC[C@@H]1c1ccccc1] | (3S)-3-phenyl-4-({(3S,4R)-4-[3'-(trifluoromethyl)biphenyl-2-yl]pyrrolidin-3-yl}carbonyl)morpholine | R,S,S or S,R,S | 480.535 | Int. 11, Scheme C |
| 20 | 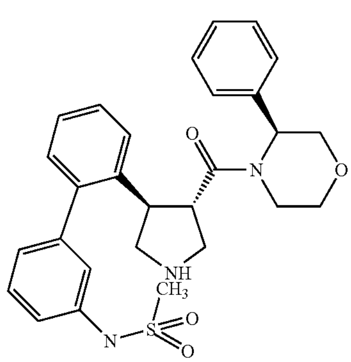 [SMILES: CS(=O)(=O)Nc1cccc(-c2ccccc2[C@@H]2CNC[C@H]2C(=O)N2CCOC[C@@H]2c2ccccc2)c1] | N-[2'-((3R,4S)-4-{[(3S)-3-phenylmorpholin-4-yl]carbonyl}pyrrolidin-3-yl)biphenyl-3-yl]methanesulfonamide | R,S,S or S,R,S | 505.641 | Int. 11, Scheme C |

TABLE 2-continued

| Ex | Structure | Chemical Name | Stereochemistry | Parent Weight | Intermed., Scheme and reference example |
|---|---|---|---|---|---|
| 21 | 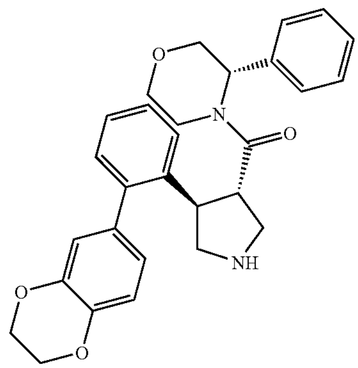 [SMILES: O=C([C@@H]1CNC[C@H]1c1ccccc1-c1ccc2c(c1)OCCO2)N1CCOC[C@@H]1c1ccccc1] | (3S)-4-({(3S,4R)-4-[2-(2,3-dihydro-1,4-benzodioxin-6-yl)phenyl]pyrrolidin-3-yl}carbonyl)-3-phenylmorpholine | R,S,S or S,R,S | 470.573 | Int. 11, Scheme C |
| 22 | 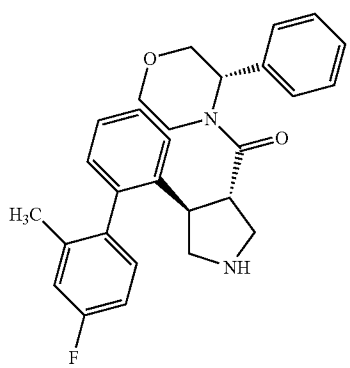 [SMILES: Cc1cc(F)ccc1-c1ccccc1[C@@H]1CNC[C@H]1C(=O)N1CCOC[C@@H]1c1ccccc1] | (3S)-4-{[3S,4R)-4-[4'-fluoro-2'-methylbiphenyl-2-yl)pyrrolidin-3-yl]carbonyl}-3-phenylmorpholine | R,S,S or S,R,S | 444.554 | Int. 11, Scheme C |
| 23 | 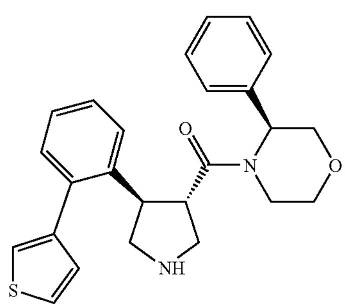 [SMILES: O=C([C@@H]1CNC[C@H]1c1ccccc1-c1ccsc1)N1CCOC[C@@H]1c1ccccc1] | (3S)-3-phenyl-4-({(3S,4R)-4-[2-(3-thienyl)phenyl]pyrrolidin-3-yl}carbonyl)morpholine | R,S,S or S,R,S | 418.562 | Int. 11, Scheme C |
| 24 | 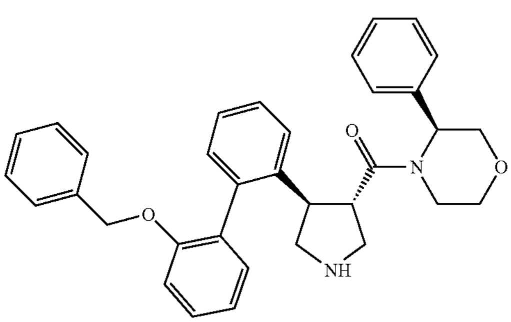 [SMILES: O=C([C@@H]1CNC[C@H]1c1ccccc1-c1ccccc1OCc1ccccc1)N1CCOC[C@@H]1c1ccccc1] | (3S)-4-({(3S,4R)-4-[2'-(benzyloxy)biphenyl-2-yl]pyrrolidin-3-yl}carbonyl)-3-phenylmorpholine | R,S,S or S,R,S | 518.662 | Int. 11, Scheme C |

TABLE 2-continued

| Ex | Structure | Chemical Name | Stereochemistry | Parent Weight | Intermed., Scheme and reference example |
|---|---|---|---|---|---|
| 25 | 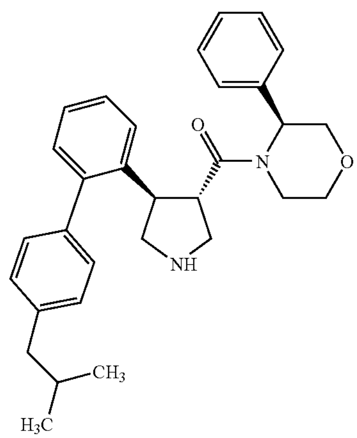 [SMILES: CC(C)Cc1ccc(-c2ccccc2[C@@H]2CNC[C@H]2C(=O)N2CCOC[C@@H]2c2ccccc2)cc1] | (3S)-4-{[3S,4R)-4-[4'-isobutylbiphenyl-2-yl)pyrrolidin-3-yl]carbonyl}-3-phenylmorpholine | R,S,S or S,R,S | 468.645 | Int. 11, Scheme C |
| 26 | 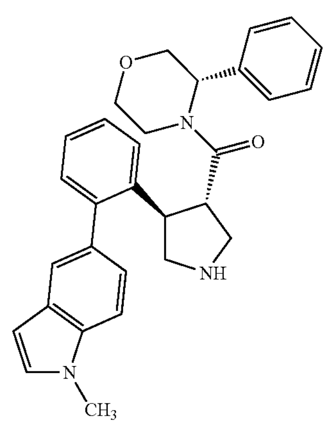 [SMILES: Cn1ccc2cc(-c3ccccc3[C@@H]3CNC[C@H]3C(=O)N3CCOC[C@@H]3c3ccccc3)ccc21] | 1-methyl-5-[2-(((3R,4S)-4-{[(3S)-3-phenylmorpholin-4-yl]carbonyl}pyrrolidin-3-yl)phenyl]-1H-indole | R,S,S or S,R,S | 465.6 | Int. 11, Scheme C |
| 27 | 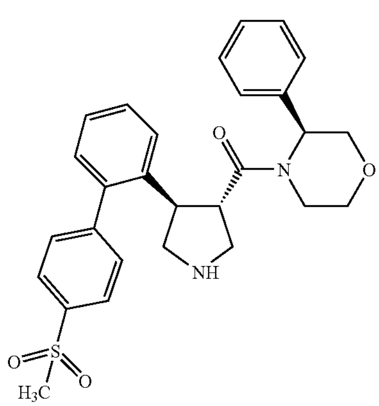 [SMILES: CS(=O)(=O)c1ccc(-c2ccccc2[C@@H]2CNC[C@H]2C(=O)N2CCOC[C@@H]2c2ccccc2)cc1] | (3S)-4-({(3S,4R)-4-[4'-(methylsulfonyl)biphenyl-2-yl]pyrrolidin-3-yl}carbonyl)-3-phenylmorpholine | R,S,S or S,R,S | 490.626 | Int. 11, Scheme C |

TABLE 2-continued

| Ex | Structure | Chemical Name | Stereochemistry | Parent Weight | Intermed., Scheme and reference example |
|---|---|---|---|---|---|
| 28 | 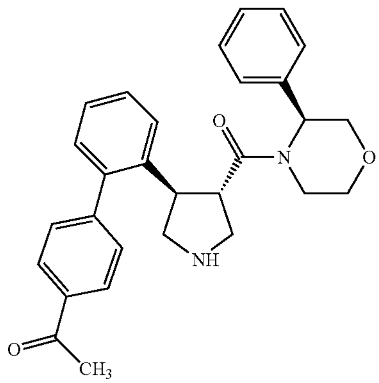 [SMILES: CC(=O)c1ccc(-c2ccccc2[C@@H]2CNC[C@H]2C(=O)N2CCOC[C@@H]2c2ccccc2)cc1] | 1-[2'-((3R,4S)-4-{[(3S)-3-phenylmorpholin-4-yl]carbonyl}pyrrolidin-3-yl)biphenyl-4-yl]ethanone | R,S,S or S,R,S | 454.574 | Int. 11, Scheme C |
| 29 | 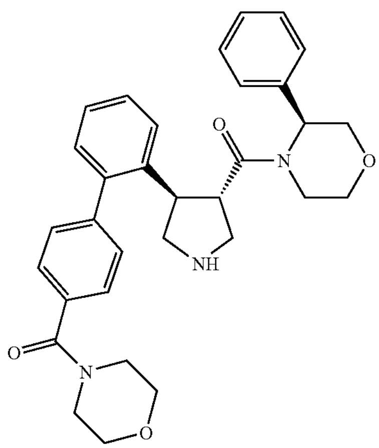 [SMILES: O=C(c1ccc(-c2ccccc2[C@@H]2CNC[C@H]2C(=O)N2CCOC[C@@H]2c2ccccc2)cc1)N1CCOCC1] | (3S)-4-({[3S,4R)-4-[4'-(morpholin-4-ylcarbonyl)biphenyl-2-yl]pyrrolidin-3-yl}carbonyl)-3-phenylmorpholine | R,S,S or S,R,S | 525.653 | Int. 11, Scheme C |
| 30 | 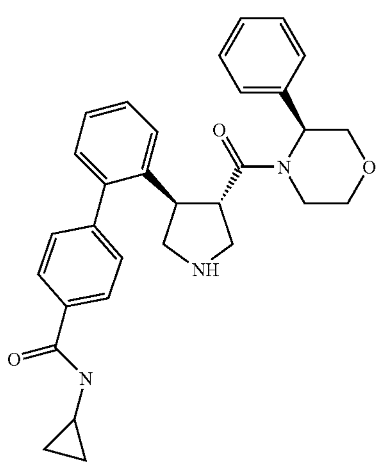 [SMILES: O=C(NC1CC1)c1ccc(-c2ccccc2[C@@H]2CNC[C@H]2C(=O)N2CCOC[C@@H]2c2ccccc2)cc1] | N-cyclopropyl-2'-((3R,4S)-4-{[(3S)-3-phenylmorpholin-4-yl]carbonyl}pyrrolidin-3-yl)biphenyl-4-carboxamide | R,S,S or S,R,S | 495.627 | Int. 11, Scheme C |

TABLE 2-continued

| Ex | Structure | Chemical Name | Stereochemistry | Parent Weight | Intermed., Scheme and reference example |
|---|---|---|---|---|---|
| 31 | 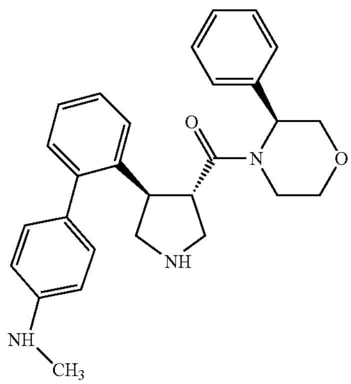 [SMILES: CNc1ccc(-c2ccccc2[C@@H]2CNC[C@H]2C(=O)N2CCOC[C@@H]2c2ccccc2)cc1] | N-methyl-2'-((3R,4S)-4-{[(3S)-3-phenylmorpholin-4-yl]carbonyl}pyrrolidin-3-yl)biphenyl-4-amine | R,S,S or S,R,S | 441.578 | Int. 11, Scheme C |
| 32 | 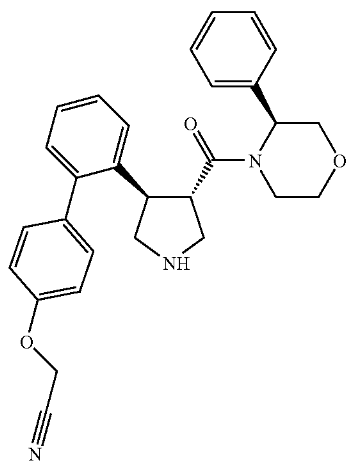 [SMILES: N#CCOc1ccc(-c2ccccc2[C@@H]2CNC[C@H]2C(=O)N2CCOC[C@@H]2c2ccccc2)cc1] | {[2'-((3R,4S)-4-{[(3S)-3-phenylmorpholin-4-yl]carbonyl}pyrrolidin-3-yl)biphenyl-4-yl]oxy}acetonitrile | R,S,S or S,R,S | 467.573 | Int. 11, Scheme C |
| 33 | 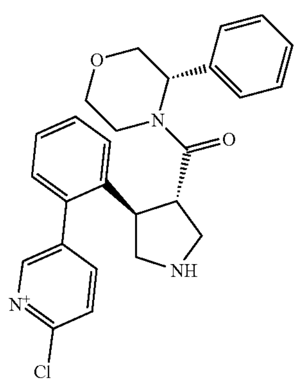 [SMILES: O=C([C@@H]1CNC[C@H]1c1ccccc1-c1ccc(Cl)[nH+]c1)N1CCOC[C@@H]1c1ccccc1] | (3S)-4-({(3S,4R)-4-[2-(6-chloropyridin-3-yl)phenyl]pyrrolidin-3-yl}carbonyl)-3-phenylmorpholine | R,S,S or S,R,S | 447.969 | Int. 11, Scheme C |
| 34 | 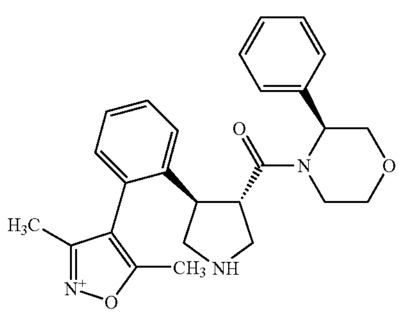 [SMILES: Cc1[nH+]oc(C)c1-c1ccccc1[C@@H]1CNC[C@H]1C(=O)N1CCOC[C@@H]1c1ccccc1] | (3S)-4-({(3S,4R)-4-[2-(3,5-dimethylisoxazol-4-yl)phenyl]pyrrolidin-3-yl}carbonyl)-3-Phenylmorpholine | R,S,S or S,R,S | 431.539 | Int. 11, Scheme C |

TABLE 2-continued

| Ex | Structure | Chemical Name | Stereochemistry | Parent Weight | Intermed., Scheme and reference example |
|---|---|---|---|---|---|
| 35 | 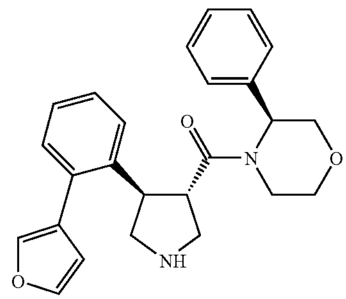 [SMILES: O=C([C@@H]1CNC[C@H]1c1ccccc1-c1ccoc1)N1CCOC[C@@H]1c1ccccc1] | (3S)-4-({(3S,4R)-4-[2-(3-furyl)phenyl]pyrrolidin-3-yl}carbonyl)-3-phenylmorpholine | R,S,S or S,R,S | 402.498 | Int. 11, Scheme C |
| 36 | 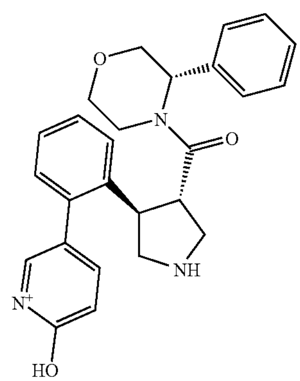 [SMILES: O=C([C@@H]1CNC[C@H]1c1ccccc1-c1ccc(O)[nH+]c1)N1CCOC[C@@H]1c1ccccc1] | 5-[2-((3R,4S)-4-{[(3S)-3-phenylmorpholin-4-yl]carbonyl}pyrrolidin-3-yl)phenyl]pyridin-2-ol | R,S,S or S,R,S | 429.523 | Int. 11, Scheme C |
| 37 | 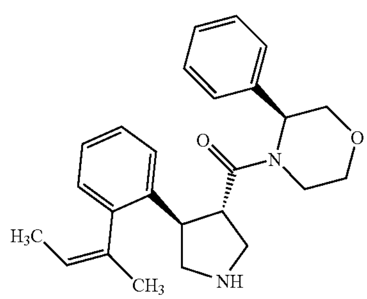 [SMILES: C/C=C(/C)c1ccccc1[C@@H]1CNC[C@H]1C(=O)N1CCOC[C@@H]1c1ccccc1] | (3S)-4-[((3S,4R)-4-{2-[(1Z)-1-methylprop-1-en-1-yl]phenyl}pyrrolidin-3-yl)carbonyl]-3-phenylmorpholine | R,S,S or S,R,S | 390.53 | Int. 11, Scheme C |
| 38 | 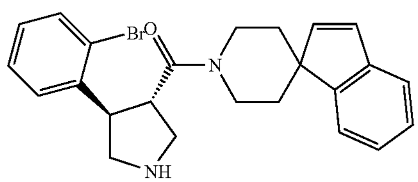 [SMILES: O=C([C@@H]1CNC[C@H]1c1ccccc1Br)N1CCC2(C=Cc3ccccc32)CC1] | 1-{[(3S,4R)-4-(2-bromophenyl)pyrrolidin-3-yl]carbonyl}spiro[indene-1,4'-piperidine] | R,S,RS or S,R,RS | 437.384 | Int. 9, Scheme B Ex2 |
| 39 | 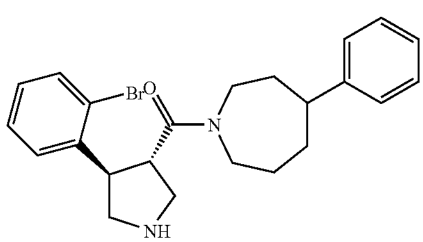 [SMILES: O=C([C@@H]1CNC[C@H]1c1ccccc1Br)N1CCCC(c2ccccc2)CC1] | 1'-{[(3S,4R)-4-(2-bromophenyl)pyrrolidin-3-yl]carbonyl}-4-phenylazepane | R,S,RS or S,R,RS | 427.388 | Int. 9, Scheme B Ex2 |

TABLE 2-continued

| Ex | Structure | Chemical Name | Stereochemistry | Parent Weight | Intermed., Scheme and reference example |
|---|---|---|---|---|---|
| 40 | 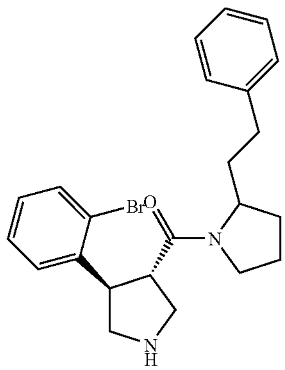 [SMILES: O=C([C@@H]1CNC[C@H]1c1ccccc1Br)N1CCCC1CCc1ccccc1] | 1-{[(3S,4R)-4-(2-bromophenyl)pyrrolidin-3-yl]carbonyl}-2-(2-phenylethyl)pyrrolidine | R,S,RS or S,R,RS | 427.388 | Int. 9, Scheme B Ex2 |
| 41 | 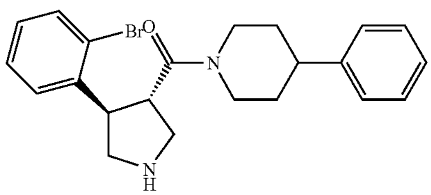 [SMILES: O=C([C@@H]1CNC[C@H]1c1ccccc1Br)N1CCC(c2ccccc2)CC1] | 1-{[(3S,4R)-4-(2-bromophenyl)pyrrolidin-3-yl]carbonyl}-4-phenylpiperidine | R,S or S,R | 413.361 | Int. 9, Scheme B Ex2 |
| 42 | 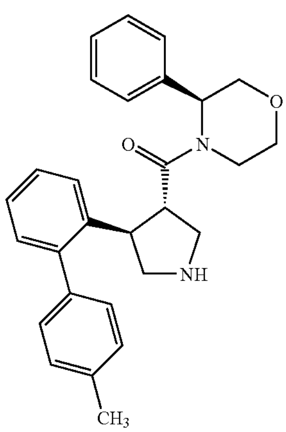 [SMILES: Cc1ccc(-c2ccccc2[C@@H]2CNC[C@H]2C(=O)N2CCOC[C@@H]2c2ccccc2)cc1] | 2'-((3R,4S)-4-{[(3S)-3-phenylmorpholin-4-yl]carbonyl}pyrrolidin-3-yl)biphenyl-4-ol | R,S,S or S,R,S | 428.536 | Int. 11, Scheme C |
| 43 | 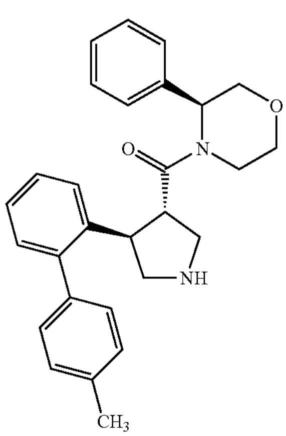 [SMILES: Cc1ccc(-c2ccccc2[C@@H]2CNC[C@H]2C(=O)N2CCOC[C@@H]2c2ccccc2)cc1] | (3S)-4-{[(3S,4R)-4-(4'-methylbiphenyl-2-yl)pyrrolidin-3-yl]carbonyl}-3-phenylmorpholine | R,S,S or S,R,S | 426.563 | Int. 11, Scheme C |

TABLE 2-continued

| Ex | Structure | Chemical Name | Stereochemistry | Parent Weight | Intermed., Scheme and reference example |
|---|---|---|---|---|---|
| 44 | 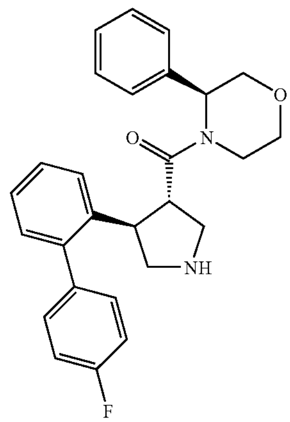 [SMILES: O=C([C@@H]1CNC[C@H]1c1ccccc1-c1ccc(F)cc1)N1CCOC[C@@H]1c1ccccc1] | (3S)-4-{[(3S,4R)-4-(4'-fluorophenyl-2-yl)pyrrolidin-3-yl]carbonyl}-3-phenylmorpholine | R,S,S or S,R,S | 430.527 | Int. 11, Scheme C |
| 45 | 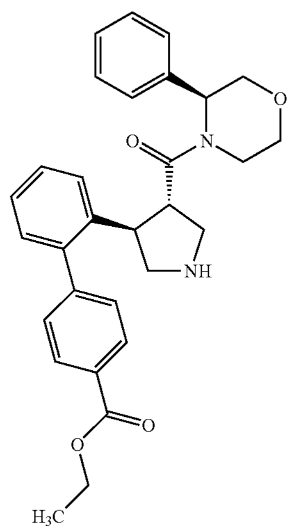 [SMILES: CCOC(=O)c1ccc(-c2ccccc2[C@@H]2CNC[C@H]2C(=O)N2CCOC[C@@H]2c2ccccc2)cc1] | ethyl 2'-((3R,4S)-4-{[(3S)-3-phenylmorpholin-4-yl]carbonyl}pyrrolidin-3-yl)biphenyl-4-carboxylate | R,S,S or S,R,S | 484.601 | Int. 11, Scheme C |
| 46 | 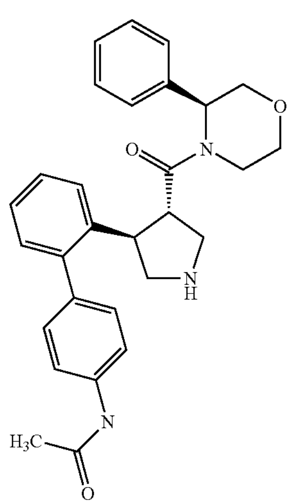 [SMILES: CC(=O)Nc1ccc(-c2ccccc2[C@@H]2CNC[C@H]2C(=O)N2CCOC[C@@H]2c2ccccc2)cc1] | N-[2'-((3R,4S)-4-{[(3S)-3-phenylmorpholin-4-yl]carbonyl}pyrrolidin-3-yl)biphenyl-4-yl]acetamide | R,S,S or S,R,S | 469.589 | Int. 11, Scheme C |

TABLE 2-continued

| Ex | Structure | Chemical Name | Stereochemistry | Parent Weight | Intermed., Scheme and reference example |
|---|---|---|---|---|---|
| 47 | 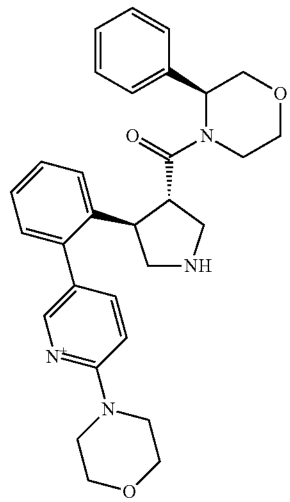 [SMILES: O=C([C@@H]1CNC[C@H]1c1ccccc1-c1ccc(N2CCOCC2)[nH+]c1)N1CCOC[C@@H]1c1ccccc1] | (3S)-4-({(3S,4R)-4-[2-(6-morpholin-4-yl pyridin-3-yl) phenyl]pyrrolidin-3-yl} carbonyl)-3-phenylmorpholine | R,S,S or S,R,S | 498.63 | Int. 11, Scheme C |
| 48 | 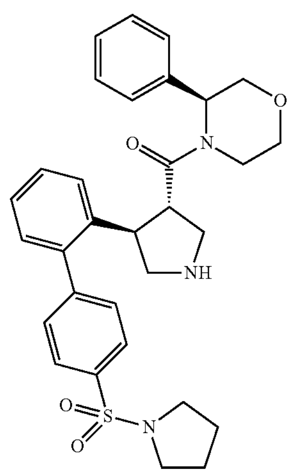 [SMILES: O=C([C@@H]1CNC[C@H]1c1ccccc1-c1ccc(S(=O)(=O)N2CCCC2)cc1)N1CCOC[C@@H]1c1ccccc1] | (3S)-3-phenyl-4-({(3S,4R)-4-[4'-(pyrrolidin-1-yl sulfonyl)biphenyl-2-yl] pyrrolidin-3-yl} carbonyl)morpholine | R,S,S or S,R,S | 545.706 | Int. 11, Scheme C |
| 49 | 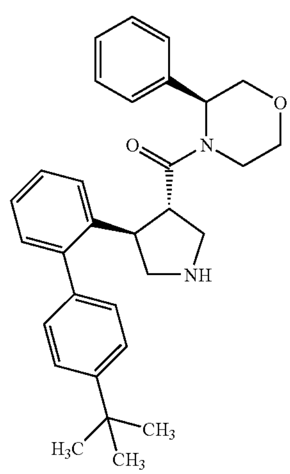 [SMILES: CC(C)(C)c1ccc(-c2ccccc2[C@@H]2CNC[C@H]2C(=O)N2CCOC[C@@H]2c2ccccc2)cc1] | (3S)-4-{[(3S,4R)-4-(4'-tert-butylbiphenyl-2-yl) pyrrolidin-3-yl] carbonyl}-3-phenylmorpholine | R,S,S or S,R,S | 468.645 | Int. 11, Scheme C |

TABLE 2-continued

| Ex | Structure | Chemical Name | Stereochemistry | Parent Weight | Intermed., Scheme and reference example |
|---|---|---|---|---|---|
| 50 | 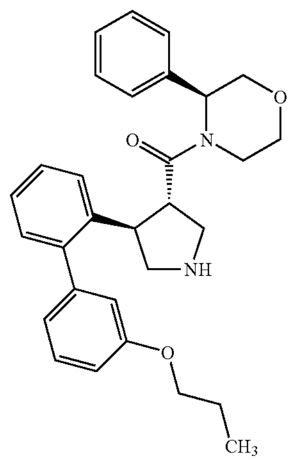 [SMILES: CCCOc1cccc(-c2ccccc2[C@@H]2CNC[C@H]2C(=O)N2CCOC[C@@H]2c2ccccc2)c1] | (3S)-3-phenyl-4-{[(3S,4R)-4-(3'-propoxybiphenyl-2-yl)pyrrolidin-3-yl]carbonyl}morpholine | R,S,S or S,R,S | 470.617 | Int. 11, Scheme C |
| 51 | 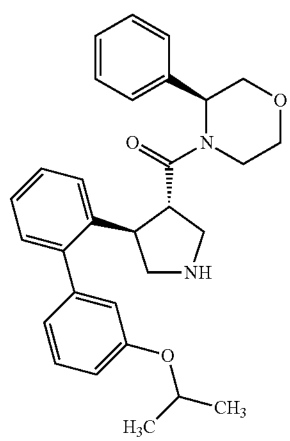 [SMILES: CC(C)Oc1cccc(-c2ccccc2[C@@H]2CNC[C@H]2C(=O)N2CCOC[C@@H]2c2ccccc2)c1] | (3S)-4-{[(3S,4R)-4-(3'-isopropoxybiphenyl-2-yl)pyrrolidin-3-yl]carbonyl}-3-phenylmorpholine | R,S,S or S,R,S | 470.617 | Int. 11, Scheme C |
| 52 | 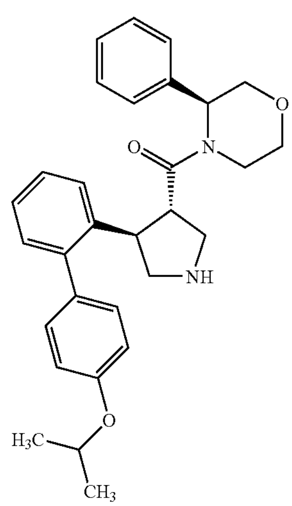 [SMILES: CC(C)Oc1ccc(-c2ccccc2[C@@H]2CNC[C@H]2C(=O)N2CCOC[C@@H]2c2ccccc2)cc1] | (3S)-4-{[(3S,4R)-4-(4'-isopropoxybiphenyl-2-yl)pyrrolidin-3-yl]carbonyl}-3-phenylmorpholine | R,S,S or S,R,S | 470.617 | Int. 11, Scheme C |

TABLE 2-continued

| Ex | Structure | Chemical Name | Stereochemistry | Parent Weight | Intermed., Scheme and reference example |
|---|---|---|---|---|---|
| 53 | 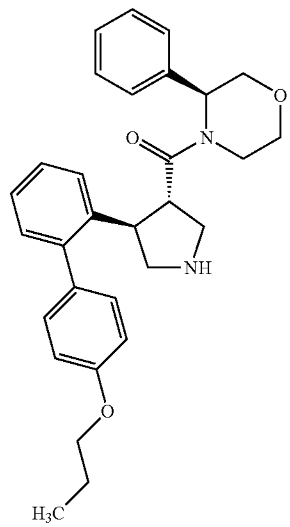 [SMILES: CCCOc1ccc(-c2ccccc2[C@@H]2CNC[C@H]2C(=O)N2CCOC[C@@H]2c2ccccc2)cc1] | (3S)-3-phenyl-4-{[(3S,4R)-4-(4'-propoxybiphenyl-2-yl)pyrrolidin-3-yl]carbonyl}morpholine | R,S,S or S,R,S | 470.617 | Int. 11, Scheme C |
| 54 | 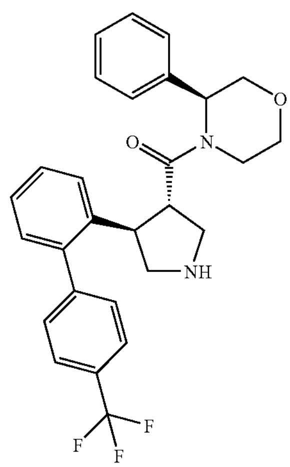 [SMILES: O=C([C@@H]1CNC[C@H]1c1ccccc1-c1ccc(C(F)(F)F)cc1)N1CCOC[C@@H]1c1ccccc1] | (3S)-3-phenyl-4-{[(3S,4R)-4-(4'-(trifluoromethyl)biphenyl-2-yl]pyrrolidin-3-yl}carbonyl)morpholine | R,S,S or S,R,S | 480.535 | Int. 11, Scheme C |
| 55 | 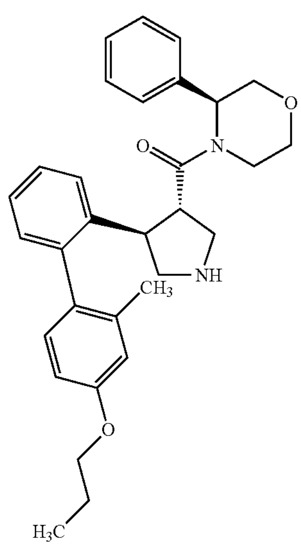 [SMILES: CCCOc1ccc(-c2ccccc2[C@@H]2CNC[C@H]2C(=O)N2CCOC[C@@H]2c2ccccc2)c(C)c1] | (3S)-4-{[(3S,4R)-4-(2'-methyl-4'-propoxybiphenyl-2-yl)pyrrolidin-3-yl]carbonyl}-3-phenylmorpholine | R,S,S or S,R,S | 484.644 | Int. 11, Scheme C |

TABLE 2-continued

| Ex | Structure | Chemical Name | Stereochemistry | Parent Weight | Intermed., Scheme and reference example |
|---|---|---|---|---|---|
| 56 | 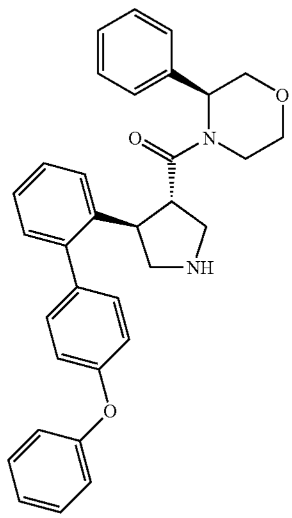 [SMILES: O=C([C@@H]1CNC[C@H]1c1ccccc1-c1ccc(Oc2ccccc2)cc1)N1CCOC[C@@H]1c1ccccc1] | (3S)-4-{[(3S,4R)-4-(4'-phenoxybiphenyl-2-yl)pyrrolidin-3-yl]carbonyl}-3-phenylmorpholine | R,S,S or S,R,S | 504.635 | Int. 11, Scheme C |
| 57 | 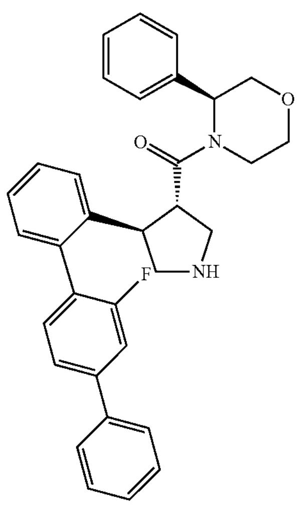 [SMILES: O=C([C@@H]1CNC[C@H]1c1ccccc1-c1ccc(-c2ccccc2)cc1F)N1CCOC[C@@H]1c1ccccc1] | (3S)-4-{[(3S,4R)-4-(2'-fluoro-1,1':4',1''-terphenyl-2-yl)pyrrolidin-3-yl]carbonyl}-3-phenylmorpholine | R,S,S or S,R,S | 506.626 | Int. 11, Scheme C |
| 58 | 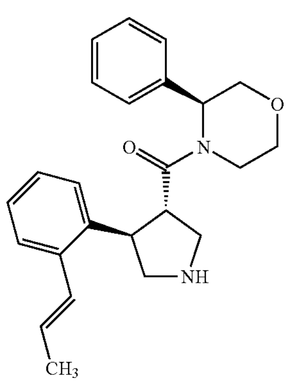 [SMILES: C/C=C/c1ccccc1[C@@H]1CNC[C@H]1C(=O)N1CCOC[C@@H]1c1ccccc1] | (3S)-3-phenyl-4-[((3S,4R)-4-{2-[(1E)-prop-1-en-1-yl]phenyl}pyrrolidin-3-yl)carbonyl]morpholine | R,S,S or S,R,S | 376.503 | Int. 11, Scheme C |

TABLE 2-continued

| Ex | Structure | Chemical Name | Stereochemistry | Parent Weight | Intermed., Scheme and reference example |
|---|---|---|---|---|---|
| 59 | 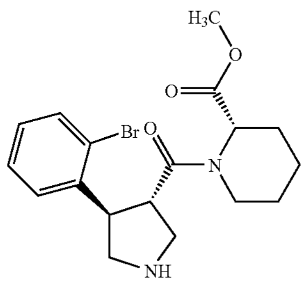 [SMILES: COC(=O)[C@@H]1CCCCN1C(=O)[C@@H]1CNC[C@H]1c1ccccc1Br] | methyl (2S)-1-{[(3S,4R)-4-(2-bromophenyl)pyrrolidin-3-yl]carbonyl}piperidine-2-carboxylate | R,S,S or S,R,S | 395.3 | Int. 9, Scheme B, Ex2 |
| 60 | 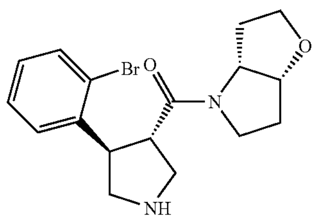 [SMILES: O=C([C@@H]1CNC[C@H]1c1ccccc1Br)N1CC[C@H]2OCC[C@H]21] | methyl (2S)-1-{[(3S,4R)-4-(2-bromophenyl)pyrrolidin-3-yl]carbonyl}piperidine-2-carboxylate | R,S,R,R or S,R,R,R | 365.273 | Int. 9, Scheme B, Ex2 |
| 61 | 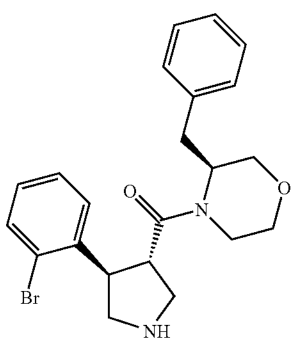 [SMILES: O=C([C@@H]1CNC[C@H]1c1ccccc1Br)N1CCOC[C@@H]1Cc1ccccc1] | (3S)-3-benzyl-4-{[(3S,4R)-4-(2-bromophenyl)pyrrolidin-3-yl]carbonyl}morpholine | [R,S,(S or R) or S,R,(S or R) | 429.361 | Int. 9, Scheme B, Ex2 |
| 62 | 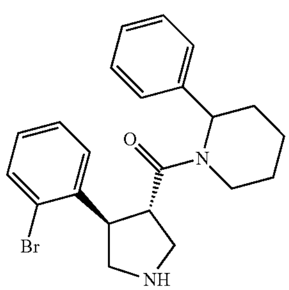 [SMILES: O=C([C@@H]1CNC[C@H]1c1ccccc1Br)N1CCCCC1c1ccccc1] | 1-{[(3S,4R)-4-(2-bromophenyl)pyrrolidin-3-yl]carbonyl}-2-phenylpiperidine | R,S,RS or S,R,RS | 413.361 | Int. 9, Scheme B, Ex2 |
| 63 | 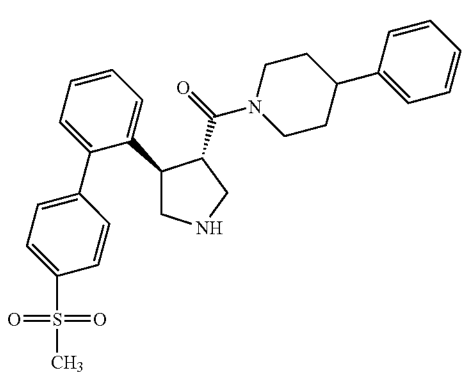 [SMILES: CS(=O)(=O)c1ccc(-c2ccccc2[C@@H]2CNC[C@H]2C(=O)N2CCC(c3ccccc3)CC2)cc1] | 1-({(3S,4R)-4-[4'-(methylsulfonyl)biphenyl-2-yl]pyrrolidin-3-yl}carbonyl)-4-phenylpiperidine | R,S or S,R | 488.654 | Scheme C |

TABLE 2-continued

| Ex | Structure | Chemical Name | Stereochemistry | Parent Weight | Intermed., Scheme and reference example |
|---|---|---|---|---|---|
| 64 | 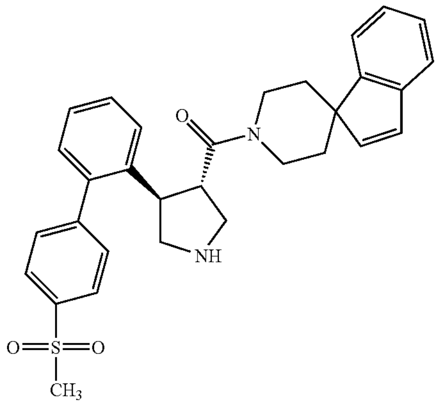 [SMILES: CS(=O)(=O)c1ccc(-c2ccccc2[C@@H]2CNC[C@H]2C(=O)N2CCC3(C=Cc4ccccc43)CC2)cc1] | 1'({[(3S,4R)-4-[4'-(methylsulfonyl)biphenyl-2-yl]pyrrolidin-3-yl}carbonyl)spiro indine-1,4'-piperidine] | R,S or S,R | 512.676 | Scheme C |
| 65 | 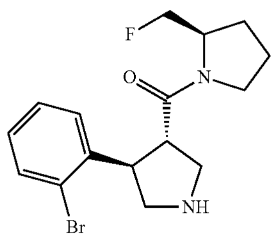 [SMILES: O=C([C@@H]1CNC[C@H]1c1ccccc1Br)N1CCC[C@@H]1CF] | (2R)-1-{[(3S,4R)-4-(2-bromophenyl)pyrrolidin-3-yl]carbonyl}-2-(fluoromethyl)pyrrolidine | R,S,R or S,R,R | 355.253 | Int. 9, Scheme B, Ex2 |
| 66 | 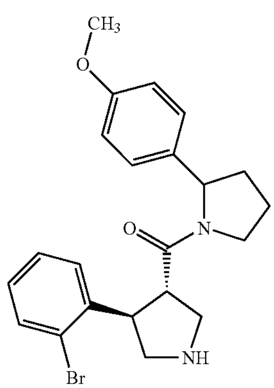 [SMILES: COc1ccc(C2CCCN2C(=O)[C@@H]2CNC[C@H]2c2ccccc2Br)cc1] | 1-{[(3S,4R)-4-(2-bromophenyl)pyrrolidin-3-yl]carbonyl}-2-(4-methoxyphenyl)pyrrolidine | R,S,RS or S,R,RS | 429.361 | Int. 9, Scheme B Ex2 |
| 67 | 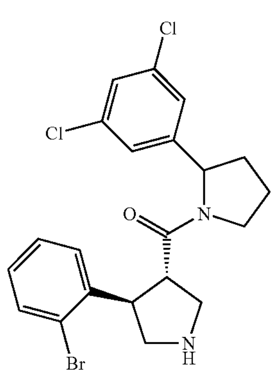 [SMILES: O=C([C@@H]1CNC[C@H]1c1ccccc1Br)N1CCCC1c1cc(Cl)cc(Cl)c1] | 1-{[(3S,4R)-4-(2-bromophenyl)pyrrolidin-3-yl]carbonyl}-2-(4-methoxyphenyl)pyrrolidine | R,S,RS or S,R,RS | 468.224 | Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 68 | 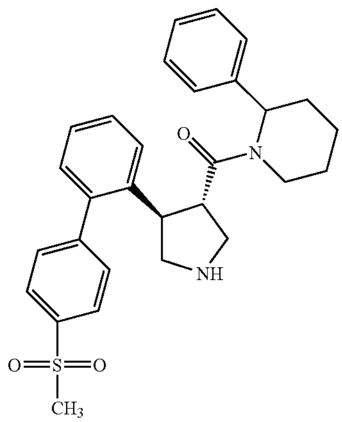 [SMILES: CS(=O)(=O)c1ccc(-c2ccccc2[C@@H]2CNC[C@H]2C(=O)N2CCCCC2c2ccccc2)cc1] | 1-{[(3S,4R)-4-(4'-(methylsulfonyl)biphenyl-2-yl]pyrrolidin-3-yl}carbonyl)-2-phenylpiperidine | R,S,RS or S,R,RS | 488.654 | Scheme C |
| 69 | 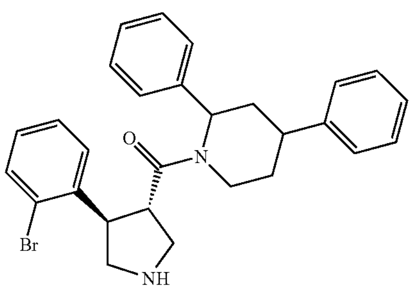 [SMILES: O=C([C@@H]1CNC[C@H]1c1ccccc1Br)N1CCC(c2ccccc2)CC1c1ccccc1] | 1-{[(3S,4R)-4-(2-bromophenyl)pyrrolidin-3-yl]carbonyl}-2,4-diphenylpiperidine | Mixture of 4 Diastereomers | 489.46 | Int. 1A, Int. 9, Scheme B, Ex2 |
| 70 | 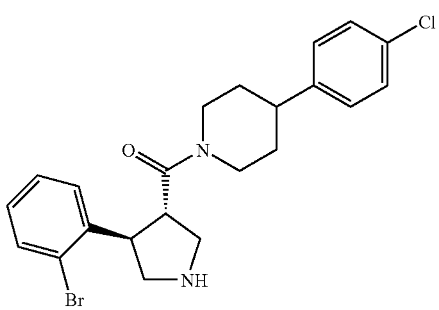 [SMILES: O=C([C@@H]1CNC[C@H]1c1ccccc1Br)N1CCC(c2ccc(Cl)cc2)CC1] | 1-{[(3S,4R)-4-(2-bromophenyl)pyrrolidin-3-yl]carbonyl}-4-(4-chlorophenyl)piperidine | R,S,RS or S,R,RS | 447.806 | Int. 9, Scheme B, Ex2 |
| 71 | 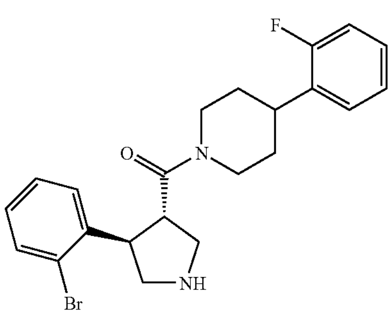 [SMILES: O=C([C@@H]1CNC[C@H]1c1ccccc1Br)N1CCC(c2ccccc2F)CC1] | 1-{[(3S,4R)-4-(2-bromophenyl)pyrrolidin-3-yl]carbonyl}-4-(2-fluorophenyl)piperidine | R,S,RS or S,R,RS | 431.352 | Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 72 | 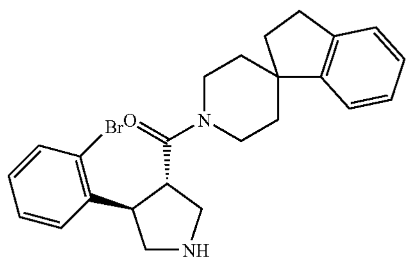 [SMILES: O=C([C@@H]1CNC[C@H]1c1ccccc1Br)N1CCC2(CCc3ccccc32)CC1] | 1'-{[(3S,4R)-4-(2-bromophenyl)pyrrolidin-3-yl]carbonyl}-2,3-dihydrospiro[indene-1,4'-piperidine] | R,S or S,R | 439.4 | Int. 9, Scheme B, Ex2 |
| 73 | 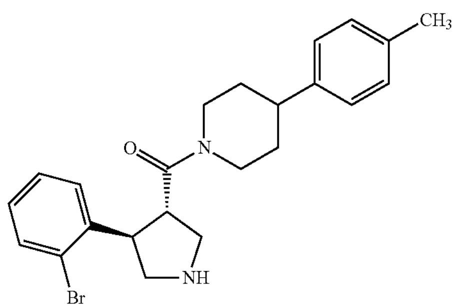 [SMILES: Cc1ccc(C2CCN(C(=O)[C@@H]3CNC[C@H]3c3ccccc3Br)CC2)cc1] | 1-{[(3S,4R)-4-(2-bromophenyl)pyrrolidin-3-yl]carbonyl}-4-(4-methylphenyl)piperidine | R,S,R or S or S,R,R or S | 427.388 | Int. 9, Scheme B, Ex2 |
| 74 | 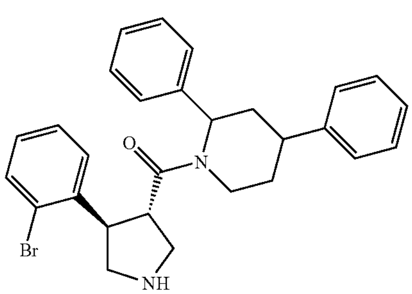 [SMILES: O=C([C@@H]1CNC[C@H]1c1ccccc1Br)N1CCC(c2ccccc2)CC1c1ccccc1] | 1-{[(3S,4R)-4-(2-bromophenyl)pyrrolidin-3-yl]carbonyl}-2,4-diphenylpiperidine | Single Diastereomer | 489.46 | Int. 1A, Int. 9, Scheme B, Ex2 |
| 75 | 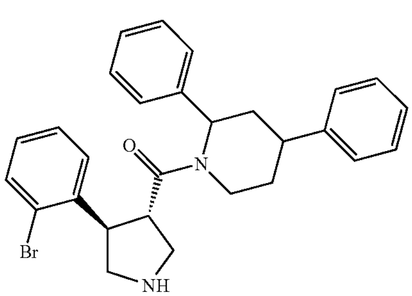 [SMILES: O=C([C@@H]1CNC[C@H]1c1ccccc1Br)N1CCC(c2ccccc2)CC1c1ccccc1] | 1-{[(3S,4R)-4-(2-bromophenyl)pyrrolidin-3-yl]carbonyl}-2,4-diphenylpiperdine | Single Diastereomer | 489.46 | Int. 1A, Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 76 | 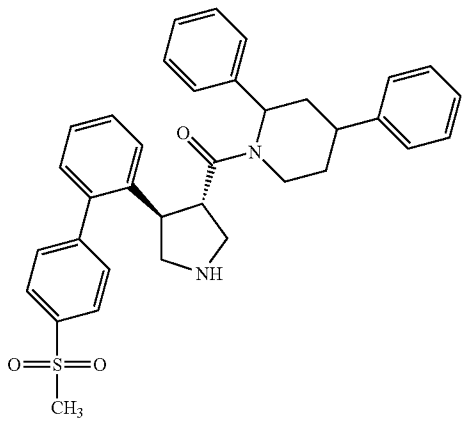 [SMILES: CS(=O)(=O)c1ccc(-c2ccccc2[C@@H]2CNC[C@H]2C(=O)N2CCC(c3ccccc3)CC2c2ccccc2)cc1] | 1-({(3S,4R)-4-[4'-(methylsulfonyl)biphenyl-2-yl]pyrrolidin-3-yl}carbonyl)-2,4-diphenylpiperidine | Mixture of 2 Diastereomers | 564.753 | Int. 1A, Int. 9, Scheme B, Scheme C, Ex2 |
| 77 | 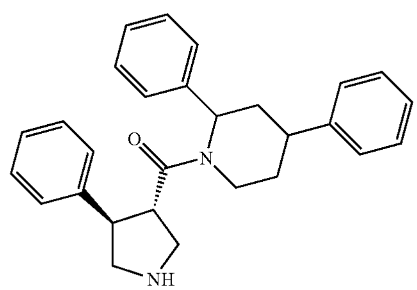 [SMILES: O=C([C@@H]1CNC[C@H]1c1ccccc1)N1CCC(c2ccccc2)CC1c1ccccc1] | 2,4-diphenyl-1-{[(3S,4R)-4-phenylpyrrolidin-3-yl]carbonyl}piperidine | Mixture of 2 Diastereomers | 410.564 | Int. 1A, Int. 9, Scheme B, Ex2 |
| 78 | 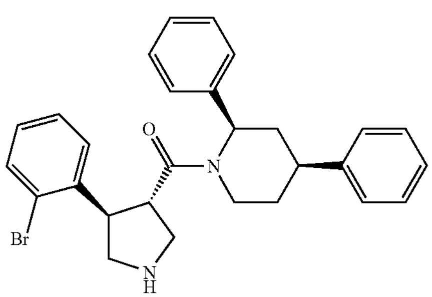 [SMILES: O=C([C@@H]1CNC[C@H]1c1ccccc1Br)N1CC[C@H](c2ccccc2)C[C@@H]1c1ccccc1] | (2R,4S)-1-{[(3S,4R)-4-(2-bromophenyl)pyrrolidin-3-yl]carbonyl}-2,4-diphenylpiperidine | Single Diastereomer | 489.46 | Int. 1A, Int. 9, Scheme B, Ex2 |
| 79 | 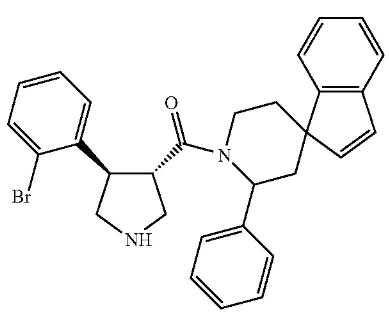 [SMILES: O=C([C@@H]1CNC[C@H]1c1ccccc1Br)N1CCC2(C=Cc3ccccc32)CC1c1ccccc1] | 1'-{[(3S,4R)-4-(2-bromophenyl)pyrrolidin-3-yl]carbonyl}-2'-phenylspiro[indene-1,4'-piperidine] | R,S or S,R RS, RS | 513.482 | Int. 1A, Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 80 | 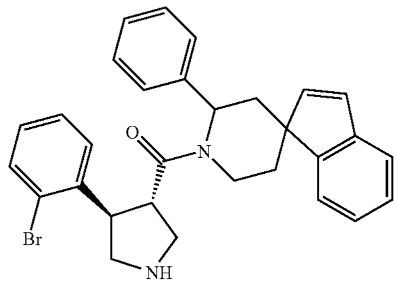 [SMILES: O=C([C@@H]1CNC[C@H]1c1ccccc1Br)N1CCC2(C=Cc3ccccc32)CC1c1ccccc1] | 1'-{[(3S,4R)-4-(2-bromophenyl)pyrrolidin-3-yl]carbonyl}-2'-phenylspiro[indene-1,4'-piperidine] | R,S or S,R,R or S,R or S | 513.482 | Int. 2, Int. 9, Scheme B, Ex2 |
| 81 | 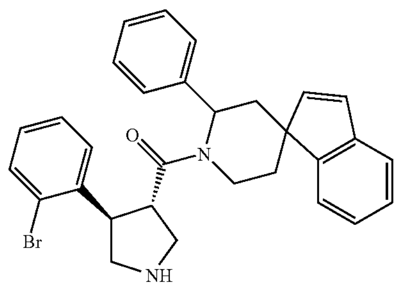 [SMILES: O=C([C@@H]1CNC[C@H]1c1ccccc1Br)N1CCC2(C=Cc3ccccc32)CC1c1ccccc1] | 1'-{[(3S,4R)-4-(2-bromophenyl)pyrrolidin-3-yl]carbonyl}-2'-phenylspiro[indene-1,4'-piperidine] | R,S or S,R,R or S,R or S | 513.482 | Int. 2, Int. 9, Scheme B, Ex2 |
| 82 | 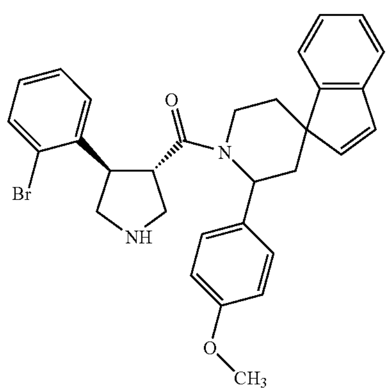 [SMILES: COc1ccc(C2CC3(C=Cc4ccccc43)CCN2C(=O)[C@@H]2CNC[C@H]2c2ccccc2Br)cc1] | 1'-{[(3S,4R)-4-(2-bromophenyl)pyrrolidin-3-yl]carbonyl}-2'-(4-methoxyphenyl)spiro[indene-1,4'-piperidine] | R,S or S,R RS,RS | 543.509 | Int. 2, Int. 9, Scheme B, Ex2 |
| 83 | 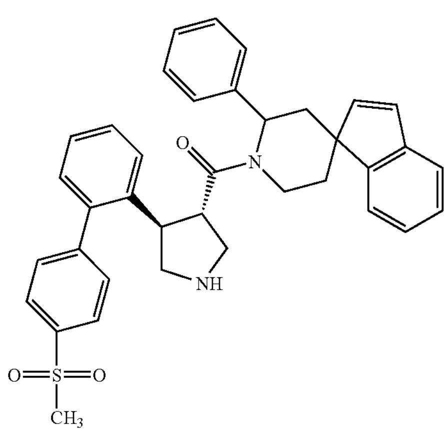 [SMILES: CS(=O)(=O)c1ccc(-c2ccccc2[C@@H]2CNC[C@H]2C(=O)N2CCC3(C=Cc4ccccc43)CC2c2ccccc2)cc1] | 1'-({(3S,4R)-4-(4'-(methylsulfonyl)biphenyl-2-yl]pyrrolidin-3-yl}carbonyl)-2'-phenylspiro-[indene-1,4'-piperidine] | R,S,R,S or S,R,R,S or S,R,S,R or R,S,S,R | 588.775 | Int. 2, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 84 | 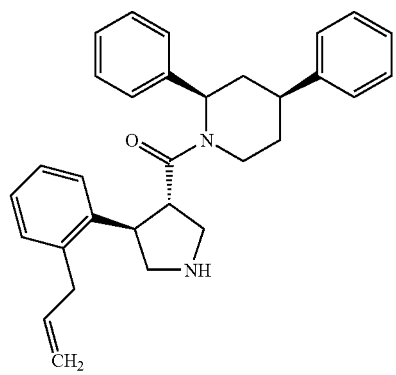 [SMILES: C=CCc1ccccc1[C@@H]1CNC[C@H]1C(=O)N1CC[C@H](c2ccccc2)C[C@@H]1c1ccccc1] | (2R,4S)-1-{[(3S,4R)-4-(2-allylphenyl)pyrrolidin-3-yl]carbonyl}-2,4-diphenylpiperidine | R,S,R,S or S,R,R,S or S,R,S,R or R,S,S,R | 588.775 | Int. 1A, Int. 9, Scheme B, Scheme C, Ex2 |
| 85 | 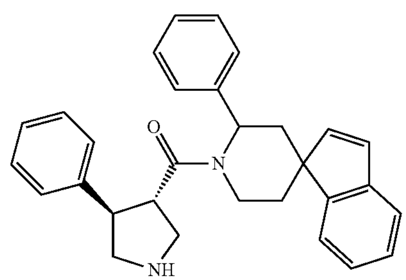 [SMILES: O=C([C@@H]1CNC[C@H]1c1ccccc1)N1CCC2(C=Cc3ccccc32)CC1c1ccccc1] | 2'-phenyl-1'-{[(3S,4R)-4-phenylpyrrolidin-3-yl]carbonyl}spiro[indene-1,4'-piperidine] | R,S,R,S or S,R,R,S or S,R,S,R or R,S,S,R | 434.586 | Int. 2, Int. 9, Scheme B, Scheme C, Ex2 |
| 86 | 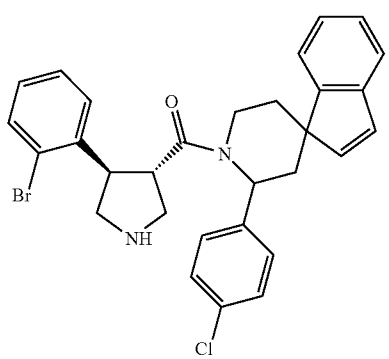 [SMILES: O=C([C@@H]1CNC[C@H]1c1ccccc1Br)N1CCC2(C=Cc3ccccc32)CC1c1ccc(Cl)cc1] | 1'-{[(3S,4R)-4-(2-bromophenyl)pyrrolidin-3-yl]carbonyl}-2'-(4-chlorophenyl)spiro[indene-1,4'-piperidine] | R,S, trans or S,R, trans | 547.927 | Int. 2, Int. 9, Scheme B, Ex2 |
| 87 | 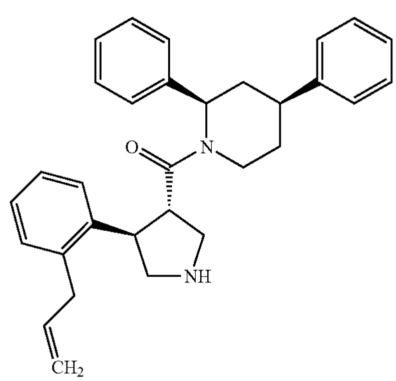 [SMILES: C=CCc1ccccc1[C@@H]1CNC[C@H]1C(=O)N1CC[C@H](c2ccccc2)C[C@@H]1c1ccccc1] | (2R,4S)-1-{[(3S,4R)-4-(2-allylphenyl)pyrrolidin-3-yl]carbonyl}-2,4-diphenylpiperidine | R,S,R,S or S,R,R,S or S,R,S,R or R,S,S,R | 450.629 | Int. 1A, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 88 | 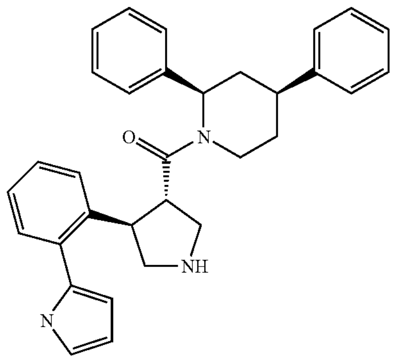 [SMILES: O=C([C@@H]1CNC[C@H]1c1ccccc1-c1ccc[nH]1)N1CC[C@H](c2ccccc2)C[C@@H]1c1ccccc1] | (2R,4S)-2,4-diphenyl-1-({(3S,4R)-4-[2-(1H-pyrrol-2-yl)phenyl]pyrrolidin-3-yl}carbonyl)piperidine | R,S,R,S or S,R,R,S or S,R,S,R or R,S,S,R | 475.639 | Int. 1A, Int. 9, Scheme B, Scheme C, Ex2 |
| 89 | 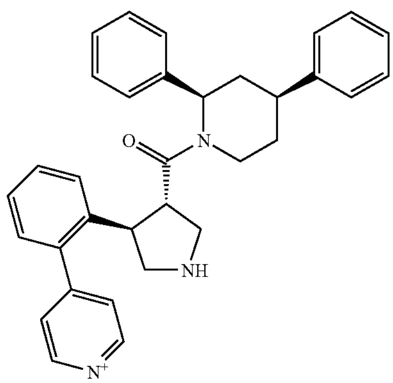 [SMILES: O=C([C@@H]1CNC[C@H]1c1ccccc1-c1cc[nH+]cc1)N1CC[C@H](c2ccccc2)C[C@@H]1c1ccccc1] | 4-[2-((3R,4S)-4-{[(2R,4S)-2,4-diphenylpiperidin-1-yl]carbonyl}pyrrolidin-3-yl)phenyl]pyridine | R,S,R,S or S,R,R,S or S,R,S,R or R,S,S,R | 487.65 | Int. 1A, Int. 9, Scheme B, Scheme C, Ex2 |
| 90 | 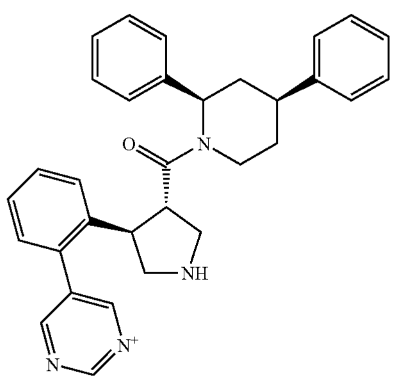 [SMILES: O=C([C@@H]1CNC[C@H]1c1ccccc1-c1cnc[nH+]c1)N1CC[C@H](c2ccccc2)C[C@@H]1c1ccccc1] | 5-[2-((3R,4S)-4-{[(2R,4S)-2,4-diphenylpiperidin-1-yl]carbonyl}pyrrolidin-3-yl)phenyl]pyrimidine | R,S,R,S or S,R,R,S or S,R,S,R or R,S,S,R | 488.638 | Int. 1A, Int. 9, Scheme B, Scheme C, Ex2 |
| 91 | 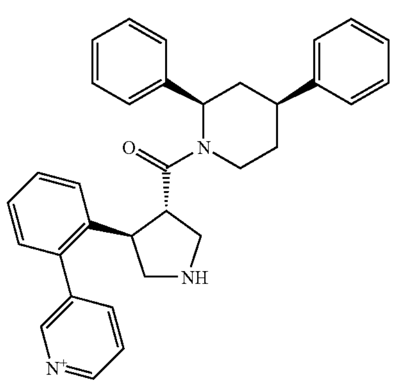 [SMILES: O=C([C@@H]1CNC[C@H]1c1ccccc1-c1ccc[nH+]c1)N1CC[C@H](c2ccccc2)C[C@@H]1c1ccccc1] | 3-[2-((3R,4S)-4-{[(2R,4S)-2,4-diphenylpiperidin-1-yl]carbonyl}pyrrolidin-3-yl)phenyl]pyridine | R,S,R,S or S,R,R,S or S,R,S,R or R,S,S,R | 487.65 | Int. 1A, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 92 | 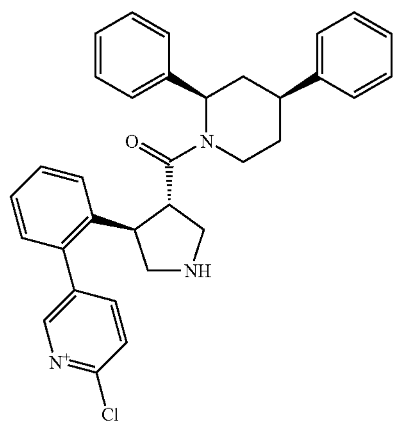 [SMILES: O=C([C@@H]1CNC[C@H]1c1ccccc1-c1ccc(Cl)[nH+]c1)N1CC[C@H](c2ccccc2)C[C@@H]1c1ccccc1] | 2-chloro-5-[2((3R,4S)-4-{[2R,4S)-2,4-diphenylpiperidin-1-yl]carbonyl}pyrrolidin-3-yl)phenyl]pyridine | R,S,R,S or S,R,R,S or S,R,S,R or R,S,S,R | 522.095 | Int. 1A, Int. 9, Scheme B, Scheme C, Ex2 |
| 93 | 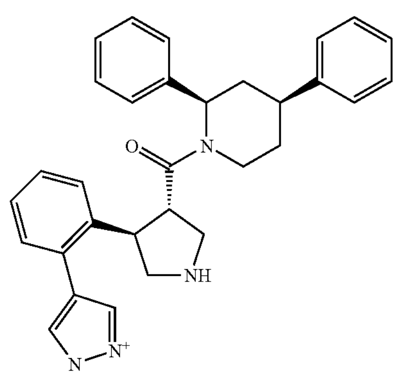 [SMILES: O=C([C@@H]1CNC[C@H]1c1ccccc1-c1c[nH][nH+]c1)N1CC[C@H](c2ccccc2)C[C@@H]1c1ccccc1] | (2R,4S)-2,4-diphenyl-1-({(3S,4R)-4-[2-(1H-pyrazol-4-yl)phenyl]pyrrolidin-3-yl}carbonyl)piperidine | R,S,R,S or S,R,R,S or S,R,S,R or R,S,S,R | 476.627 | Int. 1A, Int. 9, Scheme B, Scheme C, Ex2 |
| 94 | 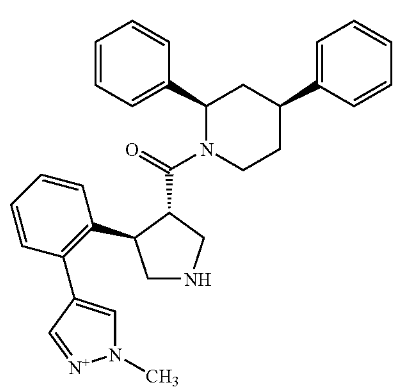 [SMILES: Cn1cc(-c2ccccc2[C@@H]2CNC[C@H]2C(=O)N2CC[C@H](c3ccccc3)C[C@@H]2c2ccccc2)c[nH+]1] | (2R,4S)-1-({(3S,4R)-4-[2-(1-methyl-1H-pyrazol-4-yl)phenyl]pyrrolidin-3-yl}carbonyl)-2,4-diphenylpiperidine | R,S,R,S or S,R,R,S or S,R,S,R or R,S,S,R | 490.654 | Int. 1A, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 95 | 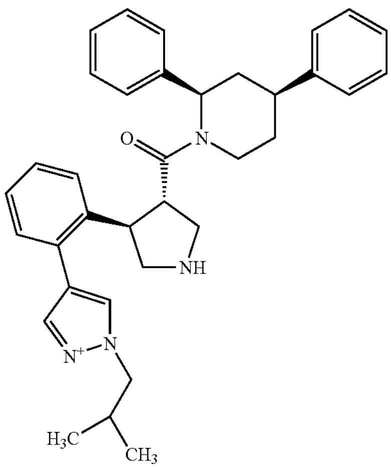 [SMILES: CC(C)Cn1cc(-c2ccccc2[C@@H]2CNC[C@H]2C(=O)N2CC[C@H](c3ccccc3)C[C@@H]2c2ccccc2)c[nH+]1] | (2R,4S)-1-({(3S,4R)-4-[2-(1-isobutyl-1H-pyrazol-4-yl)phenyl]pyrrolidin-3-yl}carbonyl)-2,4-diphenylpiperidine | R,S,R,S or S,R,R,S or S,R,S,R or R,S,S,R | 532.735 | Int. 1A, Int. 9, Scheme B, Scheme C, Ex2 |
| 96 | 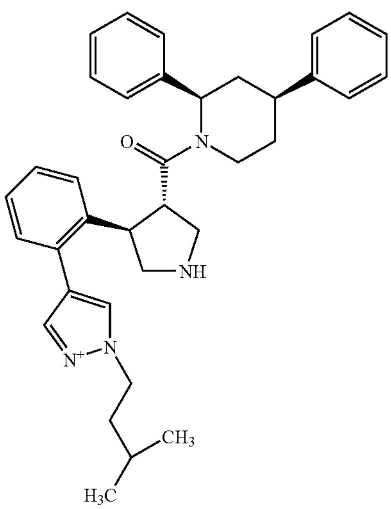 [SMILES: CC(C)CCn1cc(-c2ccccc2[C@@H]2CNC[C@H]2C(=O)N2CC[C@H](c3ccccc3)C[C@@H]2c2ccccc2)c[nH+]1] | (2R,4S)-1-[((3S,4R)-4-{2-[1-(3-methylbutyl)-1H-pyrazol-4-yl]phenyl}pyrrolidin-3-yl)carbonyl]-2,4-diphenylpiperidine | R,S,R,S or S,R,R,S or S,R,S,R or R,S,S,R | 546.762 | Int. 1A, Int. 9, Scheme B, Scheme C, Ex2 |
| 97 | 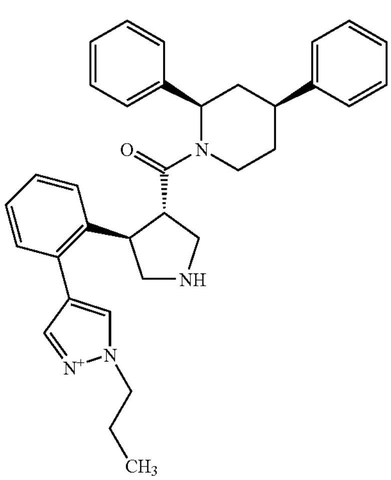 [SMILES: CCCn1cc(-c2ccccc2[C@@H]2CNC[C@H]2C(=O)N2CC[C@H](c3ccccc3)C[C@@H]2c2ccccc2)c[nH+]1] | (2R,4S)-2,4-diphenyl-1-({(3S,4R)-4-[2-(1-propyl-1H-pyrazol-4-yl)phenyl]pyrrolidin-3-yl}carbonyl)piperidine | R,S,R,S or S,R,R,S or S,R,S,R or R,S,S,R | 518.708 | Int. 1A, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 98 | 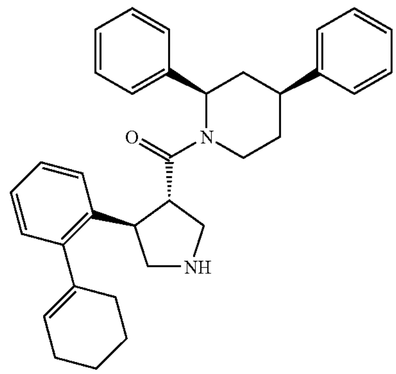 [SMILES: O=C([C@@H]1CNC[C@H]1c1ccccc1C1=CCCCC1)N1CC[C@H](c2ccccc2)C[C@@H]1c1ccccc1] | (2R,4S)-1-{[(3S,4R)-4-(2-cyclohex-1-en-1-ylphenyl)pyrrolidin-3-yl]carbonyl}-2,4-diphenylpiperidine | R,S,R,S or S,R,R,S or S,R,S,R or R,S,S,R | 490.695 | Int. 1A, Int. 9, Scheme B, Scheme C, Ex2 |
| 99 | 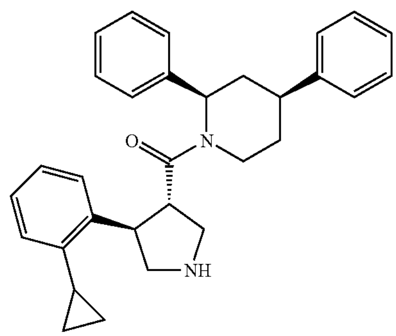 [SMILES: O=C([C@@H]1CNC[C@H]1c1ccccc1C1CC1)N1CC[C@H](c2ccccc2)C[C@@H]1c1ccccc1] | (2R,4S)-1-{[(3S,4R)-4-(2-cyclopropylphenyl)pyrrolidin-3-yl]carbonyl}-2,4-diphenylpiperidine | R,S,R,S or S,R,R,S or S,R,S,R or R,S,S,R | 450.629 | Int. 1A, Int. 9, Scheme B, Scheme C, Ex2 |
| 100 | 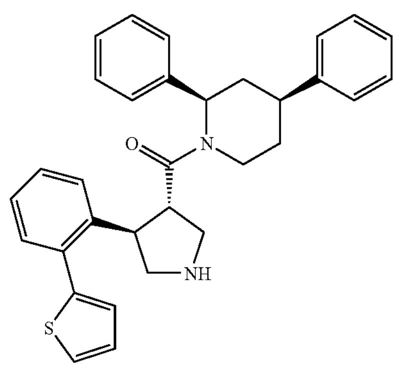 [SMILES: O=C([C@@H]1CNC[C@H]1c1ccccc1-c1cccs1)N1CC[C@H](c2ccccc2)C[C@@H]1c1ccccc1] | (2R,4S)-2,4-diphenyl-1-({(3S,4R)-4-[2-(2-thienyl)phenyl]pyrrolidin-3-yl}carbonyl)piperidine | R,S,R,S or S,R,R,S or S,R,S,R or R,S,S,R | 429.689 | Int. 1A, Int. 9, Scheme B, Scheme C, Ex2 |
| 101 | 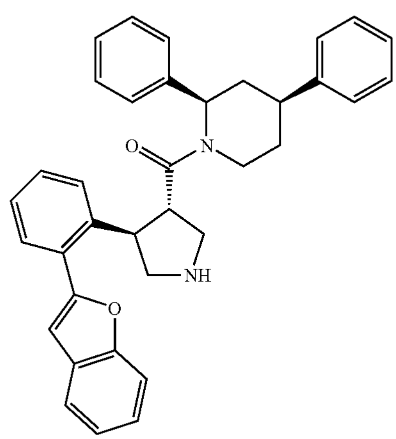 [SMILES: O=C([C@@H]1CNC[C@H]1c1ccccc1-c1cc2ccccc2o1)N1CC[C@H](c2ccccc2)C[C@@H]1c1ccccc1] | (2R,4S)-1-({(3S,4R)-4-[2-(1-benzofuran-2-yl)phenyl]pyrrolidin-3-yl}carbonyl)-2,4-diphenylpiperidine | R,S,R,S or S,R,R,S or S,R,S,R or R,S,S,R | 526.685 | Int. 1A, Int. 9, Scheme B, Scheme C, Ex2 |

TABLE 2-continued

| Ex | Structure | Chemical Name | Stereochemistry | Parent Weight | Intermed., Scheme and reference example |
|---|---|---|---|---|---|
| 102 | 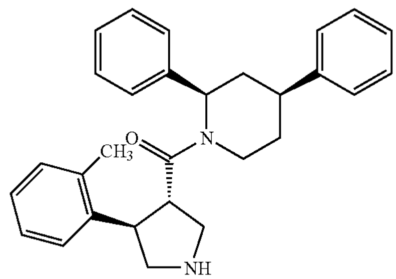 [SMILES: Cc1ccccc1[C@@H]1CNC[C@H]1C(=O)N1CC[C@H](c2ccccc2)C[C@@H]1c1ccccc1] | (2R,4S)-1-{[(3S,4R)-4-(2-methylphenyl)pyrrolidin-3-yl]carbonyl}-2,4-diphenylpiperidine | R,S,R,S or S,R,R,S or S,R,S,R or R,S,S,R | 424.591 | Int. 1A, Int. 9, Scheme B, Scheme C, Ex2 |
| 103 | 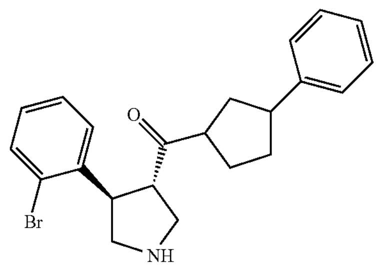 [SMILES: O=C(C1CCC(c2ccccc2)C1)[C@@H]1CNC[C@H]1c1ccccc1Br] | 1-{[(3S,4R)-4-(2-bromophenyl)pyrrolidin-3-yl]carbonyl}-3-phenylpyrrolidine | R,S,RS or S,R,RS | 399.334 | Int. 9, Scheme B, Ex2 |
| 104 | 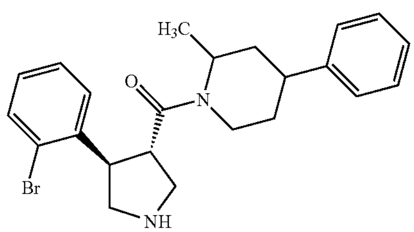 [SMILES: CC1CC(c2ccccc2)CCN1C(=O)[C@@H]1CNC[C@H]1c1ccccc1Br] | 1-{[(3S,4R)-4-(2-bromophenyl)pyrrolidin-3-yl]carbonyl}-2-methyl-4-phenylpiperidine | Mixture of 4 Diastereomers | 427.388 | Int. 1B, Int. 9, Scheme B, Ex2 |
| 105 | 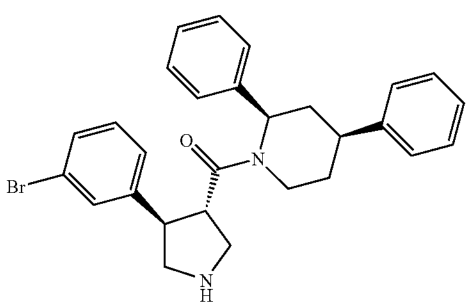 [SMILES: O=C([C@@H]1CNC[C@H]1c1cccc(Br)c1)N1CC[C@H](c2ccccc2)C[C@@H]1c1ccccc1] | (2R,4S)-1-{[(3S,4R)-4-(3-bromophenyl)pyrrolidin-3-yl]carbonyl}-2,4-diphenylpiperidine | R,S,R,S and S,R,R,S | 489.46 | Int. 1A, Scheme B, Ex2 |
| 106 | 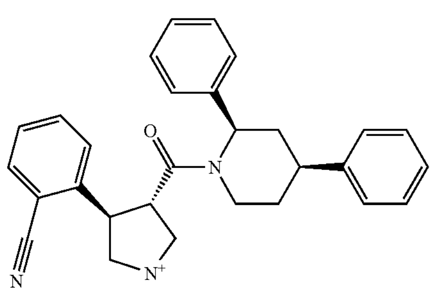 [SMILES: N#Cc1ccccc1[C@@H]1C[NH2+]C[C@H]1C(=O)N1CC[C@H](c2ccccc2)C[C@@H]1c1ccccc1] | 2-((3R,4S)-4-{[(2R,4S)-2,4-diphenylpiperidin-1-yl]carbonyl}pyrrolidin-3-yl)benzonitrile | R,S,R,S or S,R,R,S or S,R,S,R or R,S,S,R | 435.574 | Int. 1A, Scheme B, Ex2 |

TABLE 2-continued

| Ex | Structure | Chemical Name | Stereochemistry | Parent Weight | Intermed., Scheme and reference example |
|---|---|---|---|---|---|
| 107 | 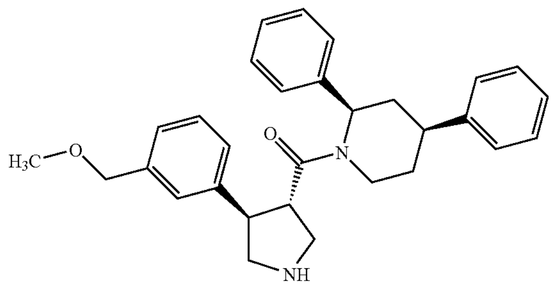 [SMILES: COCc1cccc([C@@H]2CNC[C@H]2C(=O)N2CC[C@H](c3ccccc3)C[C@@H]2c2ccccc2)c1] | (2R,4S)-1-({(3S,4R)-4-[3-(methoxymethyl) phenyl]pyrrolidin-3-yl} carbonyl)-2,4-diphenylpiperidine | R,S,R,S and S,R,R,S | 454.618 | Int. 1A, Scheme B, Ex2 |
| 108 | 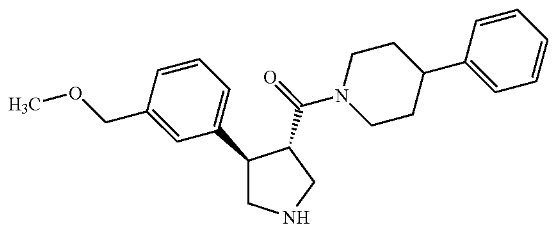 [SMILES: COCc1cccc([C@@H]2CNC[C@H]2C(=O)N2CCC(c3ccccc3)CC2)c1] | 1-({(3S,4R)-4-[3-(methoxymethyl)phenyl] pyrrolidin-3-yl} carbonyl)-4-phenylpiperidine | R,S and S,R | 378.519 | Int. 1A, Scheme B, Ex2 |
| 109 | 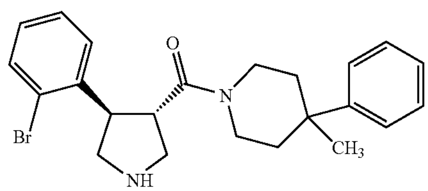 [SMILES: CC1(c2ccccc2)CCN(C(=O)[C@@H]2CNC[C@H]2c2ccccc2Br)CC1] | 1-{[(3S,4R)-4-(2-bromophenyl) pyrrolidin-3-yl]carbonyl}-4-methyl-4-phenylpiperidine | R,S or S,R | 427.388 | Int. 9, Scheme B |
| 110 | 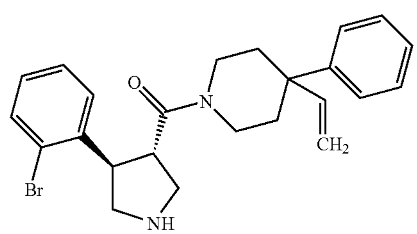 [SMILES: C=CC1(c2ccccc2)CCN(C(=O)[C@@H]2CNC[C@H]2c2ccccc2Br)CC1] | 1-{[(3S,4R)-4-(2-bromophenyl) pyrrolidin-3-yl] carbonyl}-4-phenyl-4-vinylpiperidine | R,S or S,R | 439.4 | Int. 9, Scheme B |
| 111 | 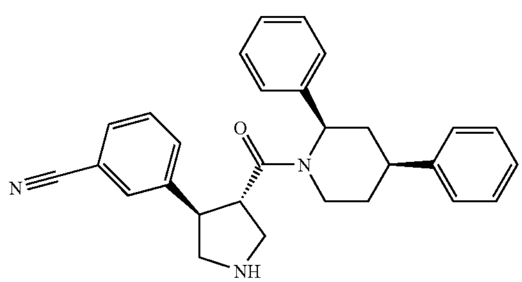 [SMILES: N#Cc1cccc([C@@H]2CNC[C@H]2C(=O)N2CC[C@H](c3ccccc3)C[C@@H]2c2ccccc2)c1] | 3-((3R,4S)-4-{[(2R,4S)-2,4-diphenylpiperidin-1-yl] carbonyl}pyrrolidin-3-yl)benzonitrile | R,S,R,S and S,R,R,S | 435.574 | Int. 1A, Scheme B, Ex2 |
| 112 | 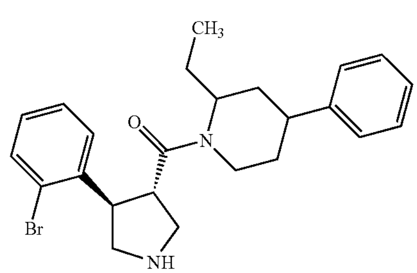 [SMILES: CCC1CC(c2ccccc2)CCN1C(=O)[C@@H]1CNC[C@H]1c1ccccc1Br] | 1-{[(3S,4R)-4-(2-bromophenyl)pyrrolidin-3-yl]carbonyl}-2-ethyl-4-phenylpiperidine | Mixture of 4 Diastereomers | 441.416 | Int. 1D Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 113 | 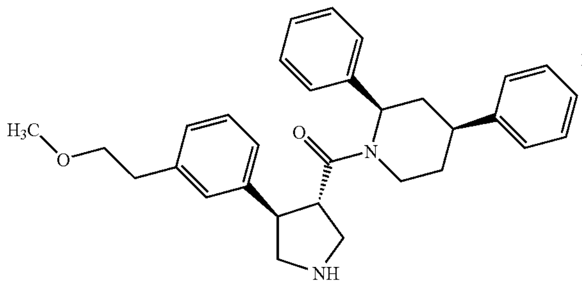 | (2R,4S)-1-({(3S,4R)-4-[3-(2-methoxyethyl)phenyl]pyrrolidin-3-yl}carbonyl)-2,4-diphenylpiperidine | Trans Recemic at Pyrrolidine | 468.645 | Int. 1A, Scheme B, Ex2 |
| 114 | 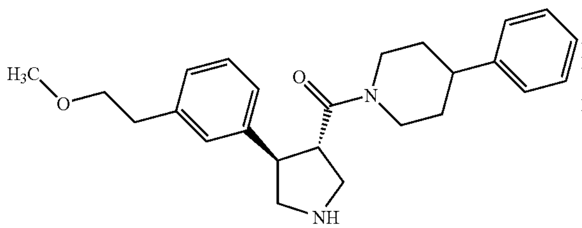 | 1-({(3S,4R)-4-[3-(2-methoxyethyl)phenyl]pyrrolidin-3-yl}carbonyl)-4-phenylpiperidine | R,S and S,R | 392.546 | Scheme B, Ex2 |
| 115 | 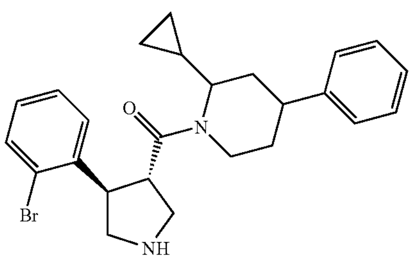 [SMILES: O=C([C@@H]1CNC[C@H]1c1ccccc1Br)N1CCC(c2ccccc2)CC1C1CC1] | 1-{[(3S,4R)-4-(2-bromophenyl)pyrrolidin-3-yl]carbonyl}-2-cyclopropyl-4-phenylpiperidine | Mixture of 4 Diastereomers | 453.427 | Int. 1E, Int. 9, Scheme B, Ex2 |
| 116 | 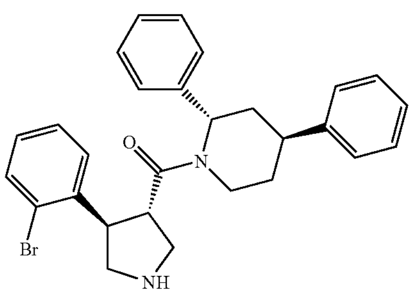 [SMILES: O=C([C@@H]1CNC[C@H]1c1ccccc1Br)N1CC[C@H](c2ccccc2)C[C@H]1c1ccccc1] | (2S,4S)-1-{[(3S,4R)-4-(2-bromophenyl)pyrrolidin-3-yl]carbonyl}-2,4-diphenylpiperidine | R,S and S,R at Pyrrolidine, Trans Racemic at Piperidine | 489.46 | Int. 1A, Scheme B, Ex2 |
| 117 | 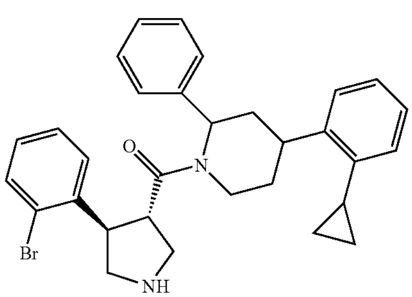 [SMILES: O=C([C@@H]1CNC[C@H]1c1ccccc1Br)N1CCC(c2ccccc2C2CC2)CC1c1ccccc1] | 1-{[(3S,4R)-4-(2-bromophenyl)pyrrolidin-3-yl]carbonyl}-4-(2-cyclopropylphenyl)-2-phenylpiperidine | R,S and S,R at Pyrrolidine, Mixture of 4 Diastereomers at Piperidine | 529.525 | Int. 9, Scheme B |

TABLE 2-continued

| Ex | Structure | Chemical Name | Stereochemistry | Parent Weight | Intermed., Scheme and reference example |
|---|---|---|---|---|---|
| 118 | 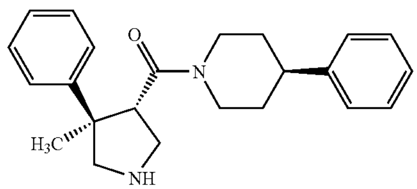 | 1-{[(3S,4R)-4-methyl-4-phenylpyrrolidine-3-yl]carbonyl}-4-phenylpiperidine | R,S and S,R | 348.492 | Scheme D |
| 119 | 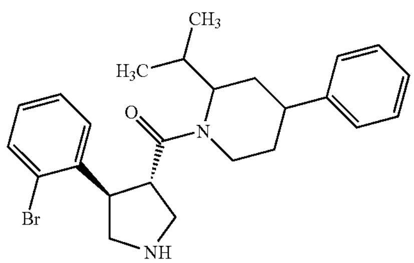 [SMILES: CC(C)C1CC(c2ccccc2)CCN1C(=O)[C@@H]1CNC[C@H]1c1ccccc1Br] | 1-{[(3S,4R)-4-(2-bromophenyl)pyrrolidin-3-yl]carbonyl}-2-isopropyl-4-phenylpiperidine | Mixture of 4 Diastereomers | 455.443 | Int. 1C, Int. 9, Scheme B, Ex2 |
| 120 | 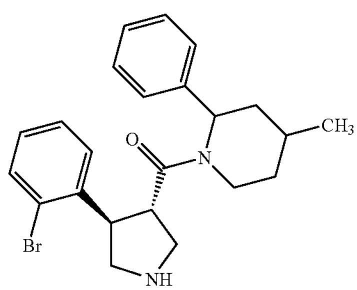 [SMILES: CC1CCN(C(=O)[C@@H]2CNC[C@H]2c2ccccc2Br)C(c2ccccc2)C1] | 1-{[(3S,4R)-4-(2-bromophenyl)pyrrolidin-3-yl]carbonyl}-4-methyl-2-phenylpiperidine | Mixture of 4 Diastereomers | 427.388 | Int. 9, Scheme B |
| 121 | 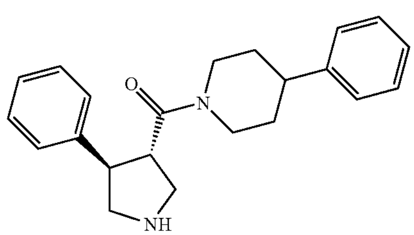 [SMILES: O=C([C@@H]1CNC[C@H]1c1ccccc1)N1CCC(c2ccccc2)CC1] | 4-phenyl-1-{[(3S,4R)-4-phenylpyrrolidin-3-yl]carbonyl}piperidine | 3S,4R | 334.465 | Scheme A |
| 122 | 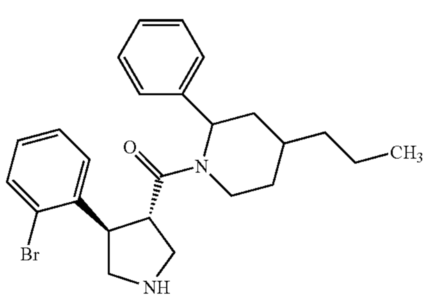 [SMILES: CCCC1CCN(C(=O)[C@@H]2CNC[C@H]2c2ccccc2Br)C(c2ccccc2)C1] | 1-{[(3S,4R)-4-(2-bromophenyl)pyrrolidin-3-yl]carbonyl}-2-phenyl-4-propylpiperidine | R,S and S,R at Pyrrolidine, Mixture of 4 Diastereomers at Piperidine | 455.443 | Int. 9, Scheme B |
| 123 | 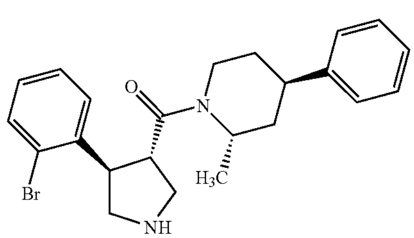 [SMILES: C[C@H]1C[C@H](c2ccccc2)CCN1C(=O)[C@@H]1CNC[C@H]1c1ccccc1Br] | (2S,4R)-1-{[(3S,4R)-4-(2-bromophenyl)pyrrolidin-3-yl]carbonyl}-2-methyl-4-phenylpiperidine | R,S and S,R at Pyrrolidine, Trans Racemic at Piperidine | 427.388 | Int. 1B, Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 124 | 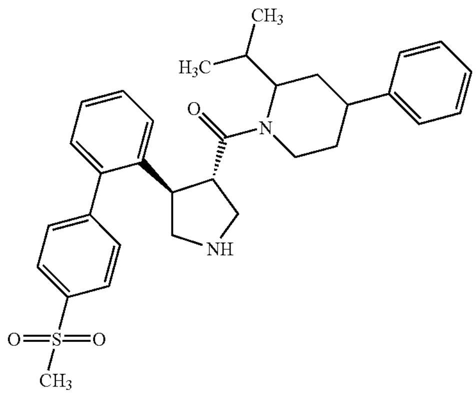 [SMILES: CC(C)C1CC(c2ccccc2)CCN1C(=O)[C@@H]1CNC[C@H]1c1ccccc1-c1ccc(S(C)(=O)=O)cc1] | 2-isopropyl-1-({[(3S,4R)-4-[4'-(methylsulfonyl)biphenyl-2-yl]pyrrolidin-3-yl}carbonyl)-4-phenylpiperidine | 3S,4R, Racemic at Isopropyl | 530.735 | Int. 1C, Int. 9, Scheme B, Scheme C, Ex2 |
| 125 | 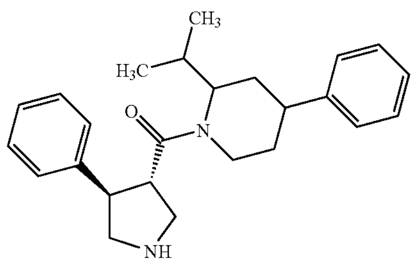 [SMILES: CC(C)C1CC(c2ccccc2)CCN1C(=O)[C@@H]1CNC[C@H]1c1ccccc1] | 2-isopropyl-4-phenyl-1-{[(3S,4R)-4-phenylpyrrolidin-3-yl]carbonyl}piperidine | 3S,4R, Racemic at Isopropyl | 376.547 | Scheme A |
| 126 | 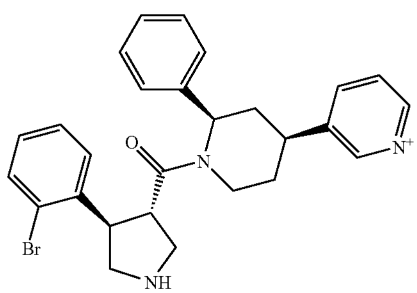 [SMILES: O=C([C@@H]1CNC[C@H]1c1ccccc1Br)N1CC[C@H](c2ccc[nH+]c2)C[C@@H]1c1ccccc1] | 3-((2R,4S)-1-{[(3S,4R)-4-(2-bromophenyl)pyrrolidin-3-yl]carbonyl}-2-phenylpiperidin-4-yl)pyridine | 3S,4R, Racemic cis at Isopropyl | 490.448 | Int. 9, Scheme B |
| 127 | 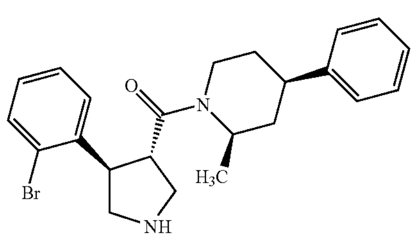 [SMILES: C[C@@H]1C[C@H](c2ccccc2)CCN1C(=O)[C@@H]1CNC[C@H]1c1ccccc1Br] | (2R,4R)-1-{[(3S,4R)-4-(2-bromophenyl)pyrrolidin-3-yl]carbonyl}-2-methyl-4-phenylpiperidine | 3S,4R, cis Racemic at Isopropyl | 427.388 | Int. 1B, Int. 9, Scheme B, Ex2 |
| 128 | 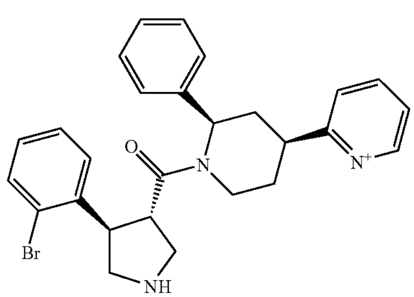 [SMILES: O=C([C@@H]1CNC[C@H]1c1ccccc1Br)N1CC[C@H](c2cccc[nH+]2)C[C@@H]1c1ccccc1] | 2-((2R,4S)-1-{[(3S,4R)-4-(2-bromophenyl)pyrrolidin-3-yl]carbonyl}-2-phenylpiperidin-4-yl)pyridine | 3S,4R, cis Racemic at Isopropyl | 490.448 | Int. 9, Scheme B |

TABLE 2-continued

| Ex | Structure | Chemical Name | Stereochemistry | Parent Weight | Intermed., Scheme and reference example |
|---|---|---|---|---|---|
| 129 | 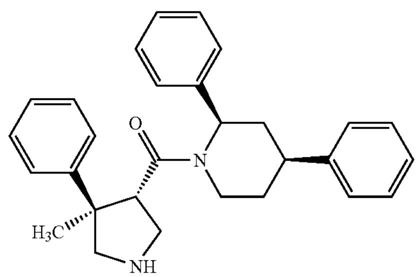 [SMILES: C[C@@]1(c2ccccc2)CNC[C@H]1C(=O)N1CC[C@H](c2ccccc2)C[C@@H]1c1ccccc1] | (2R,4S)-1-{[(3S,4R)-4-methyl-4-phenylpyrrolidin-3-yl]carbonyl}-2,4-diphenylpiperidine | R,S cis and S,R, cis | 424.591 | Scheme D |
| 130 | 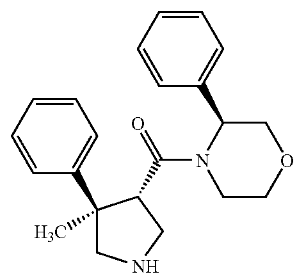 [SMILES: C[C@@]1(c2ccccc2)CNC[C@H]1C(=O)N1CCOC[C@@H]1c1ccccc1] | (3S)-4-{[(3S,4R)-4-methyl-4-phenylpyrrolidin-3-yl]carbonyl}-3-phenylmorpholine | R,S,S and S,R,S | 350.465 | Scheme D |
| 131 | 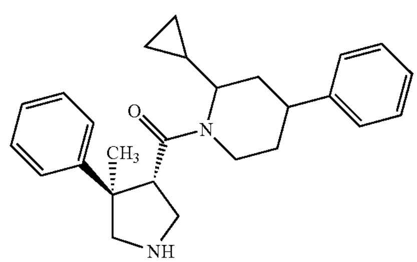 [SMILES: C[C@@]1(c2ccccc2)CNC[C@H]1C(=O)N1CCC(c2ccccc2)CC1C1CC1] | 2-cyclopropyl-1-{[(3S,4R)-4-methyl-4-phenylpyrrolidin-3-yl]carbonyl}-4-phenylpiperidine | Mixture of 8 Diastereomers | 388.558 | Scheme D |
| 132 | 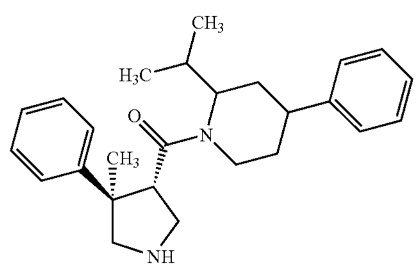 [SMILES: CC(C)C1CC(c2ccccc2)CCN1C(=O)[C@@H]1CNC[C@@]1(C)c1ccccc1] | 2-isopropyl-1-{[(3S,4R)-4-methyl-4-phenylpyrrolidin-3-yl]carbonyl}-4-phenylpiperidine | Mixture of 8 Diastereomers | 390.574 | Scheme D |
| 133 | 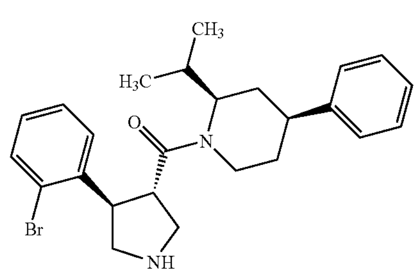 [SMILES: CC(C)[C@H]1C[C@@H](c2ccccc2)CCN1C(=O)[C@@H]1CNC[C@H]1c1ccccc1Br] | (2R,4S)-1-{[(3S,4R)-4-(2-bromophenyl)pyrrolidin-3-yl]carbonyl}-2-isopropyl-4-phenylpiperidine | 3S,4R, cis Racemic at Piperidine | 455.443 | Int. 1C, Int. 9, Scheme B, Ex2 |

TABLE 2-continued

| Ex | Structure | Chemical Name | Stereochemistry | Parent Weight | Intermed., Scheme and reference example |
|---|---|---|---|---|---|
| 134 | 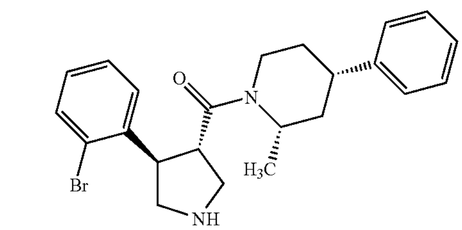 [SMILES: C[C@H]1C[C@@H](c2ccccc2)CCN1C(=O)[C@@H]1CNC[C@H]1c1ccccc1Br] | (2S,4S)-1-{[(3S,4R)-4-(2-bromophenyl)pyrrolidin-3-yl]carbonyl}-2-methyl-4-phenylpiperidine | 3S,4R;S,S (piperidine) | 427.388 | Int. 1B, Int. 9, Scheme B, Ex2 |
| 135 | 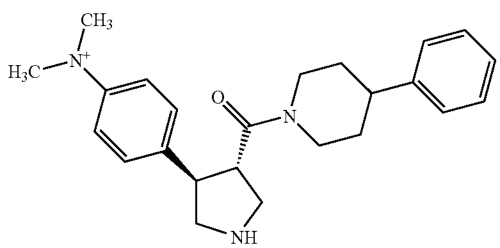 [SMILES: C[NH+](C)c1ccc([C@@H]2CNC[C@H]2C(=O)N2CCC(c3ccccc3)CC2)cc1] | N,N-dimethyl-4-{(3R,4S)-4-[(4-phenylpiperidin-1-yl)carbonyl]pyrrolidin-3-yl}aniline | 3S,4R and 3R,4S | 377.534 | Scheme B, Ex2 |

Compounds in Table 2 having a basic group or acidic group are depicted and named as the free base acid. Depending on the reaction and purification conditions, various compounds in Table 1 having a basic group were isolated in either the free base form, or as a salt (such as HCl salt), or in both free base and salt forms.

The following abbreviations are used throughout the text:

| | |
|---|---|
| Me: | methyl |
| Et: | ethyl |
| Bu: | butyl |
| t-Bu: | tert-butyl |
| i-Bu: | iso-butyl |
| Pr: | propyl |
| i-Pr: | iso-propyl |
| Ar: | aryl |
| Ph: | phenyl |
| Bn: | benzyl |
| Cbz: | carbobenzyloxy |
| LAH: | lithium aluminum hydride |
| DCM: | dichloromethane |
| DCE: | dichloroethane |
| DMA: | dimethylacetamide |
| BOP: | benzotriazolyl-N-oxy-tris(dimethylamino)phosphonium hexaflurophosphate |
| Boc: | tert butyloxycarbonyl |
| TFA: | trifluoro acetic acid |
| THF: | tetrahydrofuran |
| Ac: | acetyl |
| aq: | aqueous |
| rt: | room temperature |
| h: | hours |
| min: | minutes |

What is claimed is:
1. A compound of formula (I)

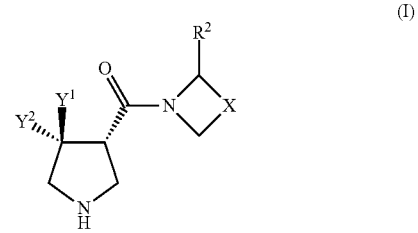

$Y^1$ is phenyl, which is optionally substituted with one or more
(a) —$C_{1-6}$alkyl,
(b) —$C_{1-6}$alkyl-$C_{3-6}$cycloalkyl,
(c) —$C_{6-10}$aryl,
(d) halogen,
(e) —O—$C_{1-6}$alkyl,
(f) —CN,
(g) a heterocyclic group having 4 to 8 ring atoms, wherein one ring atom is a heteroatom selected from the group consisting of nitrogen, sulfur or oxygen, and
(h) heteroaryl,
and wherein said alkyl, aryl, cycloalkyl, heterocyclic, or heteroaryl moiety is optionally substituted with one or more
(i) halo,
(ii) —OH,
(iii) —CN,
(iv) —$C_{1-6}$ alkyl,
(v) —$C_{2-6}$ alkenyl,
(vi) —$C_{3-6}$ cycloalkyl,
(vii) —O—$C_{1-6}$ alkyl, (viii) —O—(CH$_2$)$_p$-aryl,
(ix) aryl,
(x) heteroaryl,
(xi) —NR$^{6A}$R$^{6B}$,
(xii) —C(=O)—R$^{6C}$,
(xiii) —C(=O)—NR$^{6A}$R$^{6B}$,
(xiv) —NR$^{6A}$(C=O)R$^{6B}$,
(xiv) —C(=O)—OR$^{6C}$,
(xv) —NSO$_2$R$^{6A}$R$^{6B}$,
(xvi) —SO$_2$—R$^{6C}$,
(xvii) —(SO$_2$)NR$^{6A}$R$^{6B}$,
wherein R$^{6A}$ and R$^{6B}$ are selected from the group consisting of
(I) hydrogen,
(II) —C$_{1-6}$ alkyl,
(III) —C$_{3-6}$ cycloalkyl,
or R$^{6A}$ and R$^{6B}$ are linked together with the nitrogen to which they are both attached to form a 2-6 membered carbocyclic ring,
wherein one or two of the ring carbon atoms is replaced by a nitrogen, oxygen or sulfur,
and R$^{6C}$ is selected from the group consisting of
(I) hydrogen,
(II) —C$_{1-6}$ alkyl, and
(III) —C$_{3-6}$ cycloalkyl;
Y$^2$ is hydrogen or methyl;
R$^2$ is selected from the group consisting of
(1) hydrogen
(2) C$_{1-6}$alkyl,
(3) —C$_{1-6}$alkyl-C$_{3-6}$cycloalkyl,
(4) —(CH$_2$)$_m$aryl,
(5) heteroaryl,
(6) —O—C$_{1-6}$ alkyl,
(7) —C(=O)—OR$^{6C}$, and
(8) a heterocyclic group having 4 to 8 ring atoms, wherein one ring atom is a heteroatom selected from the group consisting of nitrogen, sulfur or oxygen, and
wherein said alkyl, aryl, cycloalkyl, heterocyclic or heteroaryl R$^2$ moiety is optionally substituted with one or more
(a) halo,
(b) —OH,
(c) —CN,
(d) —C$_{1-6}$ alkyl
(e) —C$_{3-6}$ cycloalkyl,
(f) —O—C$_{1-6}$ alkyl,
(g) —O—CH$_2$-aryl,
(h) aryl,
(i) heteroaryl,
(j) —NR$^{6A}$R$^{6B}$,
(k) —NR$^{6A}$C(=O)R$^{6B}$,
(l) a heterocyclic group having 4 to 8 ring atoms, wherein one ring atom is a heteroatom selected from the group consisting of nitrogen, sulfur and oxygen,
(m) —SO$_2$C$_{1-3}$ alkyl,
(n) —SO$_2$NR$^{6A}$R$^{6B}$,
(o) —CONR$^{6A}$R$^{6B}$, and
(p) a heterocyclic group having 4 to 8 ring atoms, wherein one ring atom is a heteroatom selected from the group consisting of nitrogen, sulfur and oxygen;
wherein R$^{6A}$ and R$^{6B}$ are selected from the group consisting of
(I) hydrogen,
(II) —C$_{1-6}$ alkyl,
(III) —C$_{3-6}$ cycloalkyl,
or R$^{6A}$ and R$^{6B}$ are linked together with the nitrogen to which they are both attached to form a 2-6 membered carbocyclic ring,
wherein one or two of the ring carbon atoms is replaced by a nitrogen, oxygen or sulfur,
and R$^{6C}$ is selected from the group consisting of
(I) hydrogen,
(II) —C$_{1-6}$ alkyl, and
(III) —C$_{3-6}$ cycloalkyl;
X is selected from the group consisting of
(1) —CR$^5$R$^6$—O—CR$^7$R$^8$—
(2) —CR$^5$R$^6$CR$^7$R$^8$—O—CR$^9$R$^{10}$—
(3) —CR$^5$R$^6$—
(4) —CR$^5$R$^6$CR$^7$R$^8$—
(5) —CH$_2$CR$^7$R$^8$CH$_2$—
(6) —CR$^5$=CR$^6$CR$^7$R$^8$—
(7) —CR$^5$R$^6$CR$^7$R$^8$CR$^9$R$^{10}$CR$^{11}$R$^{12}$—;
R$^5$, R$^6$, R$^7$, R$^8$, R$^9$, R$^{10}$, R$^{11}$ and R$^{12}$ are independently selected from the group consisting of:
(1) hydrogen,
(2) C$_{1-6}$alkyl,
(3) OH
(4) —(CH$_2$)$_m$aryl
wherein said alkyl or aryl moiety is optionally substituted with one or more
(a) halo,
(b) —C$_{1-6}$ alkyl,
(c) —O—C$_{1-6}$ alkyl, and
(d) -aryl,
wherein said wherein said alky or aryl is optionally substituted with one or more halo,
or R$^5$ and R$^6$, or R$^7$ and R$^8$, or R$^9$ and R$^{10}$, or R$^{11}$ and R$^{12}$ are linked together to form an aromatic or non-aromatic spirocyclic group of 5-10 ring carbon atoms, wherein one or two of the ring carbon atoms is replaced by an oxygen, nitrogen or sulfur,
or R$^5$ and R$^6$, and R$^7$ and R$^8$, are linked together to form to form a fused aromatic or non-aromatic cyclic group of 5-10 ring carbon atoms, wherein one or two of the ring carbon atoms is replaced by an oxygen, nitrogen or sulfur,
or R$^2$ and R$^5$ are linked together to form to form a fused aromatic or non-aromatic cyclic group of 5-10 ring carbon atoms, wherein one or two of the ring carbon atoms is replaced by an oxygen, nitrogen or sulfur;
m is 0, 1 or 2;
p is 0 or 1;
or a pharmaceutically acceptable salt thereof.

2. A compound of claim 1, or a pharmaceutically acceptable salt thereof, wherein Y$^1$ is phenyl, which is substituted by one or more
(1) —C$_{1-6}$alkyl, wherein said alkyl is optionally substituted with one or more fluoro,
(2) halogen, and
(3) —O—C$_{1-6}$alkyl, wherein said alkyl is optionally substituted with one or more fluoro.

3. A compound of claim 1, or a pharmaceutically acceptable salt thereof, wherein Y$^1$ is phenyl, which is substituted by one or more phenyl, wherein said phenyl is optionally substituted with one or more
(a) halo,
(b) —OH,
(c) —CN,
(d) —C$_{1-6}$ alkyl,
(e) —C$_{2-6}$ alkenyl,
(f) —C$_{3-6}$ cycloalkyl,
(g) —O—C$_{1-6}$ alkyl, (h) —O—(CH$_2$)$_p$-aryl,
(i) aryl,
(j) heteroaryl,
(k) —NR$^{6A}$R$^{6B}$,
(l) —C(=O)—R$^{6C}$,
(m) —C(=O)—NR$^{6A}$R$^{6B}$,
(n) —NR$^{6A}$(C=O)R$^{6B}$,
(o) —C(=O)—OR$^{6C}$,
(p) —NSO$_2$R$^{6A}$R$^{6B}$,
(q) —SO$_2$—R$^{6C}$, and
(r) —(SO$_2$)NR$^{6A}$R$^{6B}$.

4. A compound of claim 1, or a pharmaceutically acceptable salt thereof, wherein Y$^2$ is hydrogen.

5. A compound of claim 1, or a pharmaceutically acceptable salt thereof, wherein R$^2$ is selected from the group consisting of:
(1) phenyl, and
(2) benzyl.

6. A compound of claim 1, or a pharmaceutically acceptable salt thereof, wherein X is selected from the group consisting of
(1) —CR$^5$R$^6$—O—CR$^7$R$^8$—,
(2) —CR$^5$R$^6$CR$^7$R$^8$—O—CR$^9$R$^{10}$—,
(3) —CR$^5$R$^6$CR$^7$R$^8$—, and
(4) —CR$^5$R$^6$CR$^7$R$^8$CR$^9$R$^{10}$—.

7. A compound of claim 1, or a pharmaceutically acceptable salt thereof,
wherein the compound of formula (I) is a compound of formula (II)

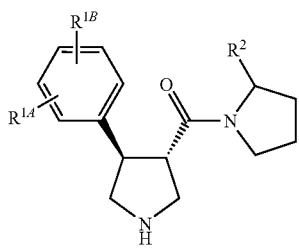

(II)

or a pharmaceutically acceptable salt thereof,
wherein R$^{1A}$ and R$^{1B}$ are selected from the group consisting of
(a) —C$_{1-6}$alkyl,
(b) —C$_{1-6}$alkyl-C$_{3-6}$cycloalkyl,
(c) —C$_{6-10}$aryl,
(d) halogen,
(e) —O—C$_{1-6}$alkyl,
(f) —CN,
(g) a heterocyclic group having 4 to 8 ring atoms, wherein one ring atom is a heteroatom selected from the group consisting of nitrogen, sulfur or oxygen, and
(h) heteroaryl,
and wherein said alkyl, aryl, cycloalkyl, heterocyclic, or heteroaryl moiety is optionally substituted with one or more
(i) halo,
(ii) —OH,
(iii) —CN,
(iv) —C$_{1-6}$ alkyl,
(v) —C$_{2-6}$ alkenyl,
(vi) —C$_{3-6}$ cycloalkyl,
(vii) —O—C$_{1-6}$ alkyl, (viii) —O—(CH$_2$)$_p$-aryl,
(ix) aryl,
(x) heteroaryl,
(xi) —NR$^{6A}$R$^{6B}$,
(xii) —C(=O)—R$^{6C}$,
(xiii) —C(=O)—NR$^{6A}$R$^{6B}$,
(xiv) —NR$^{6A}$(C=O)R$^{6B}$,
(xiv) —C(=O)—OR$^{6C}$,
(xv) —NSO$_2$R$^{6A}$R$^{6B}$,
(xvi) —SO$_2$—R$^{6C}$,
(xvii) —(SO$_2$)NR$^{6A}$R$^{6B}$,
wherein R$^{6A}$ and R$^{6B}$ are selected from the group consisting of
(I) hydrogen,
(II) —C$_{1-6}$ alkyl,
(III) —C$_{3-6}$ cycloalkyl,
or R$^{6A}$ and R$^{6B}$ are linked together with the nitrogen to which they are both attached to form a 2-6 membered carbocyclic ring, wherein one or two of the ring carbon atoms is replaced by a nitrogen, oxygen or sulfur,
and R$^{6C}$ is selected from the group consisting of
(I) hydrogen,
(II) —C$_{1-6}$ alkyl, and
(III) —C$_{3-6}$ cycloalkyl.

8. A compound of claim 1, or a pharmaceutically acceptable salt thereof,
wherein the compound of formula (I) is a compound of formula (III):

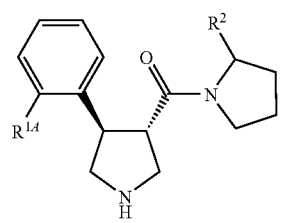

(III)

wherein R$^{1A}$ is selected from the group consisting of
(a) —C$_{1-6}$alkyl,
(b) —C$_{1-6}$alkyl-C$_{3-6}$cycloalkyl,
(c) —C$_{6-10}$aryl,
(d) halogen,
(e) —O—C$_{1-6}$alkyl,
(f) —CN,
(g) a heterocyclic group having 4 to 8 ring atoms, wherein one ring atom is a heteroatom selected from the group consisting of nitrogen, sulfur or oxygen, and
(h) heteroaryl,
and wherein said alkyl, aryl, cycloalkyl, heterocyclic, or heteroaryl moiety is optionally substituted with one or more
(i) halo,
(ii) —OH,
(iii) —CN,
(iv) —C$_{1-6}$ alkyl,
(v) —C$_{2-6}$ alkenyl,
(vi) —C$_{3-6}$ cycloalkyl,
(vii) —O—C$_{1-6}$ alkyl,
(viii) —O—(CH$_2$)$_p$-aryl,
(ix) aryl,
(x) heteroaryl, (xi) —NR$^{6A}$R$^{6B}$,
(xii) —C(=O)—R$^{6C}$,
(xiii) —C(=O)—NR$^{6A}$R$^{6B}$,
(xiv) —NR$^{6A}$(C=O)R$^{6B}$,
(xiv) —C(=O)—OR$^{6C}$,
(xv) —NSO$_2$R$^{6A}$R$^{6B}$,
(xvi) —SO$_2$—R$^{6C}$,
(xvii) —(SO$_2$)NR$^{6A}$R$^{6B}$,
wherein R$^{6A}$ and R$^{6B}$ are selected from the group consisting of
(I) hydrogen,
(II) —C$_{1-6}$ alkyl,
(III) —C$_{3-6}$ cycloalkyl,
or R$^{6A}$ and R$^{6B}$ are linked together with the nitrogen to which they are both attached to form a 2-6 membered carbocyclic ring, wherein one or two of the ring carbon atoms is replaced by a nitrogen, oxygen or sulfur,
and R$^{6C}$ is selected from the group consisting of
(I) hydrogen,
(II) —C$_{1-6}$ alkyl, and
(III) —C$_{3-6}$ cycloalkyl.

9. A compound of claim 8, wherein R$^{1A}$ is phenyl, which is unsubstituted or substituted with one or more groups selected from the group consisting of:
(i) halo,
(ii) —OH,
(iii) —CN,
(iv) —C$_{1-6}$ alkyl,
(v) —C$_{2-6}$ alkenyl,
(vi) —C$_{3-6}$ cycloalkyl,
(vii) —O—C$_{1-6}$ alkyl,
(viii) —O—(CH$_2$)$_p$-aryl,
(ix) aryl,
(x) heteroaryl,
(xi) —NR$^{6A}$R$^{6B}$,
(xii) —C(=O)—R$^{6C}$,
(xiii) —C(=O)—NR$^{6A}$R$^{6B}$,
(xiv) —NR$^{6A}$(C=O)R$^{6B}$,
(xiv) —C(=O)—OR$^{6C}$,
(xv) —NSO$_2$R$^{6A}$R$^{6B}$,
(xvi) —SO$_2$—R$^{6C}$,
(xvii) —(SO$_2$)NR$^{6A}$R$^{6B}$,
wherein R$^{6A}$ and R$^{6B}$ are selected from the group consisting of
(I) hydrogen,
(II) —C$_{1-6}$ alkyl,
(III) —C$_{3-6}$ cycloalkyl,
or R$^{6A}$ and R$^{6B}$ are linked together with the nitrogen to which they are both attached to form a 2-6 membered carbocyclic ring, wherein one or two of the ring carbon atoms is replaced by a nitrogen, oxygen or sulfur,
and R$^{6C}$ is selected from the group consisting of
(I) hydrogen,
(II) —C$_{1-6}$ alkyl, and
(III) —C$_{3-6}$ cycloalkyl.

10. A compound of claim 1, or a pharmaceutically acceptable salt thereof,
wherein the compound of formula (I) is a compound of formula (IV):

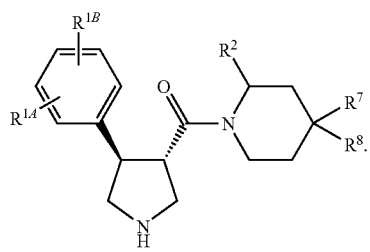

11. A compound of claim 1, or a pharmaceutically acceptable salt thereof,
wherein the compound of formula (I) is a compound of formula (V):

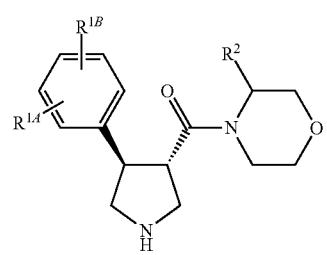

or a pharmaceutically acceptable salt thereof.

12. A compound of claim 1, or pharmaceutically acceptable salt thereof,
wherein the compound of formula (I) is a compound of formula (VI):

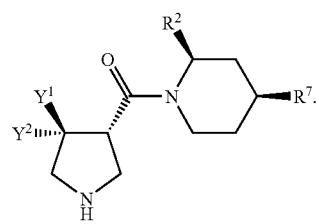

13. A compound of claim 1, which is selected from the group consisting of
2-benzyl-1-{[(3S,4R)-4-(2-methylphenyl)pyrrolidine-3-yl]carbonyl}pyrrolidine;
(3S)-4-{[3S,4R]-4-(2-bromophenyl)pyrrolidine-3-yl}carbonyl}-3-phenylmorpholine;
(3S)-4-{[3S,4R]-4-(4'-ethoxybiphenyl-2-yl)pyrrolidin-3-yl}carbonyl}-3-phenylmorpholine;
2-benzyl-1-{[(3S,4R)-4-(2-chlorophenyl)pyrrolidin-3-yl]carbonyl}pyrrolidine;
(3S)-4-{[(3S,4R)-4-(2-methoxyphenyl)pyrrolidin-3-yl]carbonyl}-3-phenylmorpholine;
2-benzyl-1-{[(3S,4R)-4-phenylpyrrolidin-3-yl]carbonyl}pyrrolidine;

(3S)-4-{[(3S,4R)-4-biphenyl-2-ylpyrrolidin-3-yl]carbonyl}-3-phenylmorpholine;
2-benzyl-1-{-[(3S,4R)-4-(2-bromophenyl)pyrrolidin-3-yl]carbonyl}pyrrolidine;
(3S)-4-{[(3S,4R)-4-(2-bromophenyl)pyrrolidin-3-yl]carbonyl}-3-phenylmorpholine;
(3S)-4-({(3S,4R)-4-[2-(1-methyl-1H-pyrazol-4-yl)phenyl]pyrrolidin-3-yl}carbonyl)-3-phenylmorpholine;
(3S)-4-{[(3S,4R)-4-(2'-fluorobiphenyl-2-yl)pyrrolidin-3-yl]carbonyl}-3-phenylmorpholine;
(3S)-4-{[(3S,4R)-4-(4'-ethoxybiphenyl-2-yl)pyrrolidin-3-yl]carbonyl}-3-phenylmorpholine;
1-{[(3S,4R)-4-(2-bromophenyl)pyrrolidin-3-yl]carbonyl}-4-[2-(4-chlorophenyl)ethyl]piperidine;
1'-{[(3S,4R)-4-(2-bromophenyl)pyrrolidin-3-yl]carbonyl}-3H-spiro[2-benzofuran-1,4'-piperidine];
2-benzyl-1-{[(3S,4R)-4-(4'-ethoxybiphenyl-2-yl)pyrrolidin-3-yl]carbonyl}pyrrolidine;
4-(2-{(3S,4S)-4-[(2-benzylpyrrolidin-1-yl)carbonyl]pyrrolidin-3-yl}phenyl)-1-methyl-1H-pyrazole;
2'-((3R,4S)-4-{[(3S)-3-phenylmorpholin-4-yl]carbonyl}pyrrolidin-3-yl)biphenyl-4-carbonitrile;
2'-((3R,4S)-4-{[(3S)-3-phenylmorpholin-4-yl]carbonyl}pyrrolidin-3-yl)biphenyl-3-carbonitrile;
(3S)-3-phenyl-4-({(3S,4R)-4-[3'-(trifluoromethyl)biphenyl-2-yl]pyrrolidin-3-yl}carbonyl)morpholine;
N-[2'-((3R,4S)-4-{[(3S)-3-phenylmorpholin-4-yl]carbonyl}pyrrolidin-3-yl)biphenyl-3-yl]methanesulfonamide;
(3S)-4-({(3S,4R)-4-[2-(2,3-dihydro-1,4-benzodioxin-6-yl)phenyl]pyrrolidin-3-yl}carbonyl)-3-phenylmorpholine;
(3S)-4-{[(3S,4R)-4-(4'-fluoro-2'-methylbiphenyl-2-yl)pyrrolidin-3-yl]carbonyl}-3-phenylmorpholine;
(3S)-3-phenyl-4-({(3S,4R)-4-[2-(3-thienyl)phenyl]pyrrolidin-3-yl}carbonyl)morpholine;
(3S)-4-({(3S,4R)-4-[2'-(benzyloxy)biphenyl-2-yl]pyrrolidin-3-yl}carbonyl)-3-phenylmorpholine;
(3S)-4-{[(3S,4R)-4-(4'-isobutylbiphenyl-2-yl)pyrrolidin-3-yl]carbonyl}-3-phenylmorpholine;
1-methyl-5-[2-((3R,4S)-4-{[(3S)-3-phenylmorpholin-4-yl]carbonyl}pyrrolidin-3-yl)phenyl]-1H-indole;
(3S)-4-({(3S,4R)-4-[4'-(methylsulfonyl)biphenyl-2-yl]pyrrolidin-3-yl}carbonyl)-3-phenylmorpholine;
1-[2'-((3R,4S)-4-{[(3S)-3-phenylmorpholin-4-yl]carbonyl}pyrrolidin-3-yl)biphenyl-4-yl]ethanone;
(3S)-4-({(3S,4R)-4-[4'-(morpholin-4-ylcarbonyl)biphenyl-2-yl]pyrrolidin-3-yl}carbonyl)-3-phenylmorpholine;
N-cyclopropyl-2'-((3R,4S)-4-{[(3S)-3-phenylmorpholin-4-yl]carbonyl}pyrrolidin-3-yl)biphenyl-4-carboxamide;
N-methyl-2'-((3R,4S)-4-{[(3S)-3-phenylmorpholin-4-yl]carbonyl}pyrrolidin-3-yl)biphenyl-4-amine;
{[2'-((3R,4S)-4-{[(3S)-3-phenylmorpholin-4-yl]carbonyl}pyrrolidin-3-yl)biphenyl-4-yl]oxy}acetonitrile;
(3S)-4-({(3S,4R)-4-[2-(6-chloropyridin-3-yl)phenyl]pyrrolidin-3-yl}carbonyl)-3-phenylmorpholine;
(3S)-4-({(3S,4R)-4-[2-(3,5-dimethylisoxazol-4-yl)phenyl]pyrrolidin-3-yl}carbonyl)-3-phenylmorpholine;
(3S)-4-({(3S,4R)-4-[2-(3-furyl)phenyl]pyrrolidin-3-yl}carbonyl)-3-phenylmorpholine;
5-[2-((3R,4S)-4-{[(3S)-3-phenylmorpholin-4-yl]carbonyl}pyrrolidin-3-yl)phenyl]pyridin-2-ol;
(3S)-4-[((3S,4R)-4-{2-[(1Z)-1-methylprop-1-en-1-yl]phenyl}pyrrolidin-3-yl)carbonyl]-3-phenylmorpholine;
1'-{[(3S,4R)-4-(2-bromophenyl)pyrrolidin-3-yl]carbonyl}spiro[indene-1,4'-piperidine];
1-{[(3S,4R)-4-(2-bromophenyl)pyrrolidin-3-yl]carbonyl}-4-phenylazepane;
1-{[(3S,4R)-4-(2-bromophenyl)pyrrolidin-3-yl]carbonyl}-2-(2-phenylethyl)pyrrolidine;
1-{[(3S,4R)-4-(2-bromophenyl)pyrrolidin-3-yl]carbonyl}-4-phenylpiperidine;
2'-((3R,4S)-4-{[(3S)-3-phenylmorpholin-4-yl]carbonyl}pyrrolidin-3-yl)biphenyl-4-ol;
(3S)-4-{[(3S,4R)-4-(4'-methylbiphenyl-2-yl)pyrrolidin-3-yl]carbonyl}-3-phenylmorpholine;
(3S)-4-{[(3S,4R)-4-(4'-fluorobiphenyl-2-yl)pyrrolidin-3-yl]carbonyl}-3-phenylmorpholine;
ethyl 2'-((3R,4S)-4-{[(3S)-3-phenylmorpholin-4-yl]carbonyl}pyrrolidin-3-yl)biphenyl-4-carboxylate;
N-[2'-((3R,4S)-4-{[(3S)-3-phenylmorpholin-4-yl]carbonyl}pyrrolidin-3-yl)biphenyl-4-yl]acetamide;
(3S)-4-({(3S,4R)-4-[2-(6-morpholin-4-ylpyridin-3-yl)phenyl]pyrrolidin-3-yl}carbonyl)-3-phenylmorpholine;
(3S)-3-phenyl-4-({(3S,4R)-4-[4'-(pyrrolidin-1-ylsulfonyl)biphenyl-2-yl]pyrrolidin-3-yl}carbonyl)morpholine;
(3S)-4-{[(3S,4R)-4-(4'-tert-butylbiphenyl-2-yl)pyrrolidin-3-yl]carbonyl}-3-phenylmorpholine;
(3S)-3-phenyl-4-{[(3S,4R)-4-(3'-propoxybiphenyl-2-yl)pyrrolidin-3-yl]carbonyl}morpholine;
(3S)-4-{[(3S,4R)-4-(3'-isopropoxybiphenyl-2-yl)pyrrolidin-3-yl]carbonyl}-3-phenylmorpholine;
(3S)-4-{[(3S,4R)-4-(4'-isopropoxybiphenyl-2-yl)pyrrolidin-3-yl]carbonyl}-3-phenylmorpholine;
(3S)-3-phenyl-4-{[(3S,4R)-4-(4'-propoxybiphenyl-2-yl)pyrrolidin-3-yl]carbonyl}morpholine;
(3S)-3-phenyl-4-({(3S,4R)-4-[4'-(trifluoromethyl)biphenyl-2-yl]pyrrolidin-3-yl}carbonyl)morpholine;
(3S)-4-{[(3S,4R)-4-(2'-methyl-4'-propoxybiphenyl-2-yl)pyrrolidin-3-yl]carbonyl}-3-phenylmorpholine;
(3S)-4-{[(3S,4R)-4-(4'-phenoxybiphenyl-2-yl)pyrrolidin-3-yl]carbonyl}-3-phenylmorpholine;
(3S)-4-{[(3S,4R)-4-(2'-fluoro-1,1':4',1"-terphenyl-2-yl)pyrrolidin-3-yl]carbonyl}-3-phenylmorpholine;
(3S)-3-phenyl-4-[((3S,4R)-4-{2-[(1E)-prop-1-en-1-yl]phenyl}pyrrolidin-3-yl)carbonyl]morpholine;
methyl (2S)-1-{[(3S,4R)-4-(2-bromophenyl)pyrrolidin-3-yl]carbonyl}piperidine-2-carboxylate;
methyl (2S)-1-{[(3S,4R)-4-(2-bromophenyl)pyrrolidin-3-yl]carbonyl}piperidine-2-carboxylate;
(3S)-3-benzyl-4-{[(3S,4R)-4-(2-bromophenyl)pyrrolidin-3-yl]carbonyl}morpholine;
1-{[(3S,4R)-4-(2-bromophenyl)pyrrolidin-3-yl]carbonyl}-2-phenylpiperidine;
1-({(3S,4R)-4-[4'-(methylsulfonyl)biphenyl-2-yl]pyrrolidin-3-yl}carbonyl)-4-phenylpiperidine;
1'-({(3S,4R)-4-[4'-(methylsulfonyl)biphenyl-2-yl]pyrrolidin-3-yl}carbonyl)spiro[indene-1,4'-piperidine];
(2R)-1-{[(3S,4R)-4-(2-bromophenyl)pyrrolidin-3-yl]carbonyl}-2-(fluoromethyl)pyrrolidine;
1-{[(3S,4R)-4-(2-bromophenyl)pyrrolidin-3-yl]carbonyl}-2-(4-methoxyphenyl)pyrrolidine;
1-{[(3S,4R)-4-(2-bromophenyl)pyrrolidin-3-yl]carbonyl}-2-(3,5-dichlorophenyl)pyrrolidine;
1-({(3S,4R)-4-[4'-(methylsulfonyl)biphenyl-2-yl]pyrrolidin-3-yl}carbonyl)-2-phenylpiperidine;

1-{[(3S,4R)-4-(2-bromophenyl)pyrrolidin-3-yl]carbonyl}-2,4-diphenylpiperidine;
1-{[(3S,4R)-4-(2-bromophenyl)pyrrolidin-3-yl]carbonyl}-4-(4-chlorophenyl)piperidine;
1-{[(3S,4R)-4-(2-bromophenyl)pyrrolidin-3-yl]carbonyl}-4-(2-fluorophenyl)piperidine;
1'-{[(3S,4R)-4-(2-bromophenyl)pyrrolidin-3-yl]carbonyl}-2,3-dihydrospiro[indene-1,4'-piperidine];
1-{[(3S,4R)-4-(2-bromophenyl)pyrrolidin-3-yl]carbonyl}-4-(4-methylphenyl)piperidine;
1-{[(3S,4R)-4-(2-bromophenyl)pyrrolidin-3-yl]carbonyl}-2,4-diphenylpiperidine;
1-{[(3S,4R)-4-(2-bromophenyl)pyrrolidin-3-yl]carbonyl}-2,4-diphenylpiperidine;
1-({(3S,4R)-4-[4'-(methylsulfonyl)biphenyl-2-yl]pyrrolidin-3-yl}carbonyl)-2,4-diphenylpiperidine;
2,4-diphenyl-1-{[(3S,4R)-4-phenylpyrrolidin-3-yl]carbonyl}piperidine;
(2R,4S)-1-{[(3S,4R)-4-(2-bromophenyl)pyrrolidin-3-yl]carbonyl}-2,4-diphenylpiperidine;
1'-{[(3S,4R)-4-(2-bromophenyl)pyrrolidin-3-yl]carbonyl}-2'-phenylspiro[indene-1,4'-piperidine];
1'-{[(3S,4R)-4-(2-bromophenyl)pyrrolidin-3-yl]carbonyl}-2'-phenylspiro[indene-1,4'-piperidine];
1'-{[(3S,4R)-4-(2-bromophenyl)pyrrolidin-3-yl]carbonyl}-2'-phenylspiro[indene-1,4'-piperidine];
1'-{[(3S,4R)-4-(2-bromophenyl)pyrrolidin-3-yl]carbonyl}-2'-(4-methoxyphenyl)spiro[indene-1,4'-piperidine];
1'-({(3S,4R)-4-[4'-(methylsulfonyl)biphenyl-2-yl]pyrrolidin-3-yl}carbonyl)-2'-phenylspiro[indene-1,4'-piperidine];
(2R,4S)-1-{[(3S,4R)-4-(2-allylphenyl)pyrrolidin-3-yl]carbonyl}-2,4-diphenylpiperidine;
2'-phenyl-1'-{[(3S,4R)-4-phenylpyrrolidin-3-yl]carbonyl}spiro[indene-1,4'-piperidine];
1'-{[(3S,4R)-4-(2-bromophenyl)pyrrolidin-3-yl]carbonyl}-2'-(4-chlorophenyl)spiro[indene-1,4'-piperidine];
(2R,4S)-1-{[(3S,4R)-4-(2-allylphenyl)pyrrolidin-3-yl]carbonyl}-2,4-diphenylpiperidine;
(2R,4S)-2,4-diphenyl-1-({(3S,4R)-4-[2-(1H-pyrrol-2-yl)phenyl]pyrrolidin-3-yl}carbonyl)piperidine;
4-[2-((3R,4S)-4-{[(2R,4S)-2,4-diphenylpiperidin-1-yl]carbonyl}pyrrolidin-3-yl)phenyl]pyridine;
5-[2-((3R,4S)-4-{[(2R,4S)-2,4-diphenylpiperidin-1-yl]carbonyl}pyrrolidin-3-yl)phenyl]pyrimidine;
3-[2-((3R,4S)-4-{[(2R,4S)-2,4-diphenylpiperidin-1-yl]carbonyl}pyrrolidin-3-yl)phenyl]pyridine;
2-chloro-5-[2-((3R,4S)-4-{[(2R,4S)-2,4-diphenylpiperidin-1-yl]carbonyl}pyrrolidin-3-yl)phenyl]pyridine;
(2R,4S)-2,4-diphenyl-1-({(3S,4R)-4-[2-(1H-pyrazol-4-yl)phenyl]pyrrolidin-3-yl}carbonyl)piperidine;
(2R,4S)-1-({(3S,4R)-4-[2-(1-methyl-1H-pyrazol-4-yl)phenyl]pyrrolidin-3-yl}carbonyl)-2,4-diphenylpiperidine;
(2S,4S)-1-({(3S,4R)-4-[2-(1-isobutyl-1H-pyrazol-4-yl)phenyl]pyrrolidin-3-yl}carbonyl)-2,4-diphenylpiperidine;
(2S,4S)-1-[((3S,4R)-4-{2-[1-(3-methylbutyl)-1H-pyrazol-4-yl]phenyl}pyrrolidin-3-yl)carbonyl]-2,4-diphenylpiperidine;
(2R,4S)-2,4-diphenyl-1-({(3S,4R)-4-[2-(1-propyl-1H-pyrazol-4-yl)phenyl]pyrrolidin-3-yl}carbonyl)piperidine;
(2R,4S)-1-{[(3S,4R)-4-(2-cyclohex-1-en-1-ylphenyl)pyrrolidin-3-yl]carbonyl}-2,4-diphenylpiperidine;
(2S,4S)-1-{[(3S,4R)-4-(2-cyclopropylphenyl)pyrrolidin-3-yl]carbonyl}-2,4-diphenylpiperidine;
(2S,4S)-2,4-diphenyl-1-({(3S,4R)-4-[2-(2-thienyl)phenyl]pyrrolidin-3-yl}carbonyl)piperidine;
(2R,4S)-1-({(3S,4R)-4-[2-(1-benzofuran-2-yl)phenyl]pyrrolidin-3-yl}carbonyl)-2,4-diphenylpiperidine;
(2S,4S)-1-{[(3S,4R)-4-(2-methylphenyl)pyrrolidin-3-yl]carbonyl}-2,4-diphenylpiperidine;
1-{[(3S,4R)-4-(2-bromophenyl)pyrrolidin-3-yl]carbonyl}-3-phenylpyrrolidine;
1-{[(3S,4R)-4-(2-bromophenyl)pyrrolidin-3-yl]carbonyl}-2-methyl-4-phenylpiperidine;
1-{[(3R,4R)-3-fluoro-4-phenylpyrrolidin-3-yl]carbonyl}-2,4-diphenylpiperidine;
(2S,4S)-1-{[(3S,4R)-4-(3-bromophenyl)pyrrolidin-3-yl]carbonyl}-2,4-diphenylpiperidine;
2-((3R,4S)-4-{[(2R,4S)-2,4-diphenylpiperidin-1-yl]carbonyl}pyrrolidin-3-yl)benzonitrile;
(2R,4S)-1-({(3S,4R)-4-[3-(methoxymethyl)phenyl]pyrrolidin-3-yl}carbonyl)-2,4-diphenylpiperidine;
1-({(3S,4R)-4-[3-(methoxymethyl)phenyl]pyrrolidin-3-yl}carbonyl)-4-phenylpiperidine;
1-{[(3S,4R)-4-(2-bromophenyl)pyrrolidin-3-yl]carbonyl}-4-methyl-4-phenylpiperidine;
1-{[(3S,4R)-4-(2-bromophenyl)pyrrolidin-3-yl]carbonyl}-4-phenyl-4-vinylpiperidine;
3-((3R,4S)-4-{[(2R,4S)-2,4-diphenylpiperidin-1-yl]carbonyl}pyrrolidin-3-yl)benzonitrile;
1-{[(3S,4R)-4-(2-bromophenyl)pyrrolidin-3-yl]carbonyl}-2-ethyl-4-phenylpiperidine;
(2S,4S)-1-({(3S,4R)-4-[3-(2-methoxyethyl)phenyl]pyrrolidin-3-yl}carbonyl)-2,4-diphenylpiperidine;
1-({(3S,4R)-4-[3-(2-methoxyethyl)phenyl]pyrrolidin-3-yl}carbonyl)-4-phenylpiperidine;
1-{[(3S,4R)-4-(2-bromophenyl)pyrrolidin-3-yl]carbonyl}-2-cyclopropyl-4-phenylpiperidine;
(2S,4S)-1-{[(3S,4R)-4-(2-bromophenyl)pyrrolidin-3-yl]carbonyl}-2,4-diphenylpiperidine;
1-{[(3S,4R)-4-(2-bromophenyl)pyrrolidin-3-yl]carbonyl}-4-(2-cyclopropylphenyl)-2-phenylpiperidine;
1-{[(3S,4R)-4-methyl-4-phenylpyrrolidin-3-yl]carbonyl}-4-phenylpiperidine;
1-{[(3S,4R)-4-(2-bromophenyl)pyrrolidin-3-yl]carbonyl}-2-isopropyl-4-phenylpiperidine;
1-{[(3S,4R)-4-(2-bromophenyl)pyrrolidin-3-yl]carbonyl}-4-methyl-2-phenylpiperidine;
4-phenyl-1-{[(3S,4R)-4-phenylpyrrolidin-3-yl]carbonyl}piperidine;
1-{[(3S,4R)-4-(2-bromophenyl)pyrrolidin-3-yl]carbonyl}-2-phenyl-4-propylpiperidine;
(2S,4R)-1-{[(3S,4R)-4-(2-bromophenyl)pyrrolidin-3-yl]carbonyl}-2-methyl-4-phenylpiperidine;
2-isopropyl-1-({(3S,4R)-4-[4'-(methylsulfonyl)biphenyl-2-yl]pyrrolidin-3-yl}carbonyl)-4-phenylpiperidine;
2-isopropyl-4-phenyl-1-{[(3S,4R)-4-phenylpyrrolidin-3-yl]carbonyl}piperidine;
3-((2R,4S)-1-{[(3S,4R)-4-(2-bromophenyl)pyrrolidin-3-yl]carbonyl}-2-phenylpiperidin-4-yl)pyridine;
(2R,4R)-1-{[(3S,4R)-4-(2-bromophenyl)pyrrolidin-3-yl]carbonyl}-2-methyl-4-phenylpiperidine;
2-((2R,4S)-1-{[(3S,4R)-4-(2-bromophenyl)pyrrolidin-3-yl]carbonyl}-2-phenylpiperidin-4-yl)pyridine;
(2S,4S)-1-{[(3S,4R)-4-methyl-4-phenylpyrrolidin-3-yl]carbonyl}-2,4-diphenylpiperidine;
(3S)-4-{[(3 S,4R)-4-methyl-4-phenylpyrrolidin-3-yl]carbonyl}-3-phenylmorpholine;

2-cyclopropyl-1-{[(3S,4R)-4-methyl-4-phenylpyrrolidin-3-yl]carbonyl}-4-phenylpiperidine;

2-isopropyl-1-{[(3S,4R)-4-methyl-4-phenylpyrrolidin-3-yl]carbonyl}-4-phenylpiperidine;

(2S,4S)-1-{[(3 S,4R)-4-(2-bromophenyl)pyrrolidin-3-yl]carbonyl}-2-isopropyl-4-phenylpiperidine;

(2S,4S)-1-{[(3S,4R)-4-(2-bromophenyl)pyrrolidin-3-yl]carbonyl}-2-methyl-4-phenylpiperidine;

N,N-dimethyl-4-{(3R,4S)-4-[(4-phenylpiperidin-1-yl)carbonyl]pyrrolidin-3-yl}aniline;

or a pharmaceutically acceptable salt thereof.

14. A pharmaceutical composition comprising a compound of any of claims 1-13, or a pharmaceutically acceptable salt thereof, and a pharmaceutically acceptable carrier.

\* \* \* \* \*